(12) United States Patent
Opalsky et al.

(10) Patent No.: US 10,190,984 B2
(45) Date of Patent: Jan. 29, 2019

(54) SYSTEMS AND METHODS FOR ANALYZING A SAMPLE AND FOR MONITORING THE PERFORMANCE OF AN OPTICAL SIGNAL DETECTOR

(71) Applicant: Gen-Probe Incorporated, San Diego, CA (US)

(72) Inventors: David Opalsky, San Diego, CA (US); Srajan Raghuwanshi, Escondido, CA (US); James Bui, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 185 days.

(21) Appl. No.: 15/389,897

(22) Filed: Dec. 23, 2016

(65) Prior Publication Data

US 2017/0191933 A1 Jul. 6, 2017

Related U.S. Application Data

(60) Provisional application No. 62/274,027, filed on Dec. 31, 2015.

(51) Int. Cl.
*G01N 21/75* (2006.01)
*G01N 21/64* (2006.01)
(Continued)

(52) U.S. Cl.
CPC ....... *G01N 21/645* (2013.01); *G01N 21/0332* (2013.01); *G01N 21/276* (2013.01);
(Continued)

(58) Field of Classification Search
CPC ......... G01N 21/645; G01N 2021/6441; G01N 2035/00356; G01N 2035/0455;
(Continued)

(56) References Cited

U.S. PATENT DOCUMENTS

2005/0287040 A1 12/2005 Giebeler et al.
2013/0344613 A1 12/2013 Li et al.
(Continued)

OTHER PUBLICATIONS

PCT, International Search Report and Written Opinion, International Patent Application No. PCT/US2016/068384, dated Mar. 30, 2017.
(Continued)

*Primary Examiner* — David Porta
*Assistant Examiner* — Faye Boosalis
(74) *Attorney, Agent, or Firm* — Charles B. Cappellari; Kyle E. Conklin

(57) ABSTRACT

A system for measuring optical signal detector performance includes an optical signal detector comprising a first detection channel having a first light source and a first sensor. The first detection channel is configured to emit and focus light generated by the first light source at a first detection zone, and to receive and focus light on the first sensor. The system also includes a controller operatively coupled to the optical signal detector and configured to determine an operational performance status of the optical signal detector based on at least one of (i) a first measured characteristic of light focused on the sensor while a first non-fluorescent surface portion is in the first detection zone and (ii) a second measured characteristic of light focused on the sensor while a void is in the first detection zone. The optical signal detector can be a fluorometer.

33 Claims, 27 Drawing Sheets

(51) Int. Cl.
  *G01N 21/03* (2006.01)
  *G01N 21/27* (2006.01)
  *G01N 35/02* (2006.01)
  G01N 35/00 (2006.01)
  G01N 35/04 (2006.01)
(52) U.S. Cl.
  CPC ........... *G01N 21/75* (2013.01); *G01N 35/025* (2013.01); *G01N 35/00732* (2013.01); *G01N 2021/6441* (2013.01); *G01N 2035/00356* (2013.01); *G01N 2035/0455* (2013.01); *G01N 2035/0475* (2013.01); *G01N 2035/0484* (2013.01); *G01N 2201/0407* (2013.01); *G01N 2201/0415* (2013.01); *G01N 2201/12723* (2013.01)
(58) Field of Classification Search
  CPC ......... G01N 2201/0415; G01N 35/026; G01N 21/0332; G01N 21/276; G01N 35/00732; G01N 2035/0475; G01N 2035/0484; G01N 21/75; G01N 2201/12723
  See application file for complete search history.

(56) References Cited

U.S. PATENT DOCUMENTS

| | | |
|---|---|---|
| 2014/0154792 A1 | 6/2014 | Moynihan et al. |
| 2015/0031121 A1 | 1/2015 | Nakatani et al. |

OTHER PUBLICATIONS

PCT, International Preliminary Report on Patentability, International Patent Application No. PCT/US2016/068384, dated Jul. 12, 2018.

SYSTEMS AND METHODS FOR ANALYZING A SAMPLE AND FOR MONITORING THE PERFORMANCE OF AN OPTICAL SIGNAL DETECTOR

CROSS-REFERENCE TO RELATED APPLICATION

This application claims the benefit of U.S. Provisional Application No. 62/274,027, which was filed Dec. 31, 2015, and which is incorporated by reference herein.

BACKGROUND

Field

Embodiments of this disclosure relate to systems and methods for analyzing a sample, for example, a biological sample, and for monitoring the performance of an optical signal detector, for example, a fluorometer.

Background

Diagnostic assays are used in clinical diagnosis and health science research to detect and/or quantify the presence and/or amount of biological antigens, cell abnormalities, disease states, and disease-associated pathogens present in a host organism or biological sample. Exemplary disease-associated pathogens include parasites, fungi, bacteria, and viruses. When a diagnostic assay permits quantification, practitioners can calculate the extent of infection or disease and determine the state of a disease over time. Diagnostic assays can detect, for example, chemicals, proteins, polysaccharides, nucleic acids, biopolymers, cells, or tissue of interest. A variety of assays may be employed to detect and/or qualify these diagnostic indicators.

To detect a targeted nucleic acid sequence, a probe having a nucleotide base sequence that is substantially complementary to the targeted sequence or its amplicon can be used. Under selective assay conditions, the probe can hybridize to the targeted sequence or its amplicon in a manner permitting a practitioner to detect the presence of the targeted sequence in a sample. Probes may include, for example, a detectable label such as a radiolabel, a fluorophore or fluorescent dye, biotin, an enzyme or a chemiluminescent compound. The probe can hybridize to the targeted sequence or its amplicon such that a signal indicating the presence of the targeted sequence in a sample can be detected, and the strength of the signal can be proportional to the amount of the target sequence or its amplicon that is present. By periodically measuring, during the amplification process, a signal indicative of the presence of amplicon, the growth of amplicon over time can be detected. Based on the data collected during this "real-time" monitoring of the amplification process, the amount of the target nucleic acid sequence that was originally in the sample can be ascertained.

To detect different nucleic acid sequences of interest in a single assay, different probes configured to hybridize to different nucleic acid sequences and to emit detectibly different signals can be used. For example, different probes configured to hybridize to different target nucleic acid sequences can be formulated with fluorophores that fluoresce at a known wavelength (i.e., color) when exposed to excitation light of a known excitation wavelength. Assays for detecting different target nucleic acid sequences can be performed in parallel by alternately exposing the sample to different excitation wavelengths and detecting the level of fluorescence at the wavelength of interest corresponding to the probe for each target nucleic acid sequence during the real-time monitoring process.

Parallel processing can be performed using different signal detectors configured to periodically measure signal emissions during the amplification process, and with different signal detectors configured to generate excitation signals of different wavelengths and to measure emission signals of different wavelengths. Exemplary signal detectors include fluorometers. One embodiment of an automated nucleic acid assay instrument is configured to process numerous samples carried in multiple receptacles, and each fluorometer is configured to acquire fluorometric readings from the receptacles as they are indexed past the fluorometer, for example, once every 2 seconds. Thus, 1800 times for each hour of operation of the instrument, each fluorometer can generate an excitation signal that is directed at the sample receptacle, and each fluorometer can measure the emission signal emitted by the contents of the receptacle and can generate an electrical signal that is proportional to the intensity of the emission signal. A fluorometer malfunction (e.g., device failure or deteriorated performance) during operation of the instrument will cause errors in the fluorometric readings generated by that fluorometer and thereby cause errors in the diagnostic results. Such malfunctions can be due to mechanical or electrical failures that occur during operation of the fluorometer. While the operation of the fluorometers can be checked during routine maintenance of the instrument, such opportunities for testing are rare because the testing can only be performed when the instrument is shut down. But the instrument can be operated continuously for extended periods of time for maximum throughput. Therefore, repeatedly shutting the instrument down to perform fluorometer functionality testing can be impractical and costly. Accordingly, a need exists for means and methodologies for periodically confirming the proper functionality of the signal detector, for example, a fluorometer, during the normal operation of the nucleic acid diagnostic instrument—while the assay is being performed.

SUMMARY

In some embodiments, an assay instrument includes a first fluorometer having a first detection channel having a first light source and a first sensor. The first detection channel is configured to emit and focus light generated by the first light source at a first detection zone, and to receive and focus light on the first sensor. The assay instrument also includes a carrier comprising a first non-fluorescent surface portion, defining a recess, configured to support a first receptacle. The carrier and the first fluorometer are movable relative to each other among at least (i) a first position at which a portion of the first receptacle is in the first detection zone, (ii) a second position at which the first non-fluorescent surface portion of the carrier is in the first detection zone, and (iii) a third position at which the recess is in the first detection zone. The assay instrument also includes a controller operatively coupled to the first fluorometer. The controller is configured to determine a characteristic of a sample contained within the first receptacle based on a first measured intensity of light focused on the first signal detector while the carrier is at the first position. The controller is also configured to determine an operational performance status of the first fluorometer based on at least one of (i) a second measured intensity of light focused on the first while the carrier is at the second position and (ii) a third measured intensity of light focused on the first sensor while the carrier is at the third position.

In some embodiments, the controller is configured to determine the operational performance status by determining whether the second measured intensity is within a first predetermined non-fluorescent-surface intensity range. The first predetermined non-fluorescent-surface intensity range can be greater than zero. For example, the first predetermined non-fluorescent-surface intensity range can be between 5-5800 Relative Fluorescent Units (RFU).

In some embodiments, the controller is configured to determine the operational performance status of the fluorometer by determining whether the third measured intensity is within a first predetermined recess intensity range. The first predetermined recess intensity range can include zero. For example, the first predetermined recess intensity range can be between 0-2260 Relative Fluorescent Units (RFU).

In some embodiments, the controller is configured to determine the operational performance status of the fluorometer based on both the second measured intensity and the third measured intensity. In some embodiments, the operational performance status is a failure status or a deteriorated performance status.

In some embodiments, the characteristic of the sample contained within the first receptacle is whether a particular analyte is present in the sample contained within the first receptacle. In some embodiments, the characteristic of the sample contained within the first receptacle is a quantity of a particular analyte in the sample contained within the first receptacle.

In some embodiments, the first fluorometer also includes a second detection channel having a second light source and a second sensor. The second detection channel is configured to emit and focus light generated by the second light source at a second detection zone, and to receive and focus light on the second sensor. The carrier can include a second non-fluorescent surface portion, and further configured to support a second receptacle. The carrier and the first fluorometer can be movable relative to each other among at least (i) the first position at which a portion of the second receptacle is in the second detection zone, (ii) the second position, (iii) the third position, and (iv) a fourth position at which the second non-fluorescent surface portion of the carrier is in the second detection zone. And the controller is also configured to determine a characteristic of a sample contained within the second receptacle based on a fourth measured intensity of light focused on the second sensor while the carrier is at the first position. The controller is also configured to determine the operational performance status of the first fluorometer further based on at least one of (i) a fifth measured intensity of light focused on the second sensor while the carrier is at the fourth position and (ii) a sixth measured intensity of light focused on the second sensor while the carrier is at the third position.

In some embodiments, the controller is configured to determine the operational performance status of the first fluorometer based on the fifth measured intensity by determining whether the fifth measured intensity is within a second predetermined non-fluorescent-surface intensity range. The first non-fluorescent surface portion and the second non-fluorescent surface portion can be linearly aligned and are coplanar. Each of the first non-fluorescent surface portion and the second non-fluorescent surface portion can include an aluminum surface.

In some embodiments, the controller can be configured to determine the operational performance status of the first fluorometer by determining whether the sixth measured intensity is within a second predetermined recess intensity range. In some embodiments, the controller is configured to determine the operational performance status of the first fluorometer based on both the fifth measured intensity and the sixth measured intensity.

In some embodiments, the assay instrument also includes a second fluorometer comprising a first detection channel having a first light source and a first sensor. The first detection channel of the second fluorometer is configured to emit and focus light generated by the first light source of the second fluorometer at a first detection zone of the second fluorometer, and to receive and focus light on the first sensor of the second fluorometer. The carrier also includes a third non-fluorescent surface portion, further defines a second recess, and is further configured to support a third receptacle. The carrier and the second fluorometer are movable relative to each other among at least (i) the first position at which a portion of the third receptacle is in the first detection zone of the second fluorometer, (ii) the second position at which the third non-fluorescent surface portion of the carrier is in the first detection zone of the second fluorometer, and (iii) the third position at which the second recess is in the first detection zone of the second fluorometer. The controller is further configured to determine a characteristic of a sample contained within the third receptacle based on a seventh measured intensity of light focused on the first sensor of the second fluorometer while the carrier is at the first position. And the controller is further configured to determine an operational performance status of the second fluorometer based on at least one of (i) an eighth measured intensity of light focused on the first sensor of the second fluorometer while the carrier is at the second position and (ii) a ninth measured intensity of light focused on the first sensor of the second fluorometer while the carrier is at the third position.

In some embodiments, the controller is configured to determine the operational performance status of the second fluorometer by determining whether the eighth measured intensity is within a third predetermined non-fluorescent-surface intensity range. The third predetermined non-fluorescent-surface intensity range can be greater than zero. The third predetermined non-fluorescent-surface intensity range can be between 5-5800 Relative Fluorescent Units (RFU).

In some embodiments, the controller is configured to determine the operational performance status of the second fluorometer by determining whether the ninth measured intensity is within a third predetermined recess intensity range. The third predetermined recess intensity range can include zero. The third predetermined recess intensity range can be between 0-2260 Relative Fluorescent Units (RFU).

In some embodiments, the controller is configured to determine the operational performance status of the second fluorometer based on both the eighth measured intensity and the ninth measured intensity.

In some embodiments, the characteristic of the sample contained within the third receptacle is whether a particular analyte is present in the sample contained within the third receptacle. In some embodiments, the characteristic of the sample contained within the third receptacle is a quantity of a particular analyte in the sample contained within the third receptacle.

In some embodiments, the second fluorometer further comprises a second detection channel having a second light source and a second sensor. The second detection channel of the second fluorometer is configured to emit and focus light generated by the second light source of the second fluorometer at a second detection zone, and to receive and focus light on the second sensor of the second fluorometer. The carrier further comprises a fourth non-fluorescent surface portion, and is further configured to support a fourth receptacle. The carrier and the second fluorometer are movable relative to each other among at least (i) the first position at which a portion of the fourth receptacle is in the second detection zone of the second fluorometer, (ii) the second position, (iii) the third position, and (iv) the fourth position at which the fourth non-fluorescent surface portion of the carrier is in the second detection zone of the second fluorometer. The controller is further configured to determine a characteristic of a sample contained within the fourth receptacle based on a tenth measured intensity of light focused on the second sensor of the second fluorometer while the carrier is at the first position. The controller is further configured to determine the operational performance status of the second fluorometer further based on at least one of (i) a eleventh measured intensity of light focused on the second sensor of the second fluorometer while the carrier is at the fourth position and (ii) a twelfth measured intensity of light focused on the second sensor of the second fluorometer while the carrier is at the third position.

In some embodiments, the controller is configured to determine the operational performance status of the second fluorometer by determining whether the eleventh measured intensity is within a fourth predetermined non-fluorescent-surface intensity range. The third non-fluorescent surface portion and the fourth non-fluorescent surface portion can be linearly aligned and are coplanar. Each of the third non-fluorescent surface portion and the fourth non-fluorescent surface portion can include an aluminum surface.

In some embodiments, the controller is further configured to determine the operational performance status of the second fluorometer by determining whether the twelfth measured intensity is within a fourth recess intensity range. In some embodiments, the controller is further configured to determine the operational performance status of the second fluorometer based on both the eleventh measured intensity and the twelfth measured intensity.

In some embodiments, a distance between the first fluorometer and the portion of the first receptacle at the first position is greater than a distance between the first fluorometer and the first non-fluorescent surface portion at the second position. In some embodiments, a distance between the first fluorometer and the portion of the first receptacle at the first position is less than a distance between the first fluorometer and the first non-fluorescent surface portion at the second position.

In some embodiments, the carrier is a carousel having a first disk and a second disk spaced apart from the first disk, the second disk being between the first disk and the first fluorometer. The second disk includes the first non-fluorescent surface portion and defines an opening of the first recess. The second disk can also include concentric inner and outer rings connected by a spoke that includes the first non-fluorescent surface portion.

In some embodiments, the carrier is movable, and the first fluorometer is stationary. The carrier can be rotatable. In other embodiments, the carrier is movable, and the first fluorometer is movable. In other embodiments, the carrier is stationary, and the first fluorometer is movable.

In some embodiments, a method of analyzing a sample includes positioning a carrier such that a first non-fluorescent surface portion on the carrier is in a first detection zone of a first fluorometer. The method also includes directing light emitted from the first fluorometer onto the first non-fluorescent surface portion in the first detection zone of the first fluorometer, and measuring a first intensity of light detected by a first sensor of the first fluorometer while the first non-fluorescent surface portion is in the first detection zone of the first fluorometer. The method also includes positioning the carrier and the first fluorometer relative to each other such that a first recess defined by the carrier is in the first detection zone of the first fluorometer. The method further includes directing light emitted from the fluorometer into the first recess in the first detection zone of the first fluorometer, and measuring a second intensity of light detected by the first sensor of the first fluorometer while the first recess is in the first detection zone of the first fluorometer. And the method includes determining an operational performance status of the first fluorometer based on at least one of the first intensity and the second intensity.

In some embodiments, the method also includes positioning the carrier and the first fluorometer relative to each other such that a portion of a first receptacle supported by the carrier is in the first detection zone of the first fluorometer, and directing light emitted from the first fluorometer into the portion of the first receptacle in the first detection zone of the first fluorometer. And the method includes measuring a third intensity of light detected by the first sensor of the first fluorometer while the portion of the first receptacle is in the first detection zone of the first fluorometer, and determining a characteristic of a sample contained within the first receptacle based on the third intensity.

The characteristic of the sample contained within the first receptacle can be whether a particular analyte is present in the sample contained within the first receptacle. The characteristic of the sample contained within the first receptacle can be a quantity of a particular analyte in the sample contained within the first receptacle.

In some embodiments, a distance between the first fluorometer and the portion of the first receptacle in the first detection zone of the first fluorometer is greater than a distance between the first fluorometer and the first non-fluorescent surface portion in the first detection zone of the first fluorometer. In some embodiments, a distance between the first fluorometer and the portion of the first receptacle in the first detection zone of the first fluorometer is less than a distance between the first fluorometer and the first non-fluorescent surface portion in the first detection zone of the first fluorometer.

In some embodiments, determining the operational performance status of the first fluorometer based on at least one of the first intensity and the second intensity comprises determining whether the first intensity is within a first predetermined non-fluorescent-surface intensity range. The first predetermined non-fluorescent-surface intensity range can be greater than zero. The first predetermined non-fluorescent-surface intensity range can be between 5-5800 Relative Fluorescent Units (RFU).

In some embodiments, determining the operational performance status of the first fluorometer based on at least one of the first intensity and the second intensity comprises determining whether the second intensity is within a first predetermined recess intensity range. The first predetermined recess intensity range can include zero. The first predetermined recess intensity range can be between 0-2260 Relative Fluorescent Units (RFU).

In some embodiments, the method also includes determining the operational performance status of the fluorometer based on both the first intensity and the second intensity. In some embodiments, the operational performance status is a failure status or a deteriorated performance status.

In some embodiments, the method also includes positioning the carrier and the first fluorometer relative to each other such that a second non-fluorescent surface portion on the carrier is in a second detection zone of the first fluorometer, and directing light emitted from the first fluorometer onto the second non-fluorescent surface portion in the second detection zone of the first fluorometer. And the method includes measuring a fourth intensity of light detected by a second sensor of the first fluorometer while the second non-fluorescent surface portion is in the second detection zone of the first fluorometer. The method also includes positioning the carrier and the first fluorometer relative to each other such that the first recess is in the second detection zone of the first fluorometer. The method also includes directing light emitted from the first fluorometer into the first recess in the second detection zone of the first fluorometer, and measuring a fifth intensity of light detected by the second sensor of the first fluorometer while the first recess is in the second detection zone of the first fluorometer. And the method includes determining the operational performance status of the first fluorometer based on at least one of the fourth intensity and the fifth intensity.

In some embodiments, while the portion of the first receptacle is in the first detection zone of the first fluorometer, a portion of a second receptacle supported by the carrier is in the second detection zone of the first fluorometer.

In some embodiments, the method also includes directing light emitted from the fluorometer into the portion of the second receptacle in the second detection zone of the first fluorometer, and measuring a sixth intensity of light detected by the second sensor of the first fluorometer while the portion of the second receptacle is in the second detection zone of the first fluorometer. And the method includes determining a characteristic of a sample contained within the second receptacle based on the sixth intensity.

In some embodiments, determining the operational performance status of the first fluorometer based on at least one of the fourth intensity and the fifth intensity comprises determining whether the fourth intensity is within a second predetermined non-fluorescent-surface intensity range. The first non-fluorescent surface portion and the second non-fluorescent surface portion can be linearly aligned and are coplanar. Each of the first non-fluorescent surface portion and the second non-fluorescent surface portion can include an aluminum surface.

In some embodiments, determining the operational performance status of the first fluorometer based on at least one of the fourth intensity and the fifth intensity comprises determining whether the fifth intensity is within a second predetermined recess intensity range.

In some embodiments, determining the operational performance status of the first fluorometer based on at least one of the fourth intensity and the fifth intensity comprises determining the operational performance status of the fluorometer based on both the fifth intensity and the sixth intensity.

In some embodiments, the method also includes positioning the carrier and the second fluorometer relative to each other such that a third non-fluorescent surface portion on the carrier is in a first detection zone of a second fluorometer. The method also includes directing light emitted from the second fluorometer onto the third non-fluorescent surface portion in the first detection zone of the second fluorometer, and measuring a sixth intensity of light detected by a first sensor of the second fluorometer while the third non-fluorescent surface portion is in the first detection zone of the second fluorometer. The method further includes positioning the carrier and the second fluorometer relative to each other such that a second recess defined by the carrier is in the first detection zone of the second fluorometer. And the method includes directing light emitted from the fluorometer into the second recess in the first detection zone of the second fluorometer, and measuring a seventh intensity of light detected by the first sensor of the second fluorometer while the second recess is in the first detection zone of the second fluorometer. The method also includes determining an operational performance status of the second fluorometer based on at least one of the sixth intensity and the seventh intensity.

In some embodiments, while the third non-fluorescent surface portion on the carrier is in the first detection zone of a second fluorometer, the first non-fluorescent surface portion on the carrier is in the first detection zone of the first fluorometer.

In some embodiments, the method also includes positioning the carrier and the second fluorometer relative to each other such that a portion of a third receptacle supported by the carrier is in the first detection zone of the second fluorometer. The method further includes directing light emitted from the second fluorometer into the portion of the third receptacle in the first detection zone of the second fluorometer, and measuring an eighth intensity of light detected by the first sensor of the second fluorometer while the portion of the third receptacle is in the first detection zone of the second fluorometer. And the method includes determining a characteristic of a sample contained within the third receptacle based on the eighth intensity.

In some embodiments, while the portion of the first receptacle is in the first detection zone of the first fluorometer, the portion of the third receptacle supported by the carrier is in the first detection zone of the second fluorometer.

In some embodiments, the characteristic of the sample contained within the third receptacle can be whether a particular analyte is present in the sample. In some embodiments, the characteristic of the sample contained within the third receptacle can be a quantity of a particular analyte in the sample.

In some embodiments, determining the operational performance status of the second fluorometer based on at least one of the sixth intensity and the seventh intensity comprises determining whether the sixth intensity is within a third predetermined non-fluorescent-surface intensity range. The third predetermined non-fluorescent-surface intensity range can be greater than zero. The third predetermined non-fluorescent-surface intensity range can be between 5-5800 Relative Fluorescent Units (RFU).

In some embodiments, determining the operational performance status of the second fluorometer based on at least one of the sixth intensity and the seventh intensity comprises determining whether the seventh intensity is within a third predetermined recess intensity range. The third predetermined recess intensity range can include zero. The third predetermined recess intensity range can be between 0-2260 Relative Fluorescent Units (RFU).

In some embodiments, determining the operational performance status of the second fluorometer based on at least one of the sixth intensity and the seventh intensity is based on both the sixth intensity and the seventh intensity.

In some embodiments, the method also includes positioning the carrier and the second fluorometer relative to each other such that a fourth non-fluorescent surface portion on the carrier is in a second detection zone of the second fluorometer. The method further includes directing light emitted from the second fluorometer onto the fourth non-fluorescent surface portion in the second detection zone of the second fluorometer, and measuring a ninth intensity of light detected by a second sensor of the second fluorometer while the fourth non-fluorescent surface portion in the second detection zone of the second fluorometer. The method also includes positioning the carrier and the second fluorometer relative to each other such that the second recess is in the second detection zone of the second fluorometer. And the method includes directing light emitted from the second fluorometer into the second recess in the second detection zone of the second fluorometer, and measuring a tenth intensity of light detected by the second sensor of the second fluorometer while the second recess is in the second detection zone of the second fluorometer. And the method includes determining the operational performance status of the second fluorometer based on at least one of the ninth intensity and the tenth intensity.

In some embodiments, the method also includes positioning the carrier and the second fluorometer relative to each other such that a portion of a fourth receptacle supported by the carrier is in the second detection zone of the second fluorometer. The method further includes directing light emitted from the second fluorometer into the portion of the fourth receptacle in the second detection zone of the second fluorometer, and measuring a eleventh intensity of light detected by the second sensor of the second fluorometer while the portion of the fourth receptacle is in the second detection zone of the second fluorometer. And the method includes determining a characteristic of a sample contained within the fourth receptacle based on the eleventh intensity.

In some embodiments, the characteristic of the sample contained within the fourth receptacle can be whether a particular analyte is present in the sample contained within the fourth receptacle. In some embodiments, the characteristic of the sample contained within the fourth receptacle can be a quantity of a particular analyte in the sample contained within the fourth receptacle.

In some embodiments, determining the operational performance status of the second fluorometer based on at least one of the ninth intensity and the tenth intensity comprises determining whether the ninth intensity is within a fourth predetermined non-fluorescent-surface intensity range. The third non-fluorescent surface portion and the fourth non-fluorescent surface portion can be linearly aligned and are coplanar. In some embodiments, each of the third non-fluorescent surface portion and the fourth non-fluorescent surface portion comprises an aluminum surface.

In some embodiments, determining the operational performance status of the second fluorometer based on at least one of the ninth intensity and the tenth intensity comprises determining whether the tenth intensity is within a fourth recess intensity range.

In some embodiments, determining the operational performance status of the second fluorometer based on at least one of the ninth intensity and the tenth intensity is based on both the ninth intensity and the tenth intensity.

In some embodiments, the carrier is a carousel comprising a first disk and a second disk spaced apart from the first disk, the second disk being between the first disk and the first fluorometer. And the second disk includes the first non-fluorescent surface portion and defines an opening of the first recess. The second disk can comprise concentric inner and outer rings connected by a spoke that includes the first non-fluorescent surface portion.

In some embodiments, positioning the carrier and the first fluorometer relative to each other such that the first non-fluorescent surface portion on the carrier is in the first detection zone of the first fluorometer comprises moving the carrier while the first fluorometer remains stationary, and positioning the carrier and the first fluorometer relative to each other such that the first recess defined by the carrier is in the first detection zone of the first fluorometer comprises moving the carrier while the first fluorometer remains stationary. In other embodiments, positioning the carrier and the first fluorometer relative to each other such that the first non-fluorescent surface portion on the carrier is in the first detection zone of the first fluorometer comprises moving the first fluorometer while the carrier remains stationary, and positioning the carrier and the first fluorometer relative to each other such that the first recess defined by the carrier is in the first detection zone of the first fluorometer comprises moving the first fluorometer while the carrier remains stationary. In other embodiments, positioning the carrier and the second fluorometer relative to each other such that the third non-fluorescent surface portion on the carrier is in the first detection zone of the second fluorometer comprises moving the second fluorometer and moving the carrier, and positioning the carrier and the second fluorometer relative to each other such that the second recess defined by the carrier is in the first detection zone of the second fluorometer comprises moving the second fluorometer and moving the carrier.

In some embodiments, a system for measuring optical signal detector performance includes an optical signal detector comprising a first detection channel having a first light source and a first sensor. The first detection channel is configured to emit and focus light generated by the first light source at a first detection zone, and to receive and focus light on the first sensor. The system also includes a controller operatively coupled to the optical signal detector and configured to determine an operational performance status of the optical signal detector based on at least one of (i) a first measured characteristic of light focused on the sensor while a first non-fluorescent surface portion is in the first detection zone and (ii) a second measured characteristic of light focused on the sensor while a void is in the first detection zone.

In some embodiments, each of the first measured characteristic and the second measured characteristic is an intensity of light.

In some embodiments, the controller is configured to determine the operational performance status by determining whether the first measured characteristic is within a first predetermined non-fluorescent-surface characteristic range. In some embodiments, the controller is configured to determine the operational performance status of the optical signal detector by determining whether the second measured characteristic is within a first predetermined void intensity range. In some embodiments, the controller is configured to determine the operational performance status of the optical signal detector based on both the first measured characteristic and the second measured characteristic. In some embodiments, the operational performance status is a proper operational performance status, a failure status, and a deteriorated performance status.

In some embodiments, the optical signal detector further comprises a second detection channel having a second light source and a second sensor. The second detection channel being configured to emit and focus light generated by the second light source at a second detection zone, and to receive and focus light on the second sensor. And the controller is further configured to determine the operational performance status of the first optical signal detector further based on at least one of (i) a third measured characteristic of light focused on the second sensor while a second non-fluorescent surface portion is in the second detection zone and (ii) a fourth measured characteristic of light focused on the second sensor while the void is in the second detection zone.

In some embodiments, the controller is configured to determine the operational performance status of the optical signal detector based on the third measured characteristic by determining whether the third measured characteristic is within a second predetermined non-fluorescent-surface characteristic range.

In some embodiments, each of the first non-fluorescent surface portion and the second non-fluorescent surface portion can comprise an aluminum surface.

In some embodiments, the controller is configured to determine the operational performance status of the optical signal detector by determining whether the fourth measured characteristic is within a second predetermined void characteristic range. In some embodiments, the controller is configured to determine the operational performance status of the optical signal detector based on both the third measured characteristic and the fourth measured characteristic.

In some embodiments, the optical signal detector is a fluorometer.

In some embodiments, a method for measuring optical signal detector performance includes aligning a first non-fluorescent surface portion with a first detection zone of an optical signal detector. The method also includes directing light emitted from the optical signal detector onto the first non-fluorescent surface portion in the first detection zone of the optical signal detector, and measuring a first characteristic of light detected by a first sensor of the first optical signal detector while the first non-fluorescent surface portion is in the first detection zone of the optical signal detector. The method also includes positioning a first void in the first detection zone of the first optical signal detector. The method further includes directing light emitted from the optical signal detector into the first void in the first detection zone of the optical signal detector, and measuring a second characteristic of light detected by the first sensor of the optical signal detector while the first void is in the first detection zone of the optical signal detector. And the method includes determining an operational performance status of the optical signal detector based on at least one of the first characteristic and the second characteristic.

In some embodiments, the first measured characteristic is a first intensity of light and the second measured characteristic is a second intensity of light.

In some embodiments, determining the operational performance status of the optical signal detector based on at least one of the first measured characteristic and the second measured characteristic comprises determining whether the first measured characteristic is within a first predetermined non-fluorescent-surface characteristic range. In some embodiments, determining the operational performance status of the optical signal detector based on at least one of the first measured characteristic and the second measured characteristic comprises determining whether the second measured characteristic is within a first predetermined void characteristic range. In some embodiments, the method includes determining the operational performance status of the optical signal detector based on both the first measured characteristic and the second measured characteristic.

In some embodiments, the operational performance status is a proper operational performance status, a failure status, and a deteriorated performance status.

In some embodiments, the method also includes positioning a second non-fluorescent surface portion in a second detection zone of the optical signal detector. The method also includes directing light emitted from the optical signal detector onto the second non-fluorescent surface portion in the second detection zone of the optical signal detector, and measuring a third characteristic of light detected by a second sensor of the optical signal detector while the second non-fluorescent surface portion is in the second detection zone of the optical signal detector. The method also includes positioning the first void in the second detection zone of the optical signal detector. The method further includes directing light emitted from the optical signal detector into the first void in the second detection zone of the optical signal detector, and measuring a fourth characteristic of light detected by the second sensor of the optical signal detector while the first void is in the second detection zone of the optical signal detector. And the method includes determining the operational performance status of the optical signal detector based on at least one of the third measured characteristic and the fourth measured characteristic.

In some embodiments, determining the operational performance status of the optical signal detector based on at least one of the third measured characteristic and the fourth measured characteristic comprises determining whether the third measured characteristic is within a second predetermined non-fluorescent-surface characteristic range. In some embodiments, each of the first non-fluorescent surface portion and the second non-fluorescent surface portion comprises an aluminum surface. In some embodiments, determining the operational performance status of the first third measured characteristic based on at least one of the third measured characteristic and the fourth measured characteristic comprises determining whether the fourth measured characteristic is within a second predetermined void characteristic range. In some embodiments, determining the operational performance status of the optical signal detector based on at least one of the third measured characteristic and the fourth measured characteristic comprises determining the operational performance status of the optical signal detector based on both the third measured characteristic and the fourth measured characteristic.

In some embodiments, the optical signal detector is a fluorometer.

Further features and advantages of the embodiments, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

DESCRIPTION OF THE DRAWINGS

The accompanying drawings, which are incorporated herein and form a part of the specification, illustrate the embodiments and, together with the description, further serve to explain the principles of the embodiments and to enable a person skilled in the relevant art(s) to make and use the embodiments.

DETAILED DESCRIPTION

The present disclosure will now be described in detail with reference to embodiments thereof as illustrated in the accompanying drawings. References to "one embodiment," "an embodiment," "some embodiments," "an exemplary embodiment," "for example," "an example," "exemplary," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "a" or "an" means "at least one" or "one or more."

As used herein, a "sample" refers to any material to be analyzed, regardless of the source. The material may be in its native form or any stage of processing (e.g., the material may be chemically altered or it may be one or more components of a sample that have been separated and/or purified from one or more other components of the sample). A sample may be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

Multiple Receptacle Devices

Figure 1:
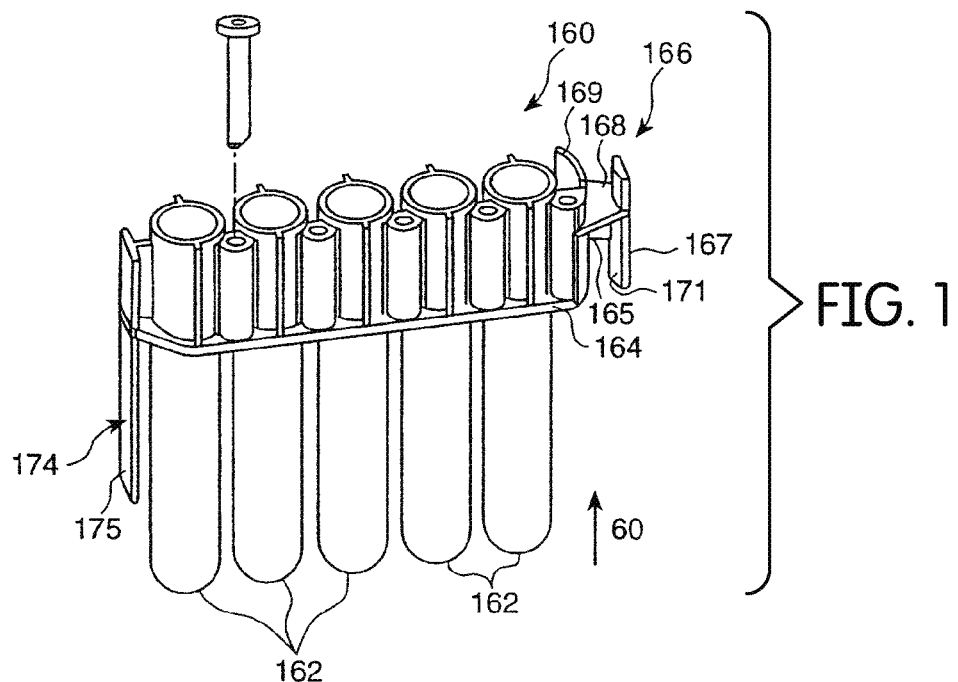
FIG. 1 is a perspective view of a reaction receptacle in the form of a multiple receptacle device unit employed in combination with an apparatus, according to an embodiment.

A plurality of reaction receptacles 162 according to one embodiment are shown in FIG. 1. In this embodiment, some receptacles 162 are formed as one integral multiple receptacle device ("MRD") 160. In other embodiments (not shown), receptacles 162 can be separate and individualized from other receptacles 162.

Figure 5:
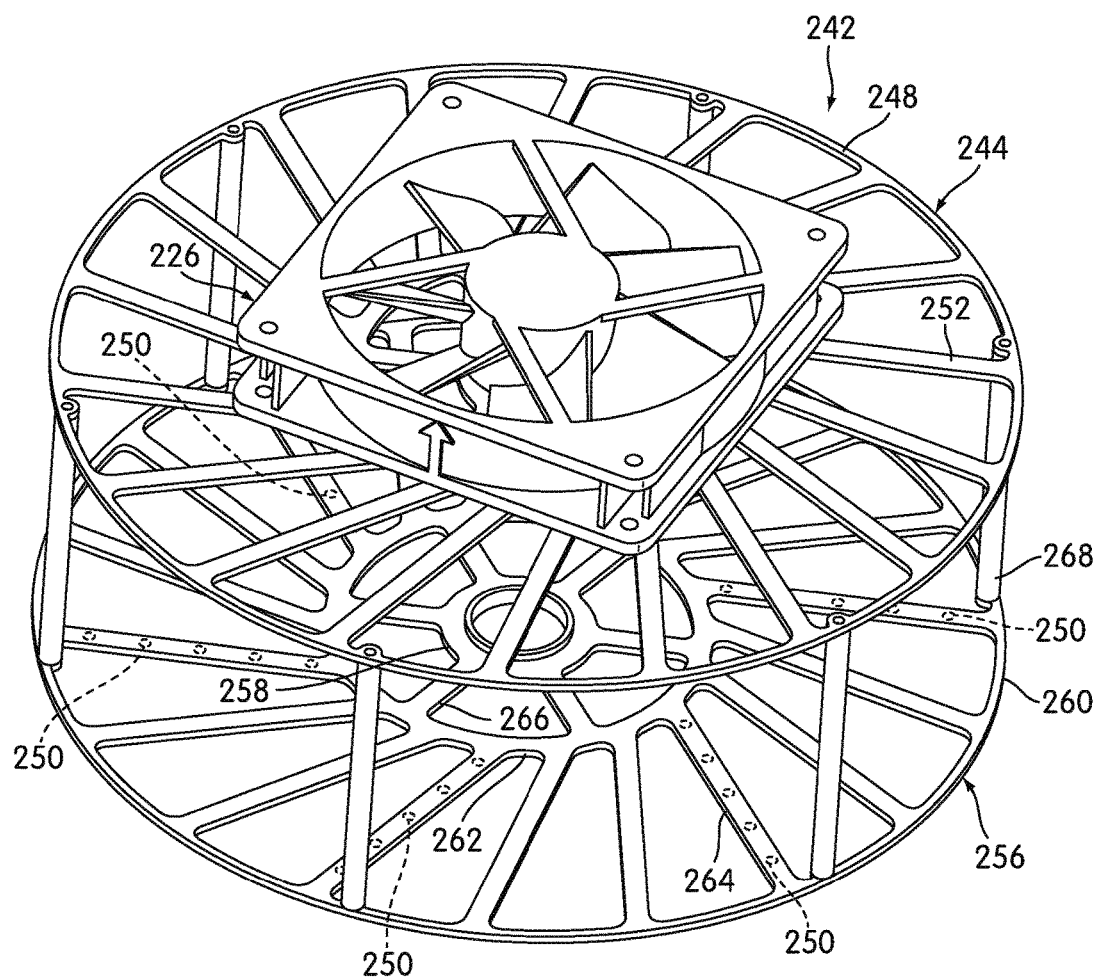
FIG. 5 is a perspective view of assembled components of a receptacle carrier carousel of the incubator and a circulating fan for generating airflow within the incubator, according to an embodiment.

In some embodiments, as shown in FIG. 5, MRD 160 includes five receptacles 162. In other embodiments, MRD 160 includes more or less than five receptacles 162. Receptacles 162, for example, in the form of cylindrical tubes with open top ends and closed bottom ends, are connected to one another by a connecting rib structure 164 which defines a downwardly facing shoulder extending longitudinally along either side of MRD 160.

In some embodiments, MRD 160 is formed from injection molded polypropylene, such as those sold by Montell Polyolefins, of Wilmington, Del., product number PD701NW or Huntsman, product number P5M6K-048. In other embodiments, receptacles 162 of MRD 160 are releasably fixed with respect to each other, for example, by being supported by a separated sample receptacle rack.

MRD 160 can include an arcuate shield structure 169 at one end. MRD 160 can also include an MRD manipulating structure 166 that extends from shield structure 169. Manipulating structure 166 can be adapted to be engaged by a transport mechanism that moves MRD 160 between different components of an assay instrument. MRD manipulating structure 166 can include a laterally extending plate 168 that extends from shield structure 169 with a vertically extending piece 167 on the opposite end of plate 168. A gusset wall 165 extends downwardly from lateral plate 168 between shield structure 169 and vertical piece 167.

Figure 2:
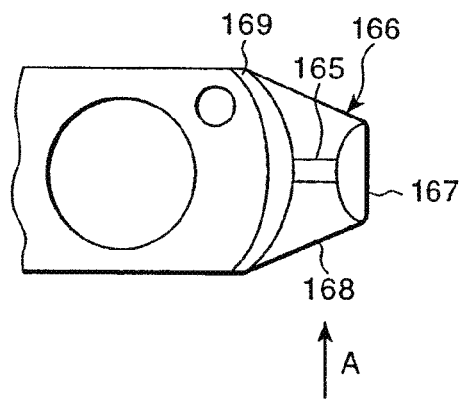
FIG. 2 is an enlarged bottom view of a portion of the multiple receptacle device, viewed in the direction of arrow "60" in FIG. 1, according to an embodiment.

As shown in FIG. 2, shield structure 169 and vertical piece 167 have mutually facing convex surfaces in some embodiments. MRD 160 may be engaged by a transport mechanism and other components, by moving an engaging member laterally (in the direction "A") into the space between shield structure 169 and vertical piece 167. The convex surfaces of shield structure 169 and vertical piece 167 provide for wider points of entry for an engaging member undergoing a lateral relative motion into the space.

MRD 160 can include a label-receiving structure 174 having a flat label-receiving surface 175 on an end of MRD 160 opposite shield structure 169 and MRD manipulating structure 166. Human or machine-readable labels, such as scannable bar codes, can be placed on surface 175 to provide identifying and instructional information on MRD 160.

Nucleic Acid Diagnostic Assays

Some embodiments use apparatuses and procedures that can be used in conjunction with nucleic acid diagnostic assays, including "real-time" amplification assays and "end-point" amplification assays.

Real-time amplification assays can be used to determine the presence and amount of a target nucleic acid in a sample which, by way of example, is derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations.

In addition to real-time amplification assays, some embodiments implement end-point amplification assays. In end-point amplification assays, the presence of amplification products containing the target sequence or its complement is determined at the conclusion of an amplification procedure. The determination may occur in a detection station that may be located externally to the incubator in which the amplification reactions occur. In contrast, in "real-time" amplification assays, the amount of amplification products containing the target sequence or its complement is determined during an amplification procedure. In a real-time amplification assay, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

In an exemplary real-time amplification assay, the interacting labels include a fluorescent moiety, or other emission moiety, and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to nucleic acid present in the sample, the fluorescent and quencher moieties are separated from each other and light energy emitted by the fluorescent moiety can be detected. Fluorescent moieties which are excited and emit at different and distinguishable wavelengths can be combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties.

Where an amplification procedure is used to increase the amount of target sequence, or its complement, present in a sample before detection can occur, a "control" can be included to ensure that amplification has taken place and, thereby, to avoid false negatives. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus rendering any results from that assay suspect. Alternatively, failure to detect emission light may be due to failure or deteriorated mechanical and/or electrical performance of an instrument (described below) for detecting the emission light. In some embodiments, methods and apparatuses detect such failure or deteriorated performance. Here, "performance" means the reliability of the instrument's operation such that output of the instrument may be relied upon in deriving an assay or test result. Instrument failure or deteriorated performance may be detected in some embodiments by acquiring an objectively measurable characteristic of the instrument's output that deviates from an output that would be normally expected under similar operation conditions if the instrument were operating properly. Examples of such objectively measurable characteristics that may be indicative of instrument failure or deteriorated performance include an unexpected decrease in the intensity of the instrument output or a spike in the instrument output.

In some embodiments, amplification assays are performed in an incubator, such as an incubator 200 as shown in FIGS. 3-10. In some embodiments, incubator 200 is a rotary incubator that supports and moves MRDs 160 by a rotary carrier 242 (e.g., a carousel) within a controlled temperature housing. Incubator 200 can include one or more signal detectors 400 attached thereto configured to detect, in real-time, the amplification occurring within the receptacles 162 of MRD 160 carried in incubator 200. For example, signal detectors 400 can be a fluorometer configured to measure the fluorescence emitted by a dye or dyes within each receptacle 162 of MRD 160 when receptacles 162 of MRD 160 is illuminated with an excitation light corresponding to each dye.

In some embodiments, incubator 200 is integrated into an automated assay instrument (not shown) that may include one or more receptacle transport mechanisms for placing MRDs 160 into incubator 200 and removing MRDs 160 from incubator 200. As used herein, an "assay instrument" refers to any instrument capable of analyzing a sample and rendering a result. As used herein, a "sample" refers to any material to be analyzed, regardless of the source. The material may be in its native form or any stage of processing (e.g., the material may be chemically altered or it may be one or more components of a sample that have been separated and/or purified from one or more other components of the sample). A sample may be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample. Any instrument capable of performing a hybridization assay, an amplification assay, a sequencing assay, or an immunoassay on a sample is included in this definition of an assay instrument. In some embodiments, an assay can be carried out directly on a sample without any sample processing, but other samples require processing before carrying out an assay. Samples requiring some form of sample processing before subjecting the samples to the steps of an assay include, in some embodiments, cell samples, tissue samples, stool samples, mucus samples, semen samples, cerebrospinal fluid samples, blood samples, bone marrow samples, serum samples, urine samples, bile samples, respiratory samples, sputum samples, and exosome samples, among others. Exemplary assay instruments include the Tigris® and Panther® systems sold by Hologic, Inc., Bedford, Mass.

Figure 3:
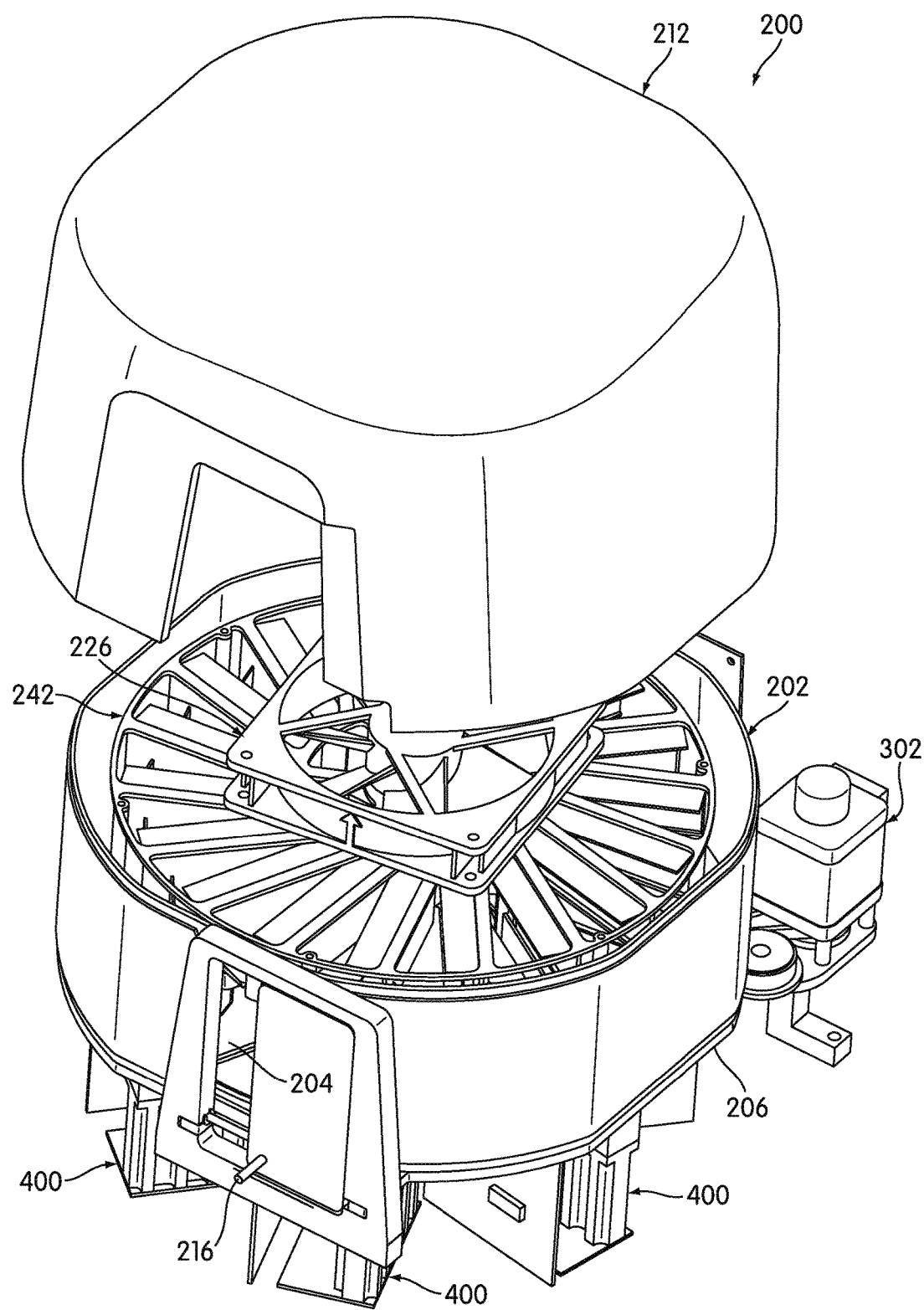
FIG. 3 is an exploded perspective view of an incubator configured to hold a plurality of receptacles while subjecting the reaction receptacles to prescribed temperature conditions and including signal detectors for detecting signals emitted by the contents of the reaction receptacles during an incubation process, according to an embodiment.

FIG. 3 shows an exploded perspective view of incubator 200 according to an embodiment. Incubator 200 can include a housing having an outer wall 202, a bottom wall 206, and a top wall (not shown). Each of outer wall 202, bottom wall 206, and the top wall can be covered by a thermal insulating shroud 212, which is shown lifted off the remainder of incubator 200 in FIG. 3. In some embodiments, the side, bottom and top walls are made of aluminum, and the insulating hood is made from a suitable insulating material, for example, a polyurethane foam. Receptacle carrier 242, for example, a carousel rotatably mounted within the housing, is configured for carrying a plurality of reaction receptacles 162 of MRDs 160. MRDs 160 can be inserted into receptacle carrier 242 and removed from receptacle carrier 242 through a receptacle opening 204 formed in outer wall 202. Receptacle opening 204 is covered by the sliding door 216.

In some embodiments, one or more signal detectors 400 are disposed beneath bottom wall 206 of the incubator housing and are configured to detect signals emitted by the contents of the receptacles 162 of MRDs 160 carried on receptacle carrier 242 within incubator 200. Signal detectors 400, which may comprise fluorometers configured to detect fluorescent signals in some embodiments, are described in further detail below.

Heat may be generated within incubator 200 by any suitable means. For example, in one embodiment, resistive heating elements (not shown) are disposed on the outer wall 202 of the incubator housing. Other suitable heating elements may include, for example, Peltier thermoelectric heating elements. In some embodiments, a controller (e.g., a microprocessor) can control the heating elements to maintain a constant, desired temperature, and incubator 200 may further include one or more temperature sensors configured to generate temperature level signals that are transmitted to the controller.

A circulating fan 226 may be positioned within the incubator housing, for example, atop receptacle carrier 242. In one embodiment, fan 226 is an axial fan, as shown, configured for generating airflow through receptacle carrier 242 and within incubator 200.

Figure 4:
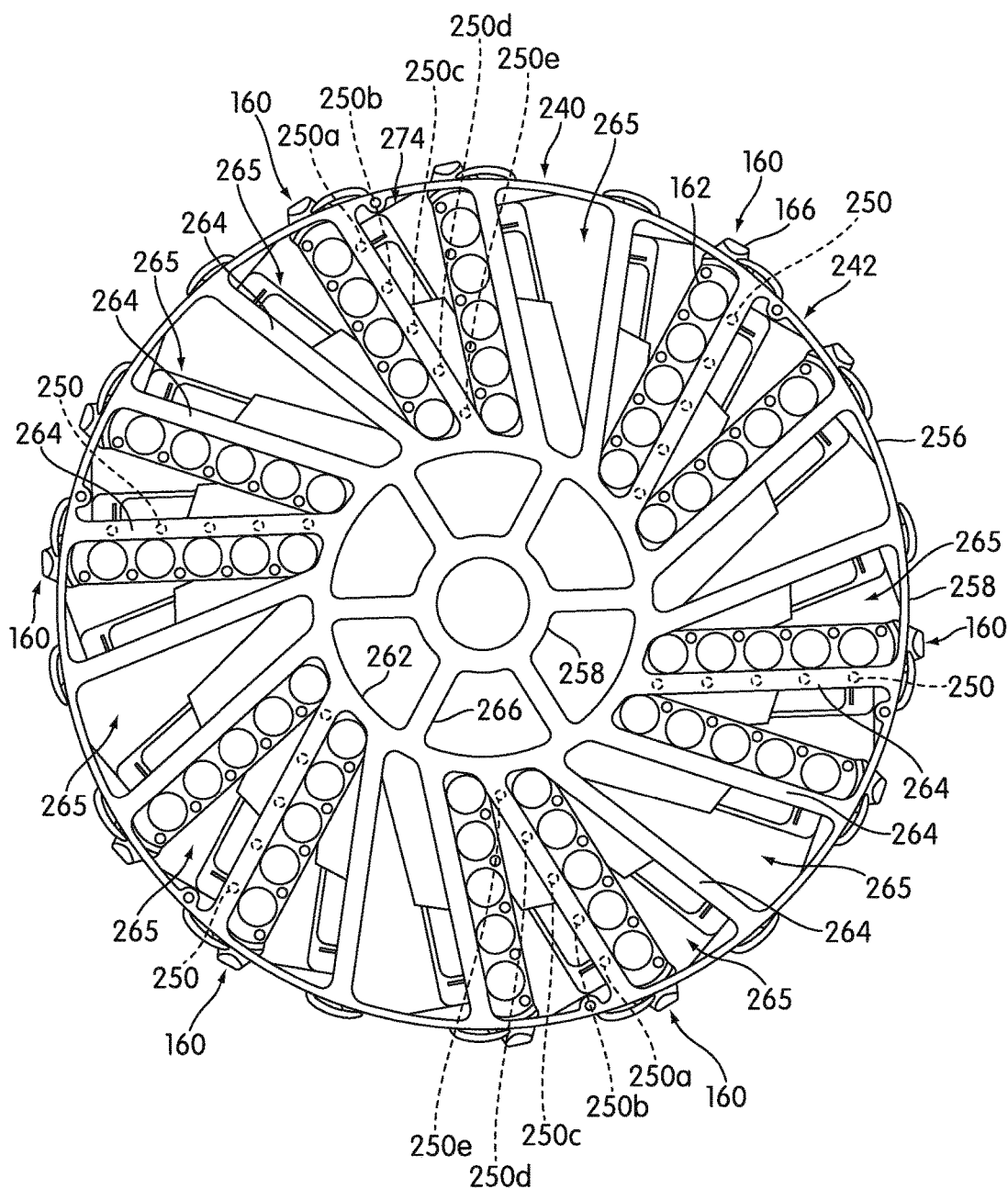
FIG. 4 is a bottom plan view of a receptacle carrier of the incubator, according to an embodiment.

FIG. 4 is a bottom plan view of receptacle carrier 242, according to an embodiment. As shown in FIG. 4, receptacle carrier 242 supports a plurality of MRDs 160. FIG. 5 is a perspective view of a portion of receptacle carrier 242, according to an embodiment, and shows the fan 226 mounted atop the receptacle carrier 242.

In some embodiments, receptacle carrier 242 comprises an upper disk 244 and a lower disk 256. Lower disk 256 can be identical to upper disk 244 in some embodiments. As shown in FIGS. 4 and 5, lower disk 256 includes an inner ring 258, an outer ring 260, and an intermediate ring 262 disposed concentrically between the inner ring 258 and outer ring 260. Inner radial spokes 266 extend between the inner ring 258 and the intermediate ring 262. Outer spokes 264 extend between the intermediate ring 262 and the outer ring 260. In the illustrated embodiment, outer spokes 264 are in a non-radial orientation, meaning that each spoke is configured obliquely with respect to a true-radial orientation relative to the center of lower disk 256. One or more of outer spokes 264 can include one or more surface portions 250 that are made of a non-fluorescent material, for example, surfaces made of aluminum. For example, as shown in FIG. 4, every third spoke 264 can include a plurality of surface portions 250 that are made of a non-fluorescent material, for example, five surface portions 250a-250e. In some embodiments, surface portions 250 can define an opening, or in other embodiments, surface portions 250 can be solid. In some embodiments, the surface portions 250 one a single spoke 264 are linearly aligned. In some embodiments, each surface portion 250 of receptacle carrier 242 is in the same plane of receptacle carrier 242.

In some embodiments, lower disk 256 defines a plurality of openings 265. For example, openings 265 can be collectively defined by intermediate ring 262, outer spokes 264, and outer ring 260. As shown in FIGS. 4 and 5, openings 265 can have a substantially triangular shape. As shown in FIG. 4, lower disk 256 can have eighteen outer spokes 264 and eighteen openings 265 in some embodiments.

As shown in FIG. 5, upper disk 244 can have a similar construction, but only outer ring 248 and outer spokes 252 are visible in FIG. 5. Upper disk 244 can also include an inner ring, an intermediate ring, and inner spokes, all of which are obstructed from view by fan 226 in FIG. 5.

In some embodiments, upper disk 244 and lower disk 256 can be secured relative to one another by a plurality of spacer posts 268 disposed at angular intervals around the perimeters of upper disk 244 and lower disk 256. In some embodiments, spacer posts 268 have a parallel, spaced-apart orientation as shown in FIG. 5. Each spacer post 268 may be secured in place by means of a suitable fastener, for example, a bolt or a screw, extending through a hole in upper disk 244 or lower disk 256 and into an opening (e.g., a threaded opening) formed in each end of each of spacer posts 268.

In some embodiments, receptacle carrier 242 further includes a plurality of receptacle dividers 274 extending between each of outer spokes 264 of lower disk 256 and corresponding outer spokes 252 of upper disk 244. The spaces between adjacently disposed receptacle dividers 274 define receptacle/MRD receiving stations 211, each configured to receive a single MRD 160. As shown in FIG. 4, which is a bottom plan view of a receptacle carrier 242 of incubator 200, each MRD 160 can be carried in a generally vertical orientation with the lower ends of each receptacle 162 exposed at the bottom of receptacle carrier 242 and with the receptacle manipulating structure 166 of each MRD 160 extending radially beyond the outer perimeter of receptacle carrier 242.

Figure 6:
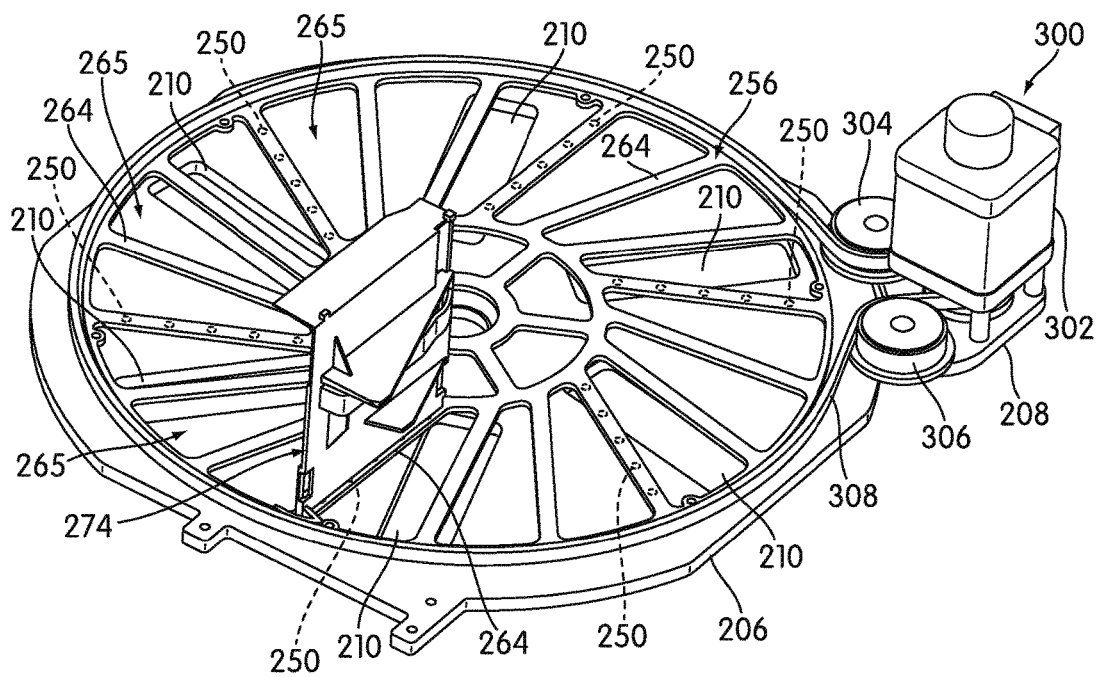
FIG. 6 is a perspective view of a bottom wall of the incubator housing, a portion of the receptacle carrier, and a receptacle carrier drive assembly, according to an embodiment.
Figure 7:
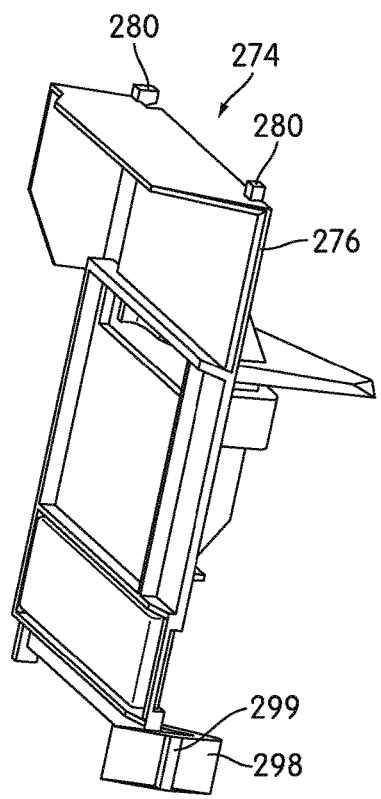
FIG. 7 is a perspective view of a receptacle divider of the receptacle carrier, according to an embodiment.
Figure 8:
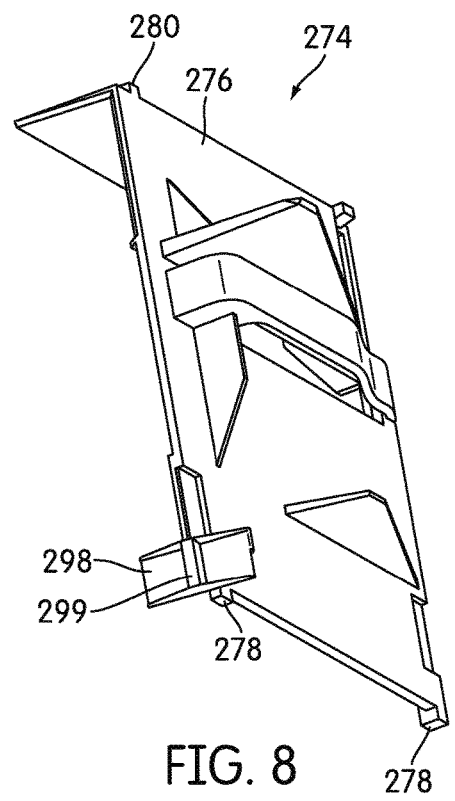
FIG. 8 is a perspective view of the receptacle divider from an opposite side of the divider, according to an embodiment.

FIGS. 6-8 illustrate an embodiment of receptacle dividers 274. Each receptacle divider 274 can be attached to one of outer spokes 264 of lower disk 256, as shown in FIG. 6. In some embodiments, receptacle divider 274 includes a divider wall 276 that is oriented generally vertically when divider 274 is installed between upper disk 244 and lower disk 256.

Divider wall 276 can also include lower positioning posts 278 configured to be inserted into mating openings formed in lower disk 256 (not shown) and upper positioning posts 280 configured to be inserted into mating openings (not shown) formed in upper disk 244. In an embodiment, incubator 200 holds eighteen MRDs 160 at a time, each spaced at 20° increments around the receptacle carrier 242. In other embodiments, incubator 200 is configured to hold more than or less than eighteen MRDs 160 spaced around receptacle carrier 242. For example, in some embodiments, receptacle carrier 242 is only loaded with twelve MRDs 160. In such twelve MRD embodiments, there are empty recesses (e.g., a void or space lacking matter such as components composing receptacle carrier 242) between lower disk 256 and upper disk 244, adjacent a respective opening 265, at six positions, for example, spaced at 60° increments around the receptacle carrier 242. And twelve MRDs 160 can be spaced at 20° increments around the receptacle carrier 242, except for where the six empty recesses are located.

In some embodiments, incubator 200 includes a drive assembly 300 configured to selectively rotate receptacle carrier 242 to a plurality of angular positions. Drive assembly 300 can include a motor 302 mounted on a motor mount portion 208 of bottom wall 206 of the incubator housing. Drive assembly 300 can also include guide wheels 304 and 306, and a drive belt 308. Drive belt 308 is secured around a drive shaft (not shown) of motor 302, around guide wheels 304 and 306, and further over the belt drive supports 298 of the plurality of divider walls 274 mounted between upper disk 244 and lower disk 256 (shown in FIGS. 7 and 8). Each drive belt support 298 can include a vertical rib 299 for engaging teeth (not shown) of drive belt 308. As shown in FIG. 6, which shows a perspective view of bottom wall 206 of the incubator housing, bottom wall 206 of the incubator housing defines a plurality of openings 210. As shown in FIG. 6, openings 210 can be elongated and rectangular in some embodiments. In some embodiments, openings 210 are formed at equal angular intervals about a point corresponding to the axis of rotation of receptacle carrier 242. Openings 210 can be oriented at the same angle at which each MRD 160 will be oriented when carried on receptacle carrier 242, and each opening 210 is configured to receive an upper end of a signal detector 400 extending into incubator 200 for detecting signals emitted by the contents of the MRDs 160 during the incubation process. In some embodiments, motor 302 is a stepper motor that controlled by a controller, for example, microprocessor, for precise control of rotation of receptacle carrier 242. A "home" position sensor (not shown) indicates when receptacle carrier 242 is in a specified rotational position, and motor 302 is provided with an encoder in some embodiments. Accordingly, movement of receptacle carrier 242 can be controlled, e.g., by a microprocessor receiving signals from the home sensor and an encoder coupled to motor 302 to control and monitor the angular movement and positioning of receptacle carrier 242, to sequentially place each MRD 160 on receptacle carrier 242 into a signal detection position above openings 210.

Figure 9:
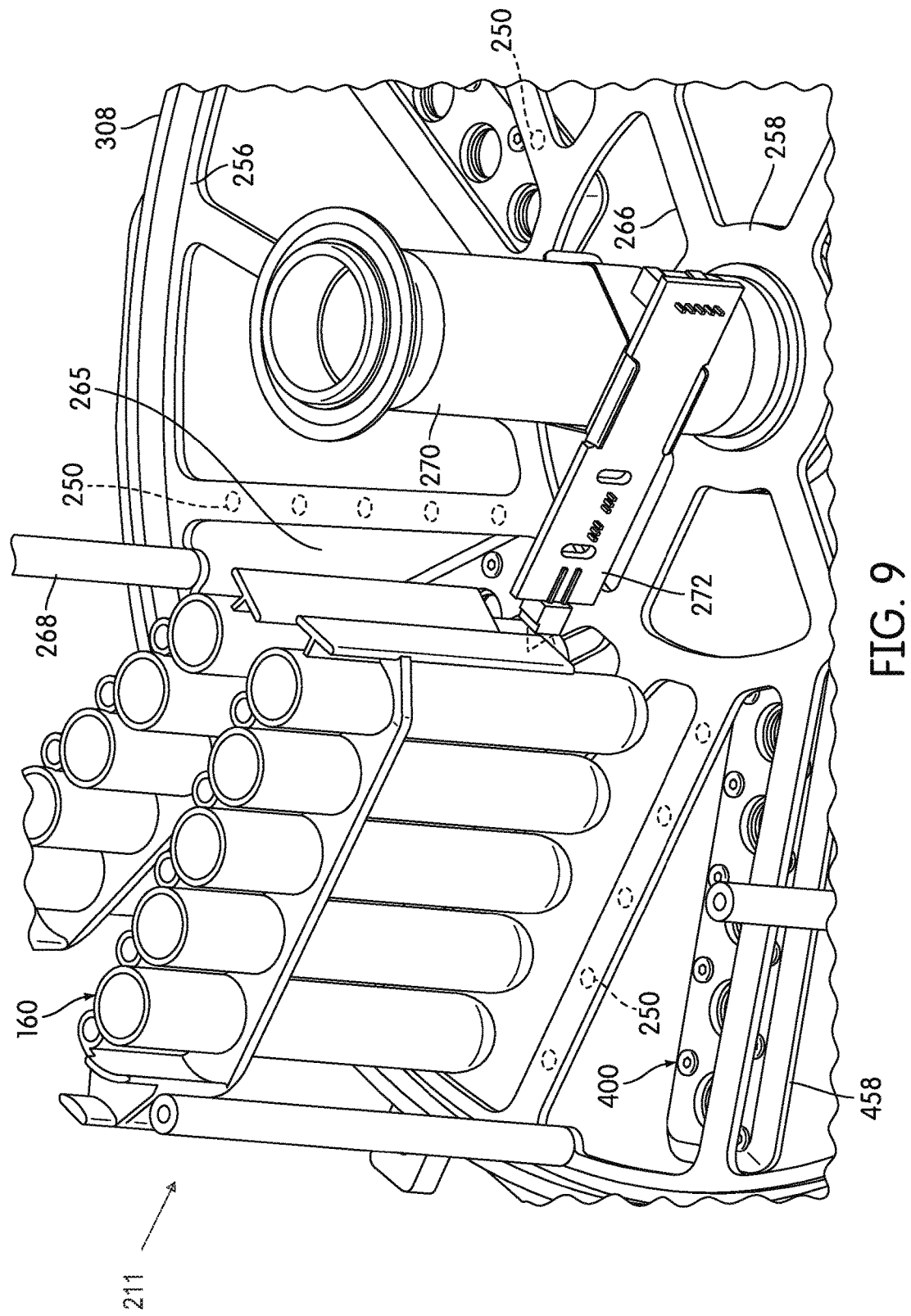
FIG. 9 is a partial perspective view of components of the receptacle carrier of the incubator including a receptacle presence sensor for detecting the presence of reaction receptacles on the receptacle carrier, according to an embodiment.

As shown in FIG. 9, which illustrates a partial perspective view of receptacle carrier 242 according to an embodiment, receptacle carrier 242 can include a center post 270 extending between inner ring 258 of lower disk 256 and the inner ring of upper disk 244 (not shown in FIG. 9). Incubator 200 can also include a receptacle presence sensor 272, which is mounted to center post 270 in some embodiments, configured to detect the presence of an MRD 160 inserted into a receptacle station 211 of receptacle carrier 242. A controller, which controls and monitors the angular position of receptacle carrier 242, also monitors the location of each specific MRD 160, which may be identified by, e.g., a label, such as a machine-readable bar-code or an RFID tag. That is, when an MRD 160, identified via its label or other means, is moved into incubator 200, the angular position of the receptacle station 211 into which that MRD 160 is inserted is determined and tracked to monitor the position of that MRD 160 at all times while the MRD is inside incubator 200.

With reference to FIGS. 9-14, signal detectors 400 can be configured to measure, for example, the concentration of unquenched fluorescent dye molecules within the contents of receptacles 162 of MRDs 160 carried on receptacle carrier 242. The assay performed within each receptacle 162 of each MRD 160 may be designed such that the fluorescent signal increases as the concentration of target is increased by amplification. Signal detector 400 (e.g., a fluorometer) can monitor the amplification process by monitoring the fluorescent signal, for example, the emergence of the fluorescent signal.

Figure 10:
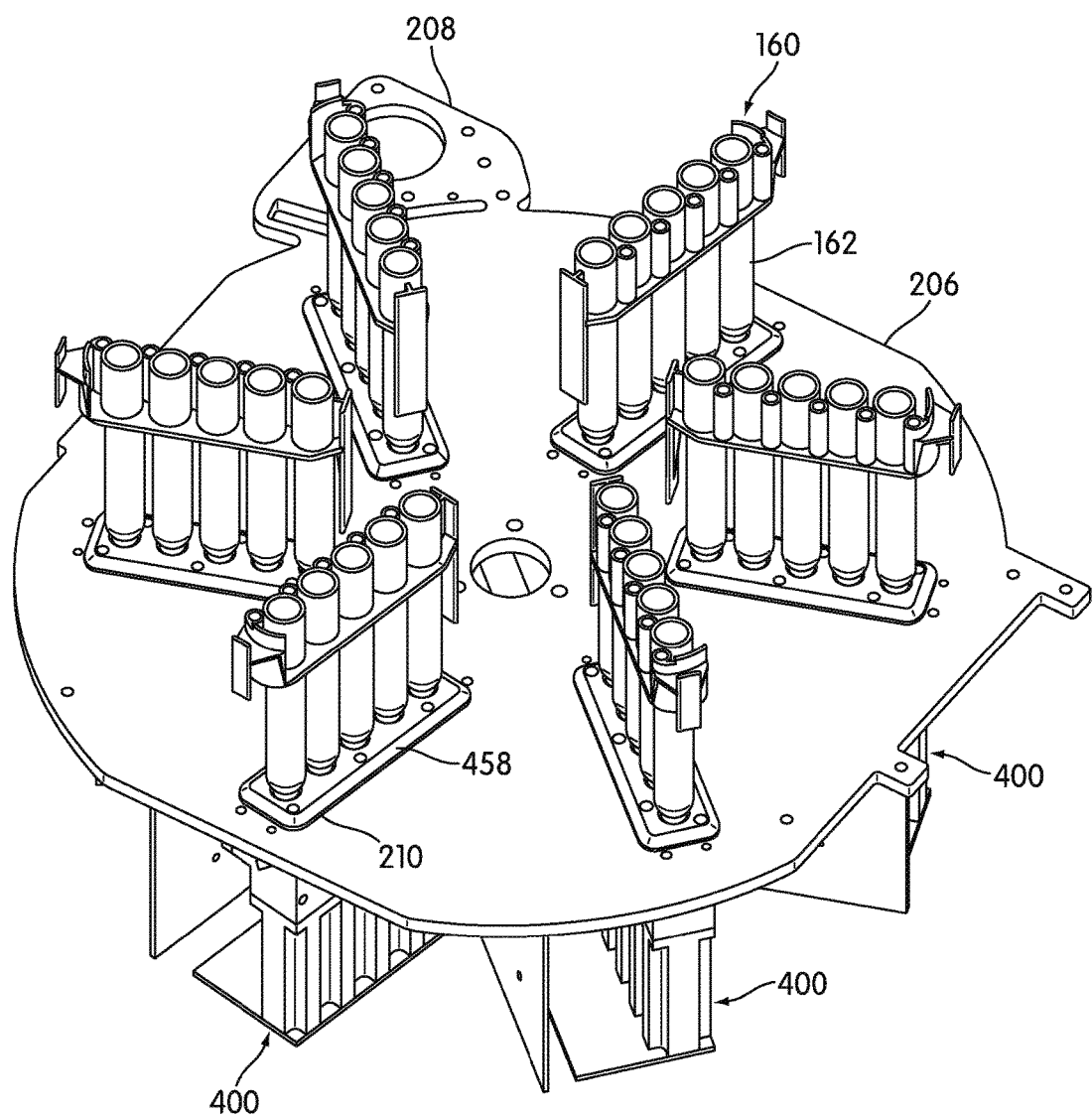
FIG. 10 is a partial perspective view of a portion of the incubator including the incubator floor, signal detectors disposed beneath the incubator floor, and reaction receptacles disposed in signal detecting positions with respect to the signal detectors, according to an embodiment.

An exemplary embodiment of incubator 200 may include between three and six signal detectors 400. As shown in FIG. 10, incubator 200 includes six signal detectors 400. In some embodiments, each detector 400 is designed to measure a particular fluorescent dye (i.e., color). Each signal detector 400 houses a plurality of individual detection channels, for example, five detection channels, that are spaced relative to each other with the same spacing that corresponds with the spacing of receptacles 162 of each MRD 160. Signal detector 400 can have more than or less than five detection channels. In some embodiments, the number of detection channels corresponds to the number of receptacles 162 in each MRD 160.

In some embodiments, each signal detector 400 is mounted to incubator 200 with such an orientation that each detection channel of signal detector 400 can detect a signal emitted by the contents of a respective receptacle 162 of an MRD 160 when receptacle carrier 242 stops at preset angular positions that correspond to the angular positions of signal detectors 400. Therefore, each MRD 160 can be scanned by each signal detector 400 once per revolution of receptacle carrier 242 in some embodiments.

As shown in FIG. 10, which is a partial perspective view of incubator 200 according to an embodiment, incubator 200 includes six signal detectors 400 that are each constructed and arranged to detect signals emitted by the contents of each of the five receptacles 162 of six different MRDs 160 carried within the housing of incubator 200, according to one embodiment. That is, each signal detector 400 is configured to detect a signal emitted by each of the five receptacles 162 of an MRD 160 operatively positioned by receptacle carrier 242 with respect to the signal detector 400. In some embodiments, signal detectors 400 may be of substantially identical constructions, but each may be adapted to detect a signal characteristic of a different measureable or detectable value. For example, each signal detector 400 may be configured to detect fluorescence of a different wavelength (i.e., color), and thus each signal detector 400 may be configured, or tuned, to detect a different fluorescent dye within the contents of receptacle 162. In some embodiments, each signal detector 400 may also be configured to emit light at a different predefined wavelengths or within different ranges of wavelengths. The wavelength of the emitted light from signal detector 400 can correspond to an excitation wavelength window of a fluorescent dye within the contents of receptacle 162.

In some embodiments, a controller, for example, a microprocessor, controls motor 302, which moves receptacle carrier 242, by receiving signals from a home sensor coupled to the receptacle carrier 242, a timer, and an encoder coupled to motor 302 such that the controller controls movement and angular positioning of receptacle carrier 242. In some embodiments, the controller rotates receptacle carrier 242 to move MRD(s) 160 into operative, sensing positions with respect to the signal detector(s) 400 such that MRD(s) 160 are aligned with opening(s) 210 and signal detector(s) 400. The controller can pause rotation of receptacle carrier 242 for a sufficient period of time to permit the signal detector(s) 400 to acquire and process a signal reading from the MRD(s) 160 operatively positioned with respect to signal detector(s) 400, and the controller can index the receptacle carrier 242 to position the next MRD(s) 160 into operative position(s) with respect to the signal detector(s) 400. For example, in some embodiments, during one revolution of receptacle carrier 242, the controller is configured to index receptacle carrier 242 to twelve different angular positions such that twelve MRDs 160 on receptacle carrier 242 are positioned at operative, sensing positions with respect to at least three signal detectors 400.

Figure 11:
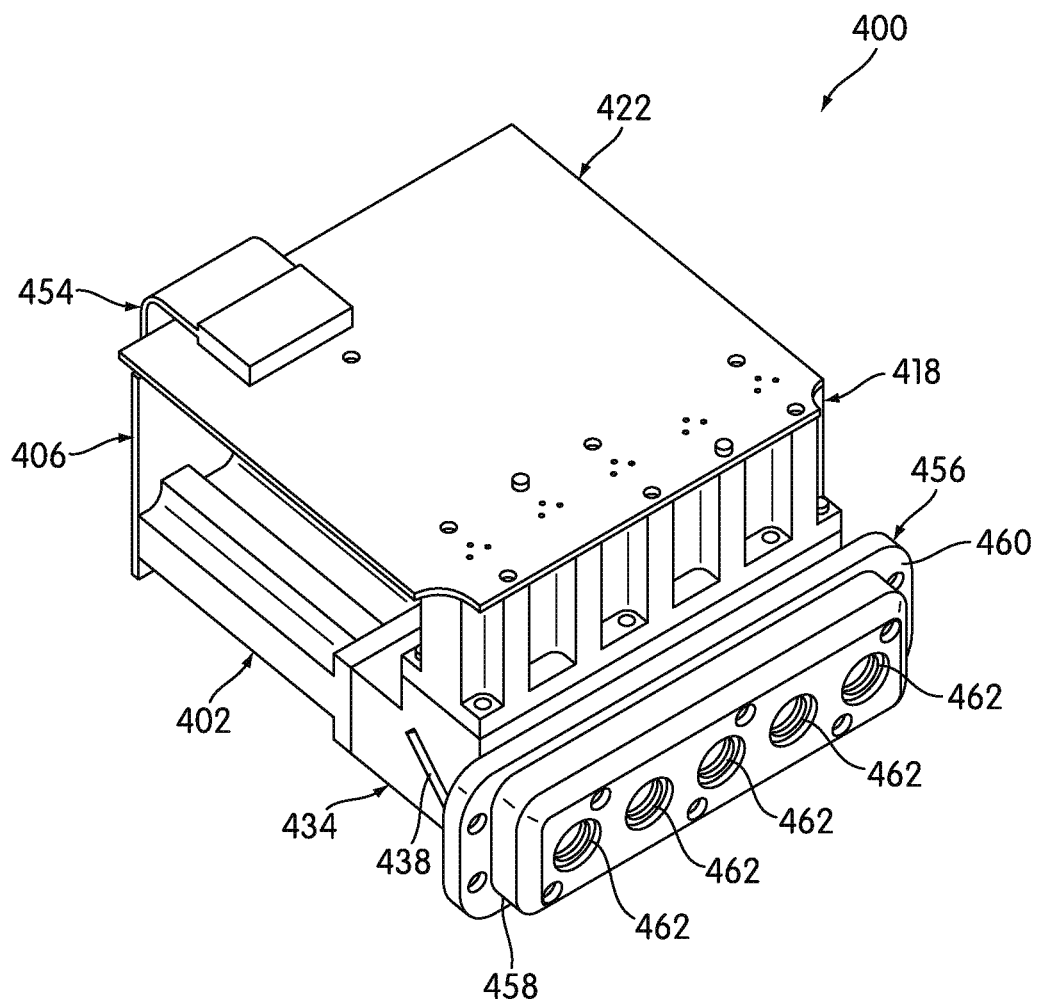
FIG. 11 is a perspective view of a signal detector, according to an embodiment.
Figure 12:
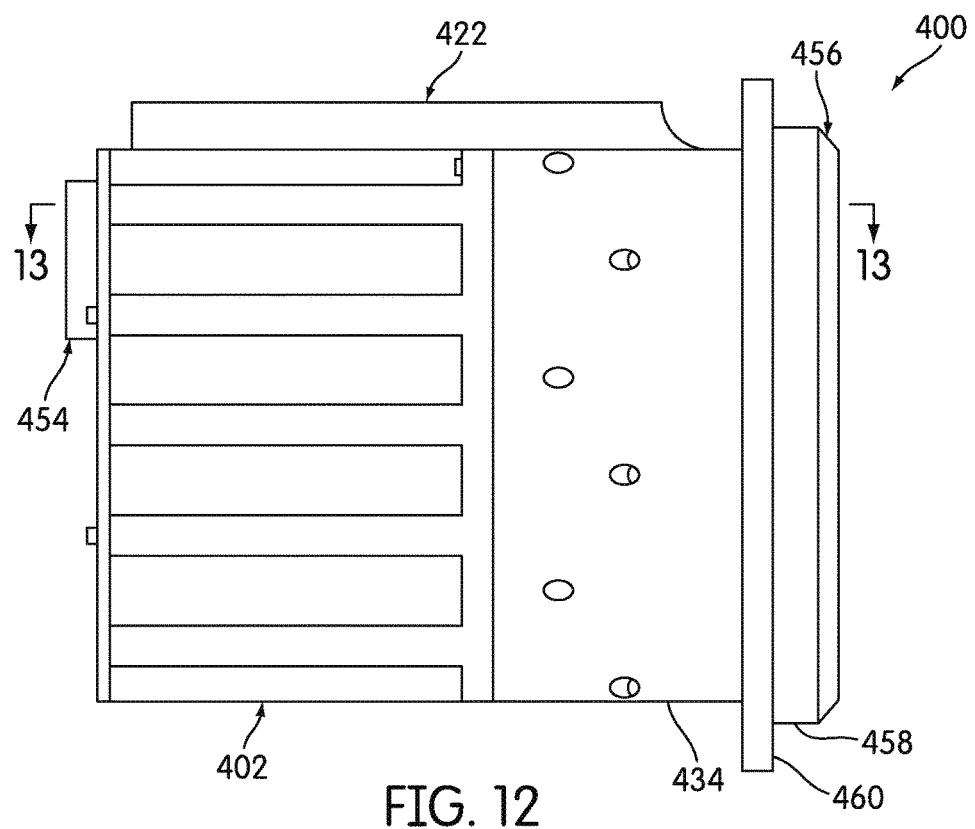
FIG. 12 is a bottom plan view of the signal detector, according to an embodiment.

FIGS. 11-14 illustrate a signal detector 400 according to an embodiment. As shown in FIG. 11, which is a perspective view of signal detector 400, detector 400 includes a housing. In some embodiments, the detector housing includes a detector housing 418 and an excitation housing 402. Detector housing 418 and excitation housing 402 can be connected at a right angle with respect to each other by an optics housing 434. In some embodiments, optics housing 434 encloses a lens and a filter. An interface cap 456 is attached to optics housing 438. Each of the housing components 402, 418, and 434 may be made from, for example, machined aluminum and secured to one another by suitable fasteners, for example, bolts or screws. In some embodiments, each of the housing components 402, 418 and 434 is anodized. In some embodiments, interface cap 456 is machined from non-thermally conductive material, such as Delrin®, so as to minimize thermal conduction between incubator 200 and detector 400.

In some embodiments, detector 400 includes an excitation printed circuit board ("PCB") 406 that is connected to an end of excitation housing 402, and a detector PCB 422 that is connected to an end of detector housing 418. Exemplary excitation and detector circuitry disposed on excitation PCB 406 and detector PCB 422, respectively, are described below. A flexible cable 454 connects excitation PCB 406 with detector PCB 422.

In some embodiments, interface cap 456 includes a rim flange 460 surrounding the periphery of interface cap 456 and a dome portion 458 projecting above rim flange 460. As shown, for example, in FIG. 10, dome portion 458 of interface cap 456 extends into opening 210 formed in bottom wall 206 of incubator 200, and rim flange 460 abuts the bottom surface of bottom wall 206 surrounding opening 210 so as to provide a light-tight seal between interface cap 456 and bottom wall 206. A gasket material may be provided between rim flange 460 and bottom wall 206 to further enhance the light-tight seal. Five detection openings 462 are provided in interface cap 456 in some embodiments.

Figure 13:
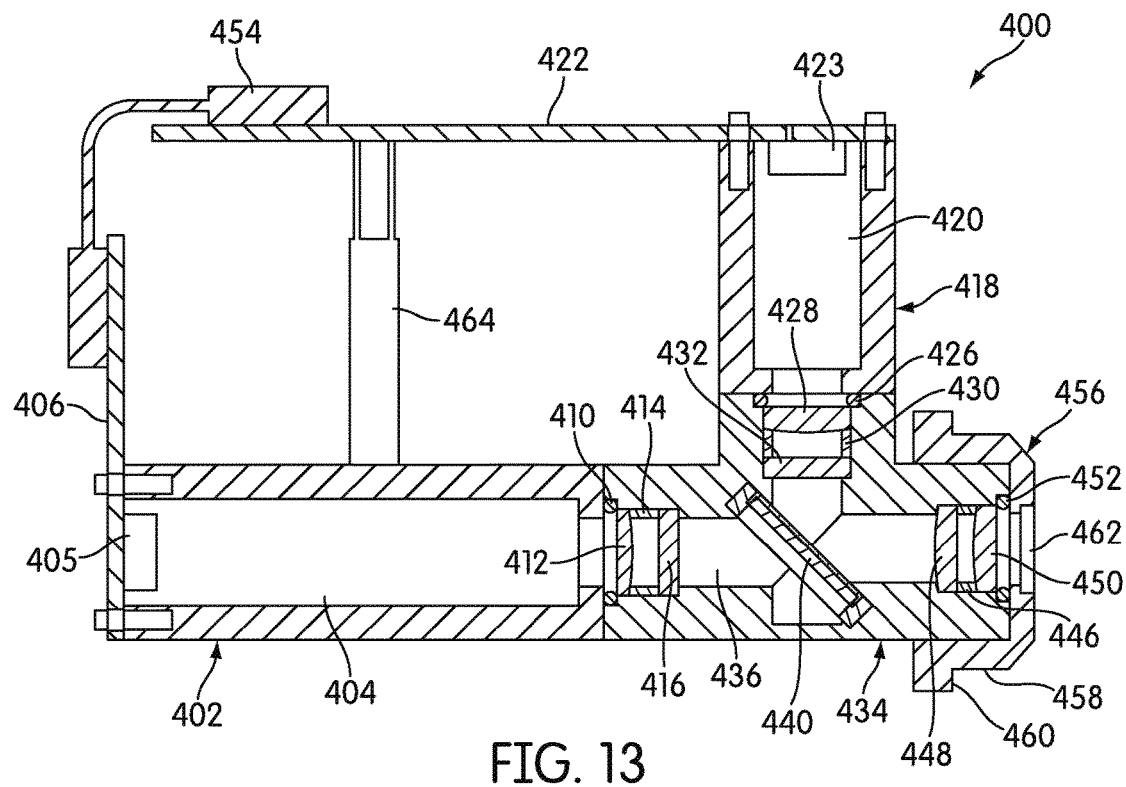
FIG. 13 is a side cross-sectional view of the signal detector taken along the line 13-13 in FIG. 12, according to an embodiment.
Figure 14:
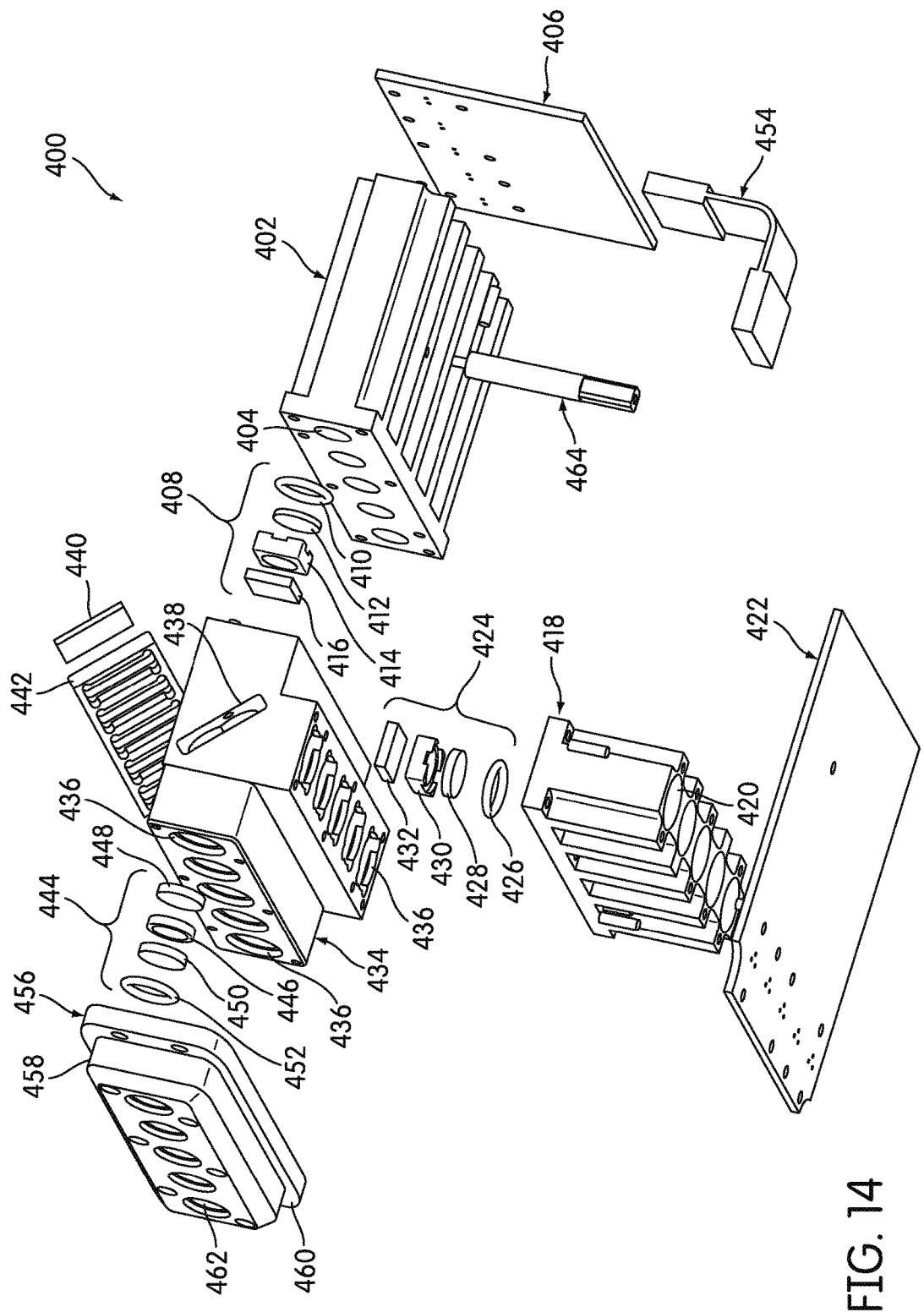
FIG. 14 is an exploded perspective view of the signal detector, according to an embodiment.

As shown in FIGS. 13 and 14, which show a side cross-sectional view and an exploded perspective view, respectively, of signal detector 400 according to an embodiment, excitation housing 402 can include five detection channels each including an excitation channel 404 and an emission channel 420. Each excitation channel 404 can have an excitation light source 405, such as a light-emitting diode ("LED") coupled to excitation PCB 406, located at the end of each excitation channel 404. Similarly, detector housing 418 can include five emission channels 420 each having a sensor 423, for example, an optical signal detector sensor such as a photodiode, coupled to detector PCB 422. A standoff 464 is mounted between excitation housing 402 and detector PCB 422 at a distance from detector housing 418 to provide additional stability for detector PCB 422.

In some embodiments, each individual detection channel of each signal detector 400 defines two optical paths by excitation optics and emission optics disposed, at least partially, within the excitation and emission channels, respectively. In some embodiments, the excitation optical path begins with light source 405, for example, an LED, that generates light. And an excitation lens collimates the generated light. An excitation filter then filters the collimated light. The filtered light passes upward through a beam splitter and is focused onto a receptacle 162 by one or more objective lenses. The objective lenses are between receptacle 162 and the beam splitter. The emission optical path originates from the light emitted by the contents of receptacle 162, and the objective lenses collimates the light as it passes towards the beam splitter. The beam splitter then reflects the emitted light towards emission channel 420. Within emission channel 420, after being filtered through an emission filter, the light is focused by an emission lens onto sensor 423, such as a photodetector.

In some embodiments, the various optical elements of detector 400 are located in optics housing 434. For each excitation channel 404 of excitation housing 402, optics housing 434 contains excitation optics 408 (see, e.g., FIG. 14) in some embodiments. For each emission channel 420 of detector housing 418, optics housing 434 contains emission optics 424 (see, e.g., FIG. 14) in some embodiments. And for each detector opening 462 of interface cap 456, optics housing 434 contains input/output optics 444 (see, e.g., FIG. 14) in some embodiments. Excitation optics 408, emission optics 424, and input/output optics 444 can be disposed within optics channels 436 formed within optics housing 434.

In some embodiments, excitation optics 408 are an optical focus and filter assembly that includes an O-ring 10, an excitation lens 412, a lens holder 414, and an excitation filter 416. O-ring 410 provides a light-tight seal between excitation housing 402 and optics housing 434. Excitation filter 416 is configured to pass excitation light from light source 405 having a desired excitation characteristic (e.g., wavelength) from within excitation channel 404.

In some embodiments, emission optics 424 is an optical focus and filter assembly that includes an O-ring 426, an emission lens 428, a lens holder 430, and an emission filter 432. O-ring 426 provides a light-tight seal between detector housing 418 and optics housing 434. Emission filter 432 can be configured to transmit only a portion of a signal emitted by the contents of a reaction receptacle 162 to sensor 423 within the emission channel 420 that has a desired signal characteristic (e.g., wavelength).

In some embodiments, input/output optics 444 include an O-ring 452, a first objective lens 450, a second objective lens 448, and a spacer ring 446 disposed between first and second objective lenses 450 and 448. O-ring 452 provides a light-tight seal between interface cap 456 and optics housing 434.

Signal detector 400 can include dichroic beam-splitters 440 in some embodiments. For example, dichroic beam-splitters 440 can be held within a beam-splitter frame 442 that is inserted into a beam-splitter opening 438 of optics housing 434. A beam-splitter 440 is provided for each excitation channel 404 and corresponding emission channel 420. Beam-splitter 440 is configured to pass excitation light having a desired signal characteristic (e.g., a prescribed excitation wavelength) in a straight optic path from excitation channel 404 and to deflect emission light having a prescribed detection wavelength from the contents of a receptacle 162 toward detection channel 420.

Figure 19:
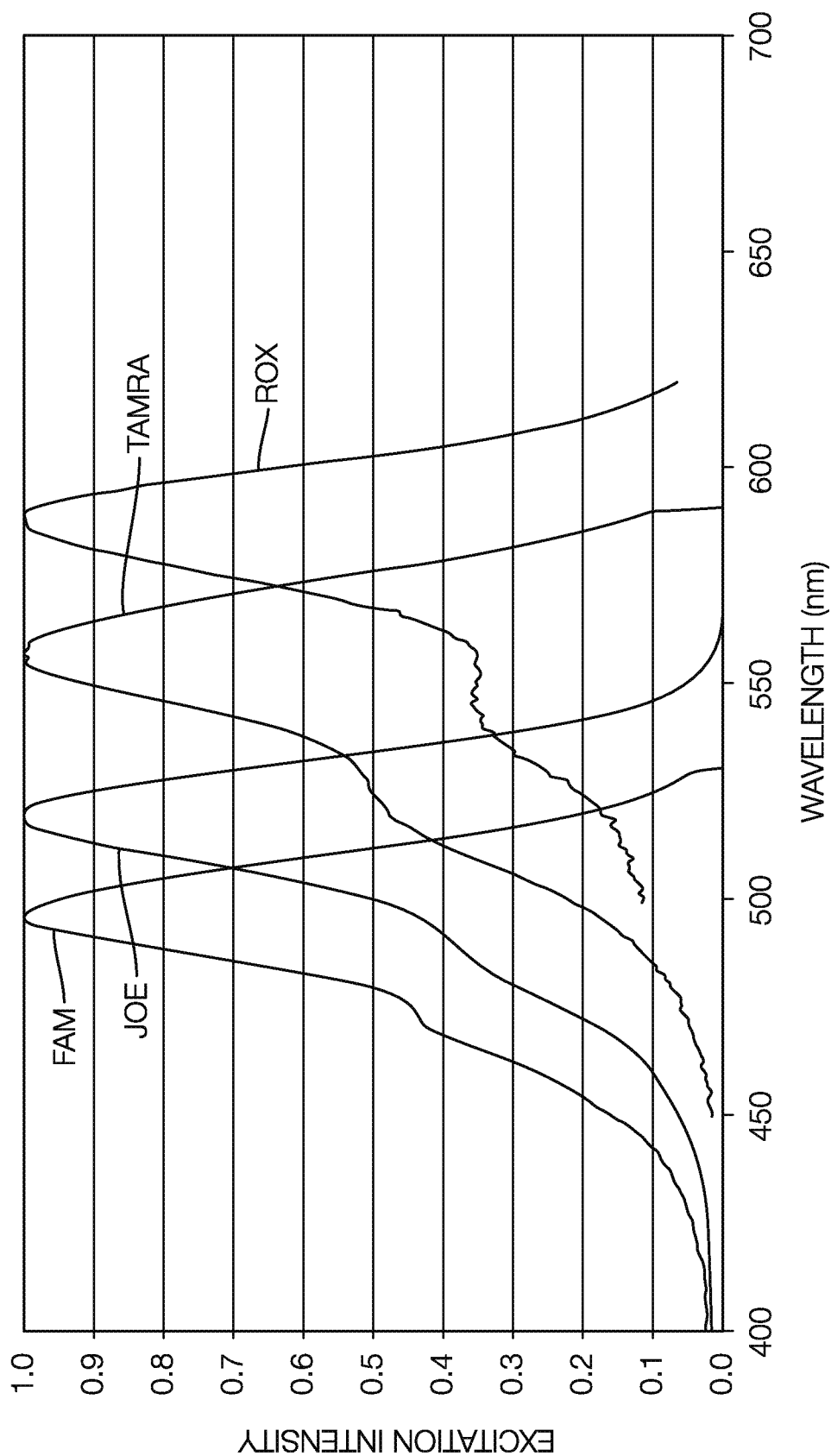
FIG. 19 is a graph showing excitation spectra of exemplary amplification detection dyes, according to an embodiment.
Figure 20:
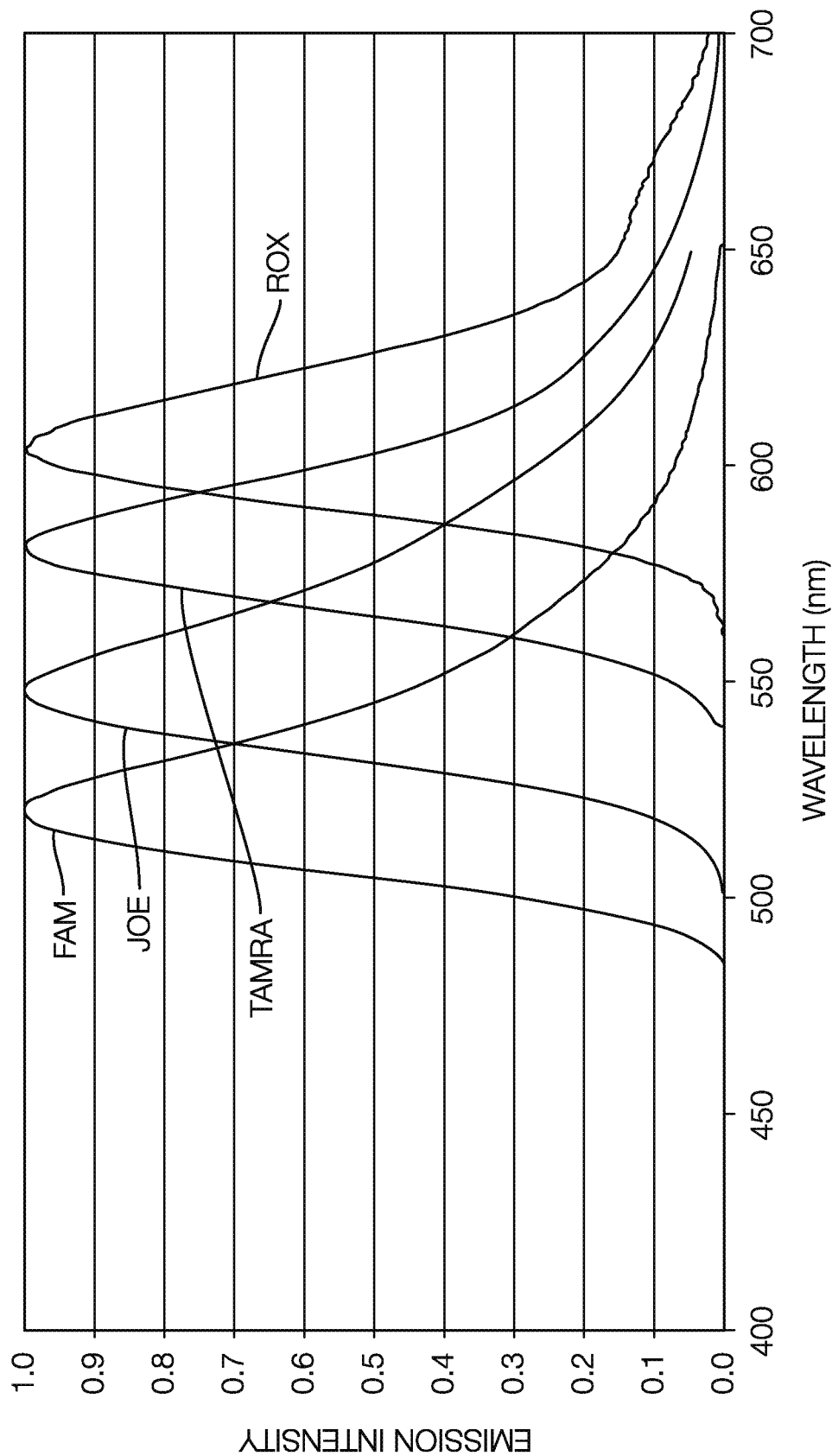
FIG. 20 is a graph showing emission spectra of exemplary amplification detection dyes, according to an embodiment.
Figure 21:
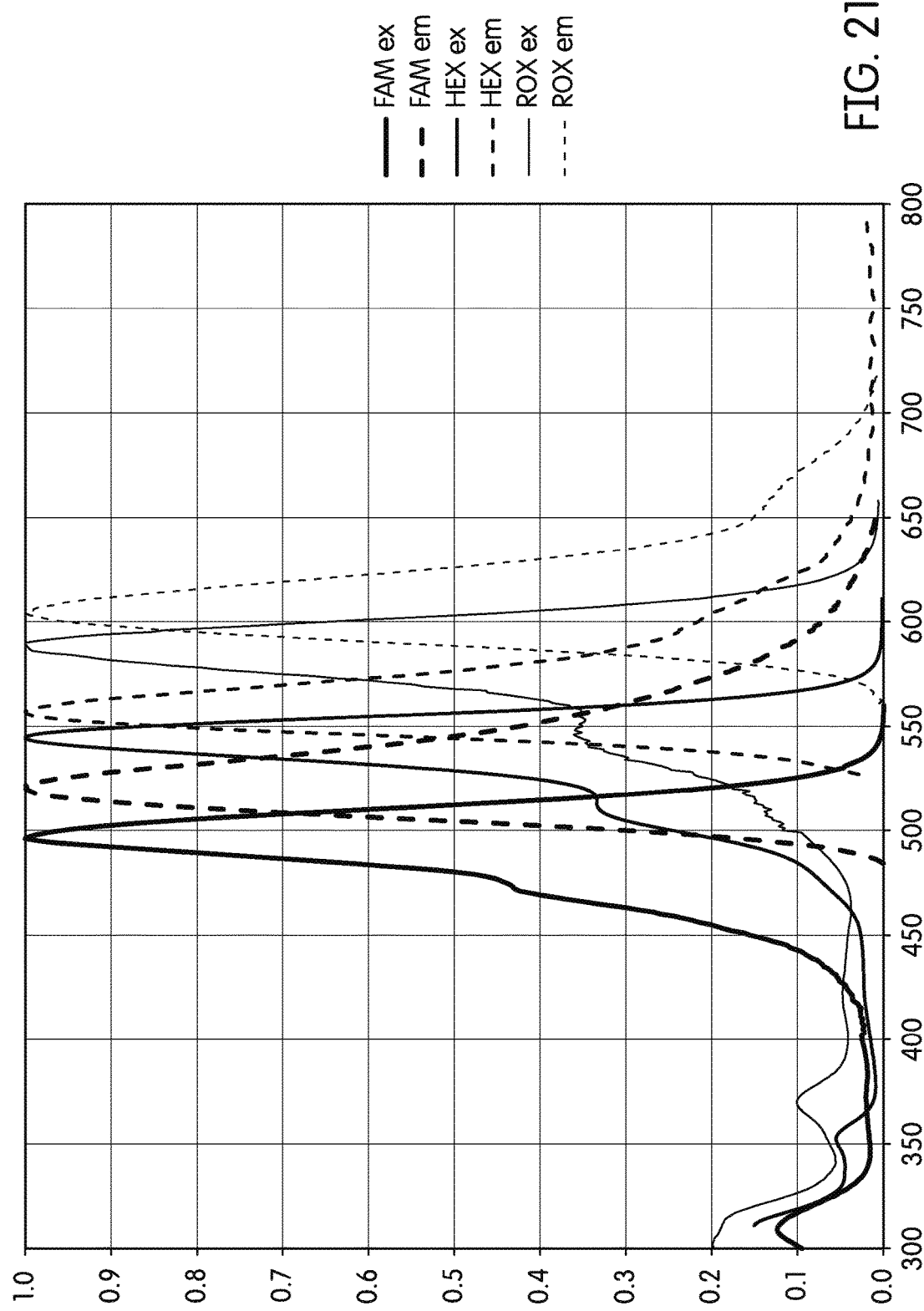
FIG. 21 is a graph showing excitation and emission fluorescence spectra for FAM, HEX, and ROX dyes, according to an embodiment.

In one embodiment, signal detector 400 comprises a fluorometer configured to excite a fluorescent dye of a specific wavelength (i.e., color) by directing an optical excitation signal of a specified, associated excitation wavelength at a receptacle 162 containing a sample with which the fluorescent dye is mixed. The fluorometer is also configured to detect an emission signal having a wavelength corresponding to the wavelength (i.e., color) of the specific dye. Different fluorescent dyes are excited at different wavelengths. In some multiplex embodiments, suitable dyes include rhodamine dyes (e.g., tetramethyl-6-rhodamine ("TAMRA") and tetrapropano-6-carboxyrhodamine ("ROX")) and fluorescein dyes (e.g., 6-carboxyfluorescein ("FAM")) each in combination with a DABCYL quencher. In some embodiments, other suitable dyes include 5'-hexachlorofluorescein phosphoramidite ("HEX"), and 2',7'-dimethoxy-4',5'-dichloro-6-carboxyfluorescein ("JOE"). The normalized excitation spectra of FAM, JOE, TAMRA, and ROX dyes are shown in FIG. 19. FIG. 20 shows the normalized emission spectra of the FAM, JOE, TAMRA, and ROX dyes. Because the dyes are excited at different wavelengths, each signal detector 400 can be tailored to emit an excitation light at or near the desired excitation wavelength (i.e., color) for the particular dye that the fluorometer is intended to detect. Accordingly, component selection for the detector/fluorometer will, in many instances, be governed by the particular dye for which signal detector 400 is intended. For example, the particular light source 405 (e.g., the particular LED) used will depend on the dye for which the fluorometer is intended to detect. FIG. 21 shows normalized excitation wavelengths versus normalized emission fluorescence wavelengths for FAM, HEX, and ROX dyes. As shown in FIG. 21, the HEX excitation wavelength band partially overlaps with FAM emission wavelength band, and the ROX excitation wavelength band partially overlaps with HEX emission wavelength band. See also Table 1 below.

In some embodiments, detectors 400 are identical in design and components, with the exception that some components are dye-specific. The components that are dye-specific include, for example, light source 405, excitation filter 416, emission filter 432, and beam splitter 440.

The following table provides exemplary specifications for a selection of filters for different types of dyes:

Filter Specifications

TABLE 1

| Description | Center Wavelength (nm) | Bandwidth (nm) | Dimensions (mm) | Thickness |
|---|---|---|---|---|
| FAM Excite Filter | 460 | 60 | 8.9 × 8.9 square | 2 |
| FAM Emission Filter | 525 | 30 | 8.9 × 8.9 square | 2 |
| FAM Short Wave Pass Dichroic | | | 10 × 14.8 rectangular | 1.05 |
| HEX Excite Filter | 535 | 22 | 8.9 × 8.9 square | 2 |
| HEX Emission Filter | 567 | 15 | 8.9 × 8.9 square | 2 |
| HEX Short Wave Pass Dichroic | | | 10 × 14.8 rectangular | 1.05 |
| ROX Excite Filter | 585 | 29 | 8.9 × 8.9 square | 2 |
| ROX Emission Filter | 632 | 22 | 8.9 × 8.9 square | 2 |
| ROX Short Wave Pass Dichroic | | | 10 × 14.8 rectangular | 1.05 |

The following table provides exemplary specifications for a selection of lenses for different types of dyes:

Lens and O-Ring Specifications

TABLE 2

Dye = FAM, HEX, ROX

| Part No. | Description | Vendor |
| --- | --- | --- |
| NT47-475 | Emission Lens | Edmund Optics, Inc. (Barrington, NJ) |
| NT47-477 | Excitation Lens | Edmund Optics, Inc. (Barrington, NJ) |
| NT47-476 | Objective Lens | Edmund Optics, Inc. (Barrington, NJ) |
| 94115K478 | O-ring | McMaster-Carr (Elmhurst, IL) |

Table 3 shows provides exemplary specifications for blue, green, and amber LEDs:
LED Specifications

TABLE 3

| Characteristic | Blue | Green | Amber |
| --- | --- | --- | --- |
| Chip Size | 24 mil | 11 mil | 25 mil |
| Dominant Wavelength | 462 nm | 533 nm | 590 nm |
| Radiant Flux | 4 mW | 2 mW | 1.2 mW |
| Max DC forward current | 200 mA | 50 mA | 150 mA |

In the illustrated embodiment of detector 400, beam splitter 440 passes the excitation light and reflects the emission light. Since the excitation channel 404 is longer than the emission channel 420, this arrangement provides a narrow profile for the housing of signal detector 400, thereby maximizing the number of detectors 400 that can be positioned at angular intervals beneath incubator 200, as shown in FIG. 10. Spatial limitations and preferences may be accounted for in designing the excitation and emission channels, which can be interchanged from the format depicted in FIG. 10. In such an alternative embodiment, a beam splitter that reflects the excitation light and passes the emission light could be used.

Figure 22:
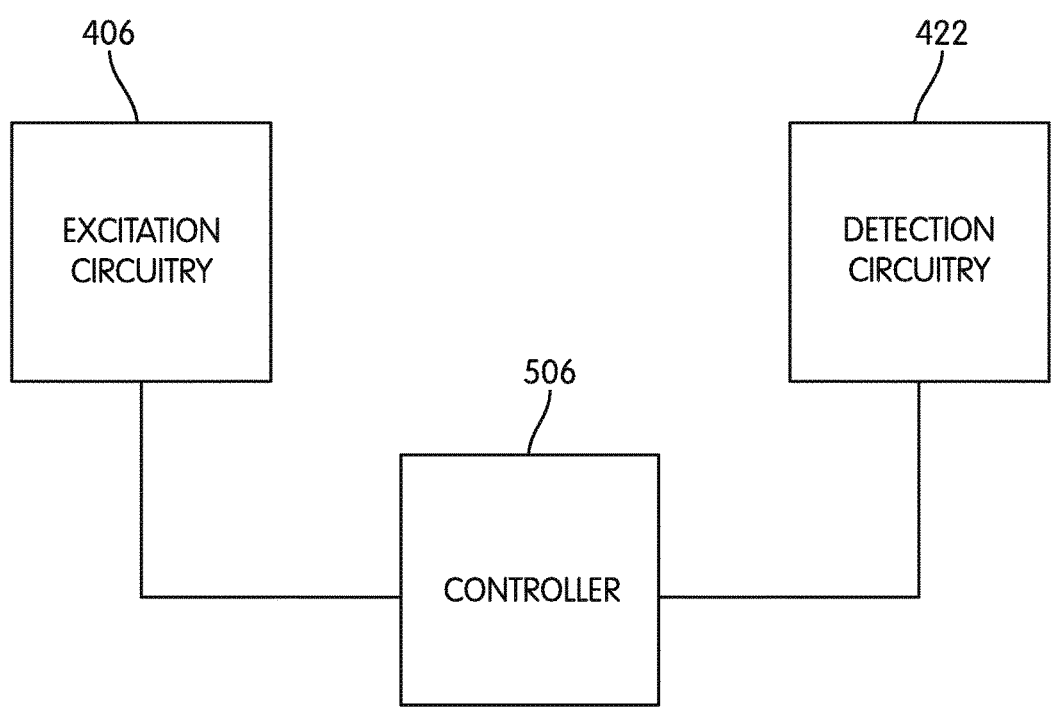
FIG. 22 is a block diagram schematically illustrating excitation and detection architecture, according to an embodiment.

The data acquisition system and process for acquiring, storing, and processing signal data emitted by the contents of the MRDs 160 can be described at a high level with reference to FIG. 22. In some embodiments, the data acquisition system and process include three components: excitation branch 406, detection branch 422, and control branch 506. The excitation branch 406, which can include circuitry such as excitation PCB 406, generates a power signal to control light source 405 (e.g., an LED) to generate an excitation light signal. The detection branch 422, which can include circuitry such as detector PCB 422, converts photons of light that impinge on sensor 423 (e.g., a photodiode) to a current. The control branch 506, which can include a controller such as a microprocessor, drives and controls the excitation circuitry 406 and processes the emission data generated by detection circuitry 422.

Figure 23:
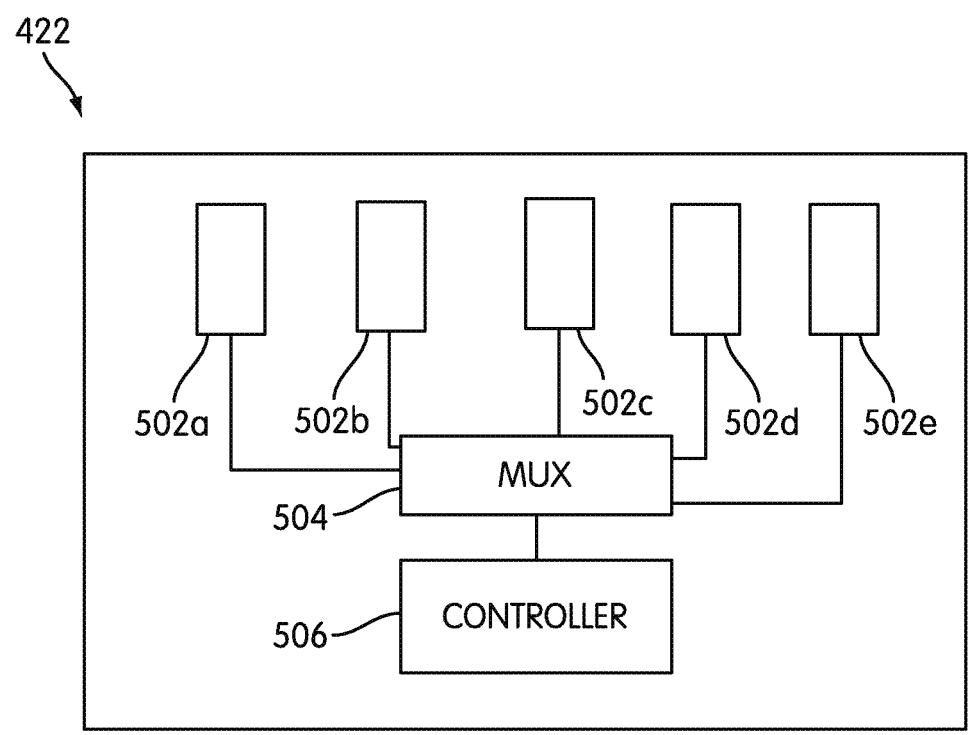
FIG. 23 is a block diagram schematically illustrating an arrangement of detection circuitry, according to an embodiment.

FIG. 23 depicts a logical block diagram of detection circuitry on detector PCB 422 according to an embodiment. The detection circuitry on detector PCB 422 can include detector circuits 502a-502e, which are configured to detect fluorescent light and to convert the detected light to a voltage signal that can be processed by the controller 506. The output from detector circuits 502a-502e can be connected to controller 506 either directly or through a multiplexer 504, as shown in FIG. 23.

Figure 24:
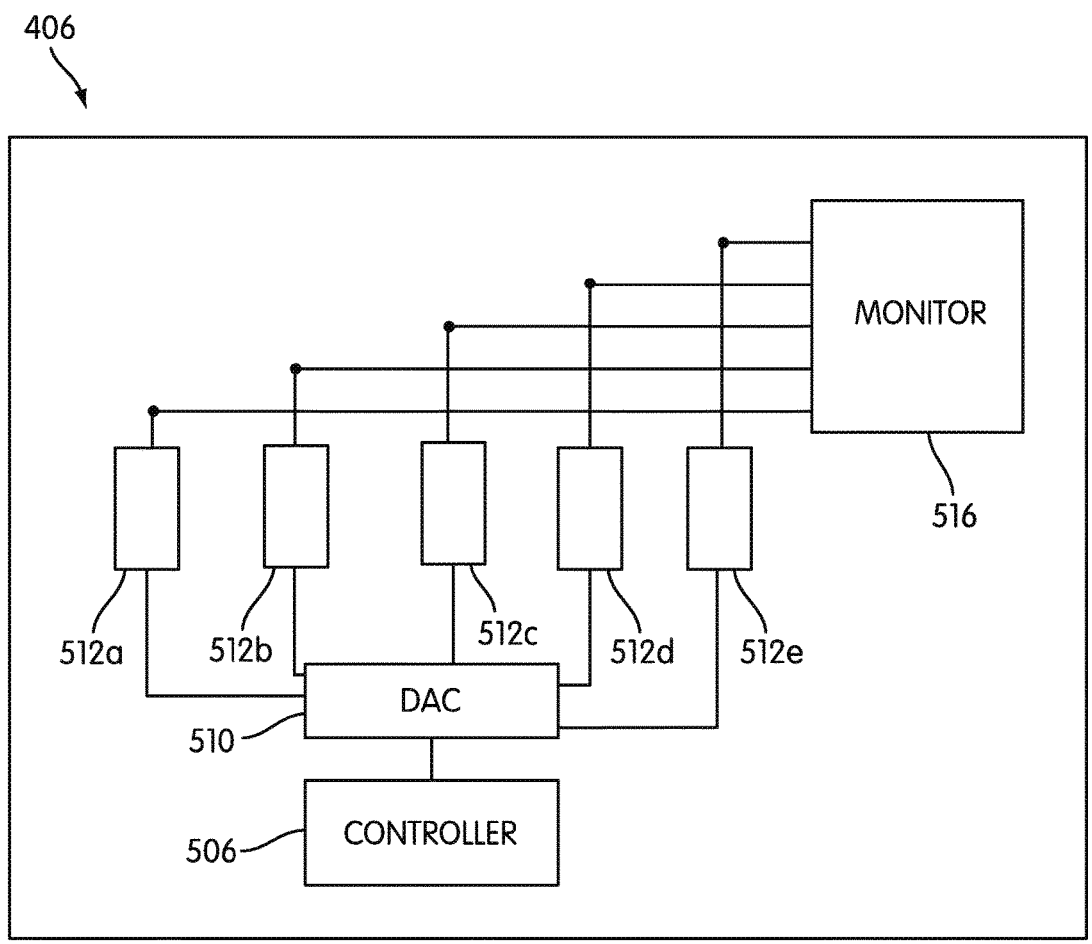
FIG. 24 is a block diagram schematically illustrating an arrangement of excitation circuitry, according to an embodiment.

FIG. 24 depicts a logical block diagram of excitation circuitry on excitation PCB 406 according to an embodiment. The excitation circuitry can include controller 506 and a digital to analog converter (DAC) 510. The excitation circuitry on excitation PCB 406 can also include excitation circuits 512a-512e for driving each light source 405 of each excitation channel 404. Excitation circuits 512a-512e are driven by a DAC controlled current source in some embodiments. The current source is a voltage to current amplifier that controls the current flowing through light source 405.

In some embodiments, the excitation circuitry on excitation PCB 406 includes a monitor 516 connected to excitation circuits 512a-512e to facilitate process control of the excitation voltage. Checking the voltage across light source 405 and the current through light source 405 provides an indication of whether light source 405 is functioning correctly. This diagnostic capability can be used in a variety of ways. For example, light source 405 could be checked at power-on, during a self-test, so when the fluorometer powers up, the fluorometer could put a known current through light source 405, and if the forward voltage of light source 405 is in an expected range, then the system would pass the self-test. These forward voltage values could also be checked during an assay to monitor correct functioning of light source 405.

Figure 25:
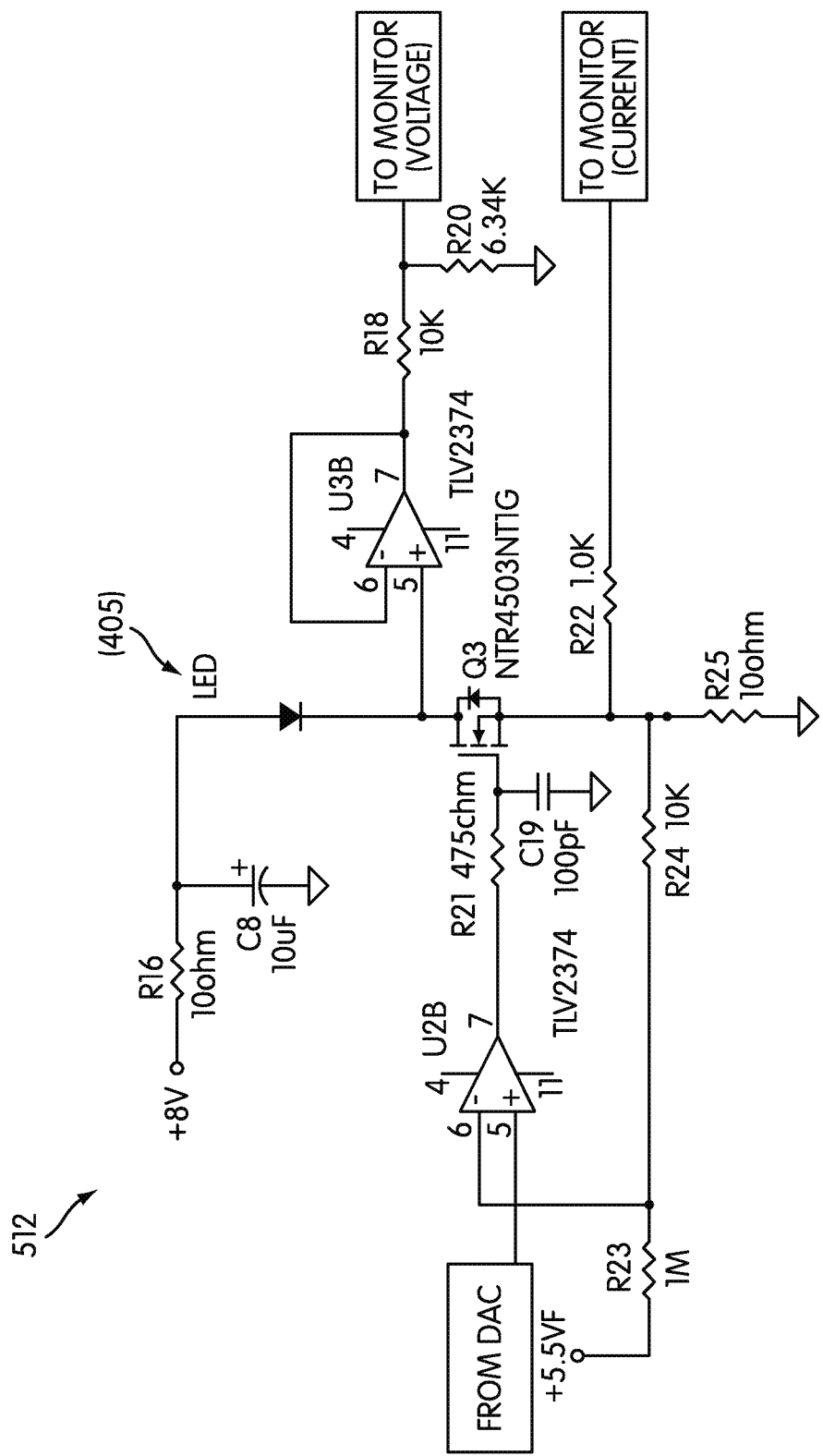
FIG. 25 is a circuit diagram illustrating a fluorometer excitation circuit, according to an embodiment.

In some embodiments, each light source 405 in circuits 512a-512e can be driven by a DAC controlled current source, as shown in FIG. 25, which is a circuit diagram illustrating an exemplary fluorometer excitation circuit. The current source can be a voltage to current amplifier that controls the current flowing through light source 405.

In addition to driving a computer controlled current waveform through light source 405 (e.g., an LED), the current source shown in FIG. 25 allows for process control based on current and voltage of light source 405. The output of the circuit formed by U3B is a monitor of the voltage across light source 405 and can be digitized by monitor 516 using an analog-to-digital (A/D) converter. Similarly the output of R22 (the side away from transistor Q3) can be used to monitor the current passing through light source 405 and similarly digitized by an A/D converter located in monitor 516. The current through light source 405 can be monitored for diagnostic purposes, as described above.

Figure 26A:
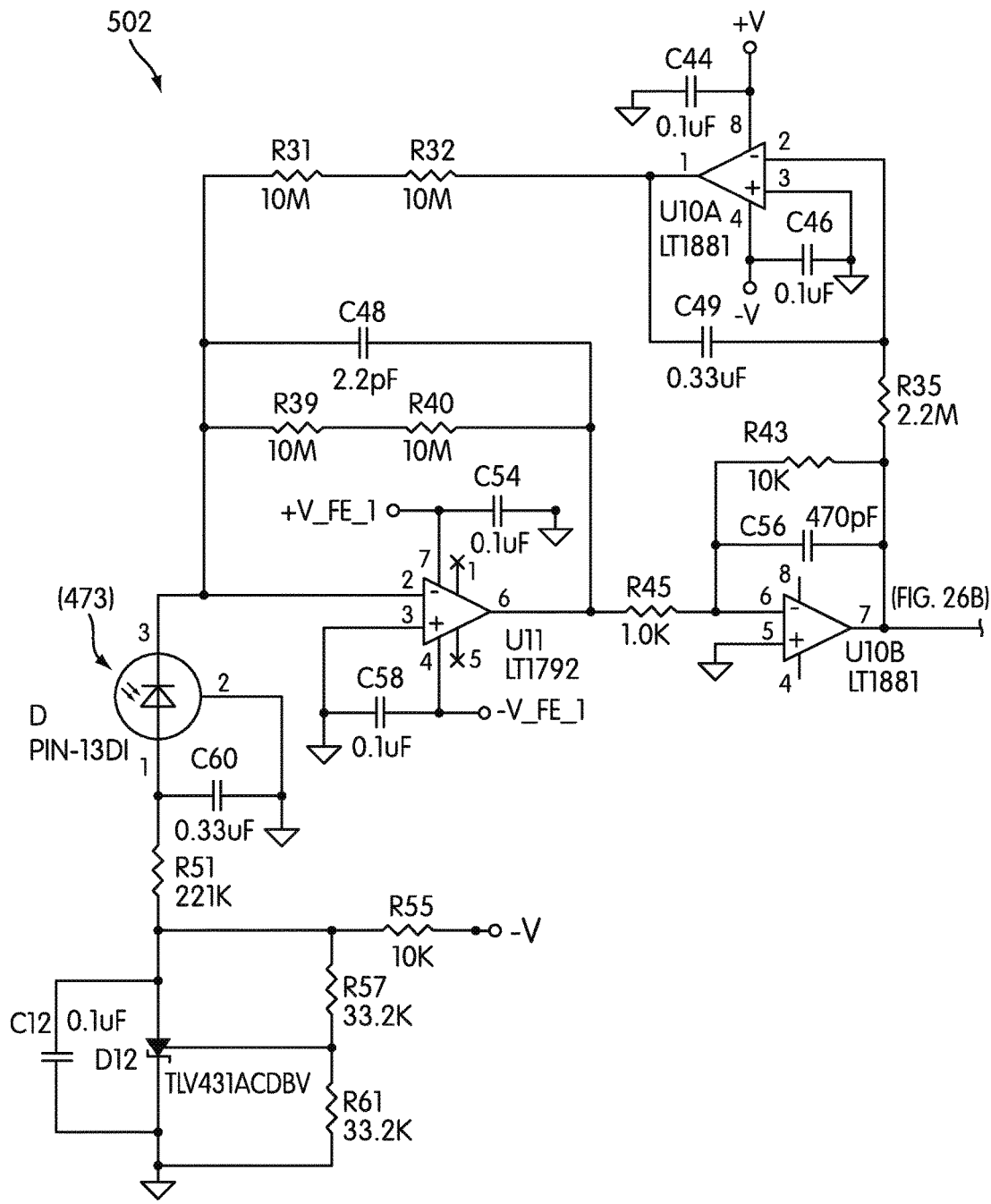
FIGS. 26A and 26B are two parts of a circuit diagram illustrating a fluorometer detection circuit, according to an embodiment.
Figure 26B:
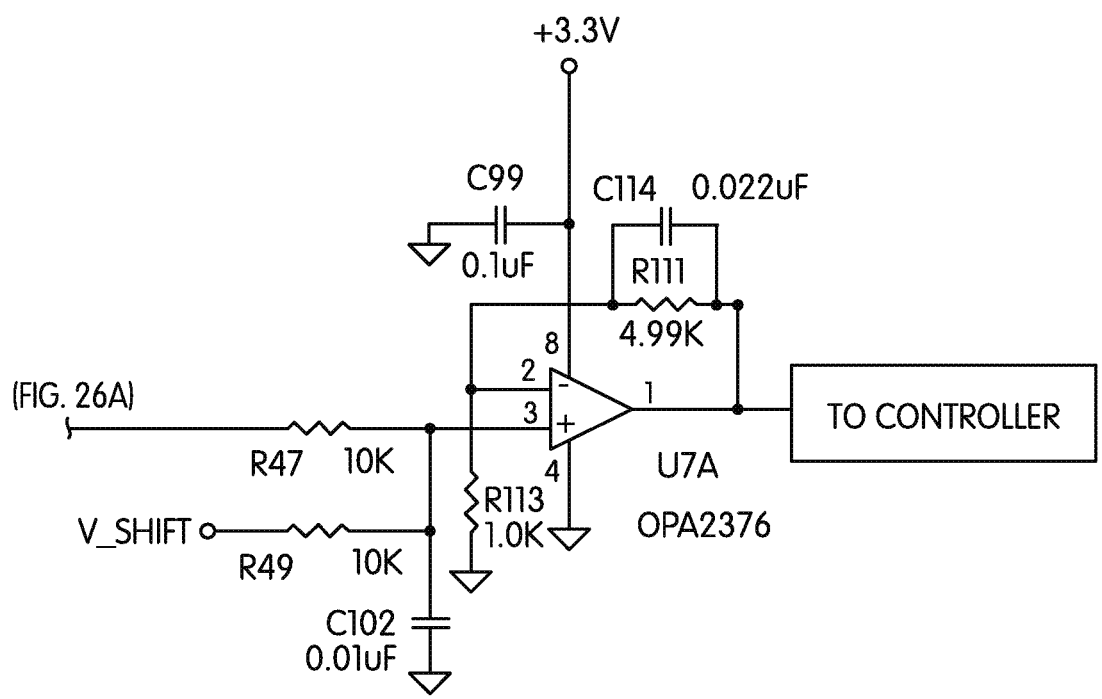

In some embodiments, detector circuits 502a-502e could be configured as shown in FIGS. 26A and 26B. As shown in FIGS. 26A and 26B, each detector circuit 502 includes a pre-amplifier circuit, which includes U11, and the amplifier formed by pins 5-7 of U10B. The pre-amplifier circuit receives current from the photodiode D (corresponding to sensor 423) and converts it to an amplified voltage. As shown, the amplifier that includes pins 1-3 of U10A provides a bias current to compensate for the electrical current out of photodiode D caused by un-modulated ambient light incident on the photodiode D.

Amplifiers U11 and U10B form the first two stages of amplification of the current signal (corresponding to the emission signal) from the photodiode D (423). C54, C44, and C58 provide power supply bypassing/filtering to the amplifiers. C12, D12, R55, R57, and R61 form a filtered power supply that biases the anode of the photodiode D. Feedback resistors R31 and R32 convert electrical current from the photodiode D into a voltage while C48 provides filtering for higher frequency signals. The voltage divider formed by R43 and R45 provides a voltage gain of 10 in the next pre-amplification state while capacitor C56 provides additional low pass filtering.

Detector circuits 502a-502e can be configured to use a level shifter formed by U7A. In some embodiments, the purpose of the level shifter is to move the zero level of the pre-amp up to the middle range of a unipolar analog-to-digital (A/D) converter. This allows the use of A/D converters employed by certain microcontrollers so that an additional A/D converter is not required.

During operation, while multiple receptacles 162 (e.g., receptacles 162 of MRDs 160) are being processed within incubator 200 and one or more signal detectors 400 are measuring the intensity of signal emissions from the receptacles 162 carried on receptacle carrier 242, the signal detectors can be periodically self-checked to detect any failure or deteriorated performance. Such a failure or performance deterioration can affect the accuracy of test results, which hinge on measurement of optical emissions from receptacles 162.

In some embodiments, a self-check is performed by moving a non-fluorescent surface portion 250 into a detection zone of the signal detector 400 that is in optical communication with a detection channel of each signal detector 400 (or in the case of a non-stationary detector, moving the detector such that a detection channel is in optical communication with a non-fluorescent surface portion 250), measuring the optical intensity of light reflected or scattered by the non-fluorescent surface portion 250 and detected by sensor 423, and comparing the measured intensity to an expected, predetermined intensity value range for light being reflected or scattered by non-fluorescent surface portion 250. If the measured intensity is outside the expected intensity value range, it is an indication of failure or deteriorated performance of the respective detection channel of a signal detector 400. In some embodiments, the expected, predetermined intensity value range for light being reflected or scattered by non-fluorescent surface portion 250 is greater than zero, for example, 5 to 600 Relative Fluorescen Units (RFU), 200 to 5800 RFU, or 5 to 550 RFU. By positioning a non-fluorescent surface portion 250, for example, an aluminum surface, in the detection zone of a detection channel of a signal detector 400, a small, detectable (no-zero) amount of light can be reflected or scattered back to signal detector 400 and detected by sensor 423.

In some embodiments, the expected, predetermined intensity value range for light being reflected or scattered by non-fluorescent surface portion 250 varies based on the particular signal detector 400 measuring the light. For example, the expected, predetermined intensity value range for light being reflected or scattered by non-fluorescent surface portion 250 for a signal detector configured to detect an emission signal having a wavelength corresponding to the wavelength (i.e., color) of a specific dye, for example, FAM, may be different than the expected, predetermined intensity value range for light being reflected or scattered by non-fluorescent surface portion 250 for a signal detector configured to detect an emission signal having a wavelength corresponding to the wavelength (i.e., color) of a different specific dye, for example, HEX or ROX. In some embodiments, the predetermined intensity value range for light being reflected or scattered by non-fluorescent surface portion 250 and measured by a signal detector 400 configured to be used with FAM dye is 5-600 RFU. In some embodiments, the predetermined intensity value range for light being reflected or scattered by non-fluorescent surface portion 250 and measured by a signal detector 400 configured to be used with HEX dye is 200-5800 RFU. And in some embodiments, the predetermined intensity value range for light being reflected or scattered by non-fluorescent surface portion 250 and measured by a signal detector 400 configured to be used with ROX dye is 5-550 RFU.

In some embodiments, a self-check is performed by moving a recess (e.g., a void or space lacking matter such as components composing receptacle carrier 242) defined by receptacle carrier 242, for example, a receptacle station 211 that does not have a MRD 160 received therein, and includes opening 265 defined by lower disk 256 into a detection zone of each detection channel of a signal detector 400 for each signal detector 400 (or in the case of a non-stationary detector, moving detector 400 such that each detection channel of each signal detector 400 is in optical communication with the recess), measuring the optical intensity of light detected by sensor 423, and comparing the measured intensity to an expected, predetermined recess intensity value range. If the measured intensity is outside the expected recess intensity value range, it is an indication of failure or deteriorated performance of the respective detection channel of a signal detector 400. In some embodiments, the expected, predetermined recess intensity value range for light being detected by sensor 423 includes zero, for example, 0 to 300 RFU, or 0 to 2260 RFU. By positioning a recess in the detection zone of a detection channel of a signal detector 400, little or no light should be reflected or scattered back to signal detector 400 and detected by sensor 423.

In some embodiments, the expected, predetermined recess intensity value range for light being detected by sensor 423 when a recess is in optical communication with the respective detection channel varies based on the particular signal detector 400 measuring the light. For example, the expected, predetermined recess intensity value range for a signal detector configured to detect an emission signal having a wavelength corresponding to the wavelength (i.e., color) of a specific dye, for example, FAM, may be different than the expected, predetermined intensity value range for light being reflected or scattered by non-fluorescent surface portion 250 for a signal detector configured to detect an emission signal having a wavelength corresponding to the wavelength (i.e., color) of a different specific dye, for example, HEX or ROX. In some embodiments, the predetermined intensity value range for light being detected when a recess is in optical communication with the respective detection channel of a signal detector 400 configured to be used with FAM dye is 0-300 RFU. In some embodiments, the predetermined intensity value range for light being detected when a recess is in optical communication with the respective detection channel of a signal detector 400 configured to be used with HEX dye is 0-2260 RFU. And in some embodiments, the predetermined intensity value range for light being detected when a recess is in optical communication with the respective detection channel of a signal detector 400 configured to be used with ROX dye is 0-300 RFU.

In some embodiments, a self-check for a particular detection channel is performed by both (1) moving a non-fluorescent surface portion 250 into a detection zone of a detection channel of a signal detector 400, measuring the optical intensity of light reflected or scattered by the non-fluorescent surface portion 250 and detected by sensor 423, and comparing the measured intensity to an expected, predetermined intensity value range for light being reflected or scattered by non-fluorescent surface portion 250, and (2) moving a recess defined by receptacle carrier 242 into the detection zone of the detection channel of the signal detector 400, measuring the optical intensity of light detected by sensor 423, and comparing the measured intensity to an expected, predetermined recess intensity value range.

In the case of a stationary signal detector, each non-fluorescent surface portion 250 disposed on receptacle carrier 242 is periodically positioned, for example, by rotating receptacle carrier 242, to be in in optical communication with a detection channel of signal detector 400. Here, "optical communication" refers to positioning the non-fluorescent surface portion 250 in a position with respect to a detection channel of signal detector 400, or positioning a detection channel of signal detector 400 in a position with respect to non-fluorescent surface portion 250, such that the detection channel of signal detector 400 can detect light reflected or scattered by non-fluorescent surface portion 250.

In some embodiments, both receptacle carrier 242 and signal detector 400 are moveable. For example, receptacle carrier 242 and signal detector 400 can be configured to move relative to each other as described in U.S. Pat. No. 7,794,659, issued Sep. 14, 2010, which is incorporated by reference herein.

In the illustrated embodiment, as shown in FIGS. 4, 5, 6, and 9, non-fluorescent surface portions 250 compose portions of outer spokes 264 of lower disk 256 of receptacle carrier 242. Non-fluorescent surface portions 250 are positioned and oriented in the illustrated embodiment such that as receptacle carrier 242 rotates within incubator 200, one or more non-fluorescent surface portions 250 can be moved into a position with respect to a detection channel of a signal detector 400 that will enable signal detector 400 to measure light reflected or scattered by non-fluorescent surface portions 250 using sensor 423. In some embodiments, non-fluorescent surface portions 250 is composed of a non-fluorescent material, for example, aluminum, that will generate a sufficient amount of reflected or scattered light that failure or deteriorated performance of a signal detector by detecting a small, non-zero intensity on sensor 423.

In some embodiments, the bottom surface of an outer spoke 264 of lower disk 256 can define a set of five non-fluorescent surface portions 250 that correspond to the number of detection channels of each signal detector 400. And in some embodiments, the number of sets of non-fluorescent surface portions 250—the number of outer spokes 264 defining a set of non-fluorescent surface portions 250—corresponds to the number of signal detectors 400 positioned beneath incubator 200 so that at least one detection channel of all of signal detectors 400 can be self-checked simultaneously. That is, in one embodiment, each set of five non-fluorescent surface portions 250 corresponds to, or is associated with, one signal detector 400. In other embodiments, each set of five non-fluorescent surface portions 250 are positioned relative to their corresponding signal detector 400 so that one or more, but less than all, signal detectors can be self-checked while one or more other signal detectors are measuring signal emissions from samples.

By integrating the non-fluorescent surface portions 250 into a support structure, such as receptacle carrier 242, within incubator 200, signal detector(s) 400 can be self-checked during operation of incubator 200, including during the real-time monitoring of amplification reactions within the incubator. Thus, the self-check procedure can be performed within the closed system of the incubator without requiring that normal operation of the incubator be interrupted to permit the signal detector(s) to be checked for proper operation.

In some embodiments, instead of using aluminum for non-fluorescent surface portions 250, other materials can be used that have sufficient reflective and scattering properties to produce a small, nonzero detectable intensity at sensor 423. For example, in some embodiments, the non-fluorescent surface portions 250 can be made of non-fluorescing metals other than aluminum (e.g., cobalt, copper, and iron), non-fluorescing plastics (e.g., very dark plastics), or non-fluorescing fiber-reinforced composites, or any other suitable non-fluorescing material. In some embodiments, the component comprising non-fluorescent surface portions 250 is made entirely of a non-fluorescent material. In other embodiments, the component comprising non-fluorescent surface portions 250 can be made from a fluorescing material but coated with a non-fluorescent layer (for example, paint, film, or laminate) to form non-fluorescent surface portions 250. In some embodiments, non-fluorescent surface portions 250 can be made of different materials selected for each type of signal detector 400 (e.g., signal detectors configured to detect FAM, ROX, HEX, etc.).

One advantage of using non-fluorescent materials is that the characteristics (e.g., intensity and wavelength) of light reflected or scattered by non-fluorescent surface portions 250 remains substantially constant over time. In contrast, for example, fluorescing materials can be susceptible to photobleaching over time such that the intensity of light emitted from the fluorescing material decreases over time. Accordingly, non-fluorescent materials suitable for use with assay instruments that are continuously in use for an extended period of time, for example, 12 hours a day for 300 days per year.

In some embodiments, portions of receptacle carrier 242 other than spokes 264 can define non-fluorescent surface portions 250. For example, receptacle carrier 242 can include a structure (not shown) between lower disk 26 and upper disk 244 that defines non-fluorescent surface portions 250.

Figure 15:
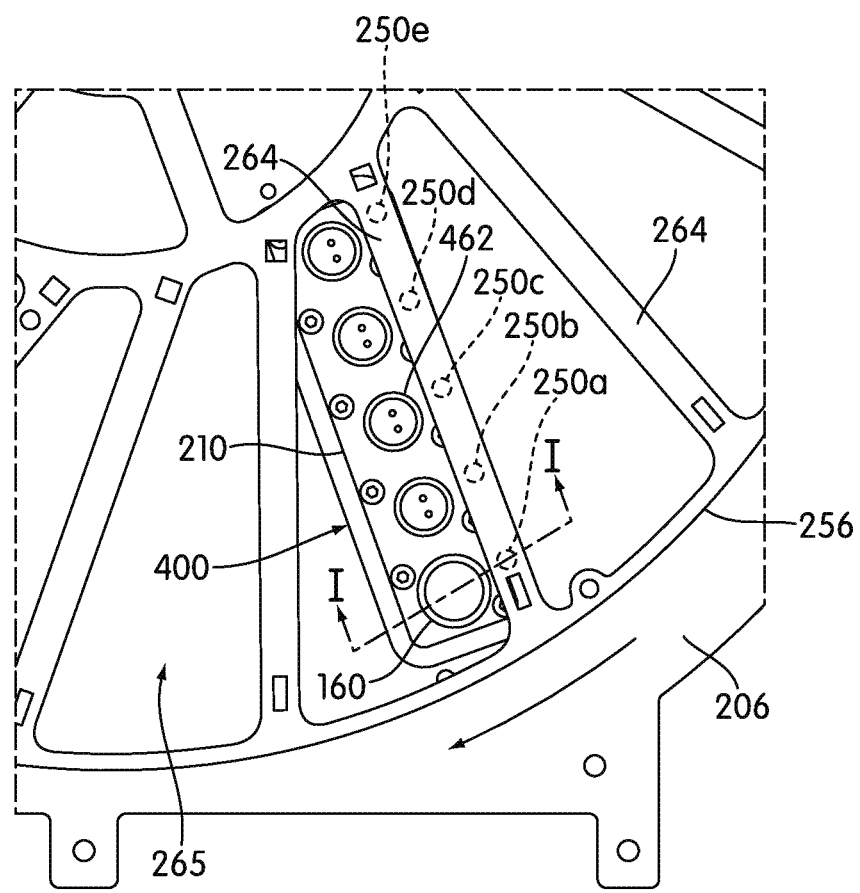
FIG. 15 is a partial top plan view of a lower disk of the receptacle carrier carousel of the incubator, showing alignment of a multiple receptacle device carried on the receptacle carrier with a signal detector positioned below the receptacle carrier and the relative orientations of fluorescent standards mounted on the lower disk relative to the signal detector, according to an embodiment.

As shown in FIG. 15, in some embodiments, outer spokes 264 are not arranged in a radial orientation with respect to a center of lower disk 256. In such embodiments, each signal detector 400 can be parallel to outer spokes 264 and is oriented such that each of its five detection channels will simultaneously align with one of receptacle 162 of a MRD 160 positioned above signal detector 400 and aligned with opening 210 defined by the incubator housing. Because MRD 160 is carried on receptacle carrier 242 at a position that is adjacent to and parallel with outer spoke 264, and because outer spoke 264 and MRD 160 are not carried in a radial orientation relative to a center of receptacle carrier 242, the non-fluorescent surface portions 250 of each set will not simultaneously align with all of the five detection channels of a signal detector 400. Therefore, to place each of non-fluorescent surface portions 250 on outer spoke 264 in optical communication with a corresponding channel of signal detector 400, receptacle carrier 242 must be rotated in five increments to five different angular positions to self-check all five detection channels of signal detector 400 based on measured intensities of light reflected or scattered by a non-fluorescent surface portion 250. In one embodiment, receptacle carrier 242 must be rotated 4.65 degrees from the position shown in FIG. 15 to place a first non-fluorescent surface portion 250a (i.e., the radially outermost non-fluorescent surface portion 250) into optical communication with the outermost detection channel of signal detector 400. Each subsequent incremental rotation (relative to the position shown in FIG. 15) required to position the next four non-fluorescent surface portion 250b-250e into optical communication with their corresponding detection channels are shown in the following table.

| Angular position | Angle |
| --- | --- |
| MRD 160 and fluorometer aligned (as in FIG. 15) | 0° |
| Reference target 250a aligned with outermost fluorometer detection channel | 4.65° |
| Reference target 250b aligned with second fluorometer detection channel | 5.35° |
| Reference target 250c aligned with third detection fluorometer channel | 6.25° |
| Reference target 250d aligned with fourth fluorometer detection channel | 7.6° |
| Reference target 250e aligned with fifth (innermost) detection fluorometer channel | 9.75° |

In some embodiments, after receptacle carrier 242 is rotated between the five angular positions aligning non-fluorescent surface portion 250b-250e with the respective detection channels of the signal detector 400, receptacle carrier 242 is rotated to an angular position at which a recess defined by receptacle carrier 242 is aligned with each set of detection channels of each signal detector 400. In some embodiments, the recess is a receptacle station 211 that does not have a MRD 160 received therein and includes opening 265 defined by lower disk 256. At this angular position, a self-check can be performed for each detection channel of each signal detector 400 based on light intensity measured by the respective sensors 423 of the detection channels.

Figure 31A:
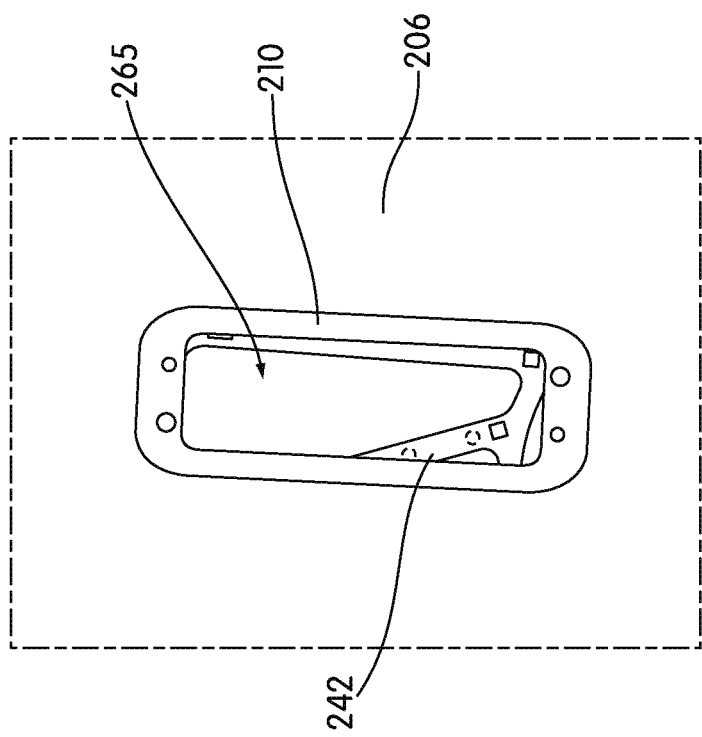
FIGS. 31A and 31B are bottom plan views of a receptacle carrier of the incubator with a recess in the detection zones of all detection channels of a signal detector (FIG. 31A) and non-fluorescent portion 250 in a detection zone of one detection channel of a signal detector (FIG. 31B), according to an embodiment.
Figure 31B:
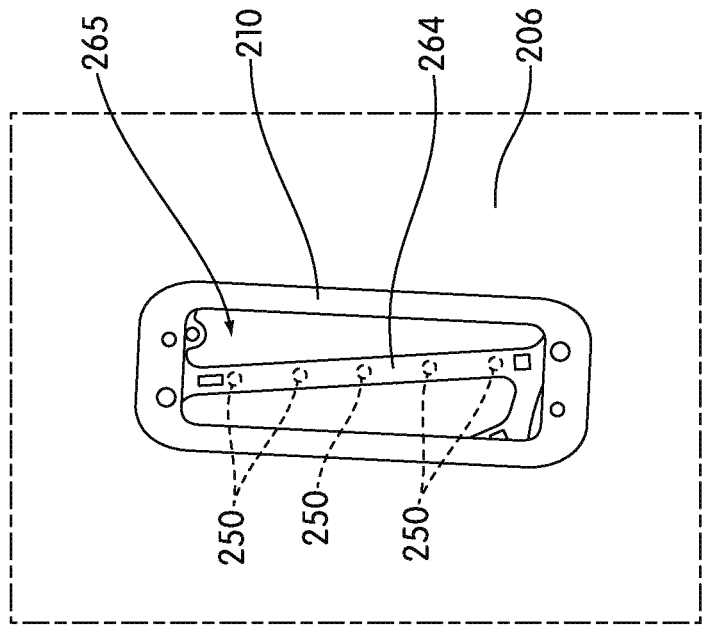

In some embodiments, a controller and drive assembly 300 are configured to rotate receptacle carrier 242 to eighteen different angular positions during one revolution of receptacle carrier 242. At twelve of the eighteen different angular positions, a receptacle 162 of an MRD 160 is optically coupled to each detection channel of each signal detector 400. For example, at these twelve positions a bottom portion of a receptacle 162 of an MRD 160 is positioned in a detection zone of each detection channel of each signal detector 400. At one of the eighteen different angular positions, a recess defined by receptacle carrier 242 is optically coupled to each set of detection channels of each signal detector 400. For example, at this one position a recess is positioned in the detection zones of each detection channel of each signal detector 400. FIG. 31A illustrates one recess positioned in the detection zone of each detection channel of one signal detector 400 at this one angular position according to an embodiment. And at the remaining five of the eighteen different angular positions, a respective non-fluorescent surface portion 250 is optically coupled to one respective detection channel of each signal detector 400. For example, at these remaining five positions a non-fluorescent surface portion 250 on receptacle carrier 242 is positioned in a detection zone of one detection channel of each signal detector 400. FIG. 31B illustrates one non-fluorescent surface portion 250 (i.e., the middle non-fluorescent surface portion 250) in the detection zone of one detection channel (i.e., the middle detection channel) of one signal detector 400 at one of these five angular positions according to an embodiment.

Rather than moving receptacle carrier 242 by each of the small incremental rotations listed above to sequentially place all the detection channels of all signal detectors 400 into self-check positions with respect to an associated non-fluorescent surface portion 250, in one embodiment, a different channel of each of signal detectors 400 is self-tested with each revolution of the carousel. Thus, after one revolution of receptacle carrier 242 during which all receptacle vessels of all the MRDs 160 are interrogated by all signal detectors 400, the carousel is advanced until one of the detection channels (e.g., the outer most detection channel) of all signal detectors 400 is aligned with an associated non-fluorescent surface portion 250 for a self-check of all the first channels. After a next revolution of receptacle carrier 242, receptacle carrier 242 is advanced until the next channel (e.g., the second outer most detection channel) of all signal detectors 400 is aligned with an associated non-fluorescent surface portion 250 for a self-check of all the second channels. This process is repeated for each subsequent revolution of receptacle carrier 242 to self-check the third, fourth, and fifth detection channels of signal detectors 400. Thus, according to this embodiment, each channel of each signal detector is self-checked once in every five revolutions of the carousel.

Figure 16:
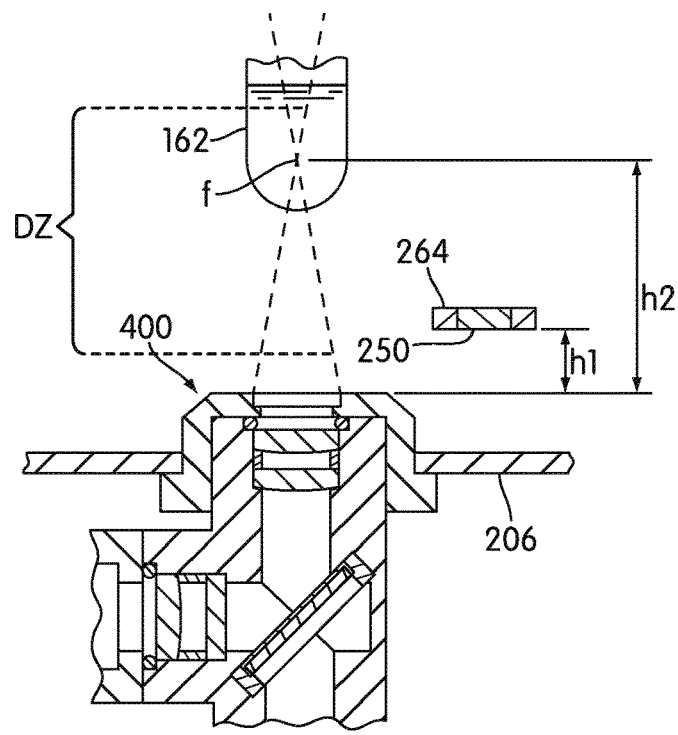
FIG. 16 is a partial side cross sectional view (along ling I-I in FIG. 15) showing a signal detector and a receptacle carried on the receptacle carrier in a detection zone with respect to the signal detector, according to an embodiment.

In one embodiment, signal detectors 400 are configured so that a portion of receptacle 162 carried by receptacle carrier 242 will be at an optical focal point of a corresponding detection channel of signal detector 400 when receptacle 162 is operatively positioned above signal detector 400. As shown in FIG. 16, when receptacle 162 is positioned above signal detector 400 within incubator 200, a portion of receptacle 162 (e.g., a portion containing a sample within receptacle 162) is at a focal point f (within a detection zone DZ of signal detector 400) at a height $h_2$ with respect to the corresponding detection channel of signal detector 400. Non-fluorescent surface portion 250 on the other hand, on outer spoke 264 of lower disk 256 is at a height $h_1$ that is less than $h_2$ above signal detector 400. In one embodiment, $h_1$ is 1.0 mm and $h_2$ is 8.5 mm. In another embodiment, $h_1$ is 2.0 mm and $h_2$ is 10 mm. In other embodiments, $h_1$ is 1% to 99% smaller than $h_2$, in other embodiments, $h_1$ is 20% to 80% smaller than $h_2$, and in still other embodiments, $h_1$ is 60% to 90% smaller than $h_2$.

Figure 17:
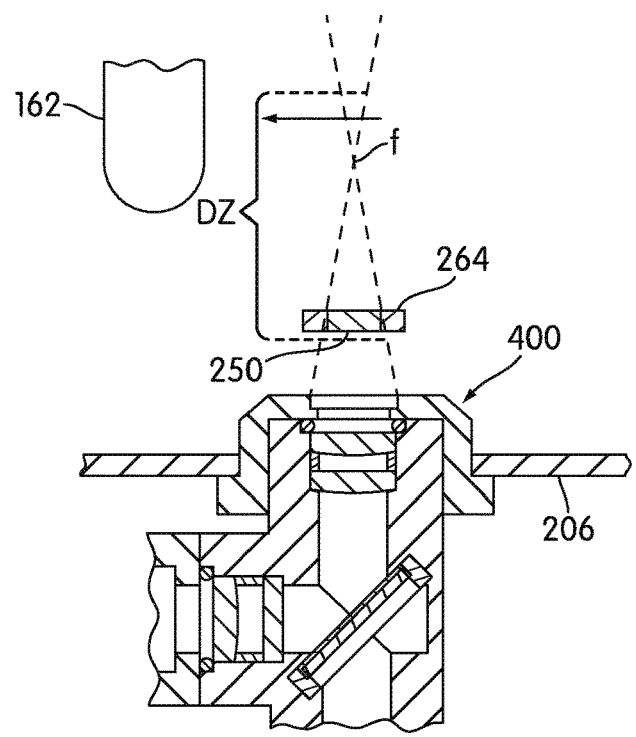
FIG. 17 is a partial side cross sectional view (along ling I-I in FIG. 15) showing the signal detector, the receptacle moved out of the detection zone with respect to the signal detector, and a fluorescent standard moved into optical communication with the signal detector but not in the detection zone with respect to the signal detector, according to an embodiment.

As shown in FIG. 17, after receptacle carrier 242 rotates in the direction of the lateral arrow to move receptacle 162 out of focal point f and position non-fluorescent surface portion 250 in detection zone DZ and into optical communication with the detection channel of signal detector 400. Although non-fluorescent surface portion 250 may not be at focal point f of the corresponding detection channel of signal detector 400, non-fluorescent surface portion 250 is within detection zone DZ of the detection channel of sign detector 400. (The distance before and the distance beyond focal point f (relative to signal detector 400) at which sensor 423 of signal detector 400 can detect light reflected or scattered by non-fluorescent surface portion 250 bounds the detection zone DZ of the respective detection channel of signal detector 400.) Thus, although non-fluorescent surface portion 250 is out of focus with respect to signal detector 400, sensor 423 of signal detector 400 can detect a light signal reflected or scattered by non-fluorescent surface portion 250.

In other embodiments, $h_2$ is less than $h_1$. Non-fluorescent surface portion 250 may be above (or otherwise further from) focal point f at $h_2$. In such embodiments, $h_2$ may be 1% to 99% smaller than $h_1$, 20% to 80% smaller than $h_1$, or 60% to 90% smaller than $h_1$.

Figure 18:
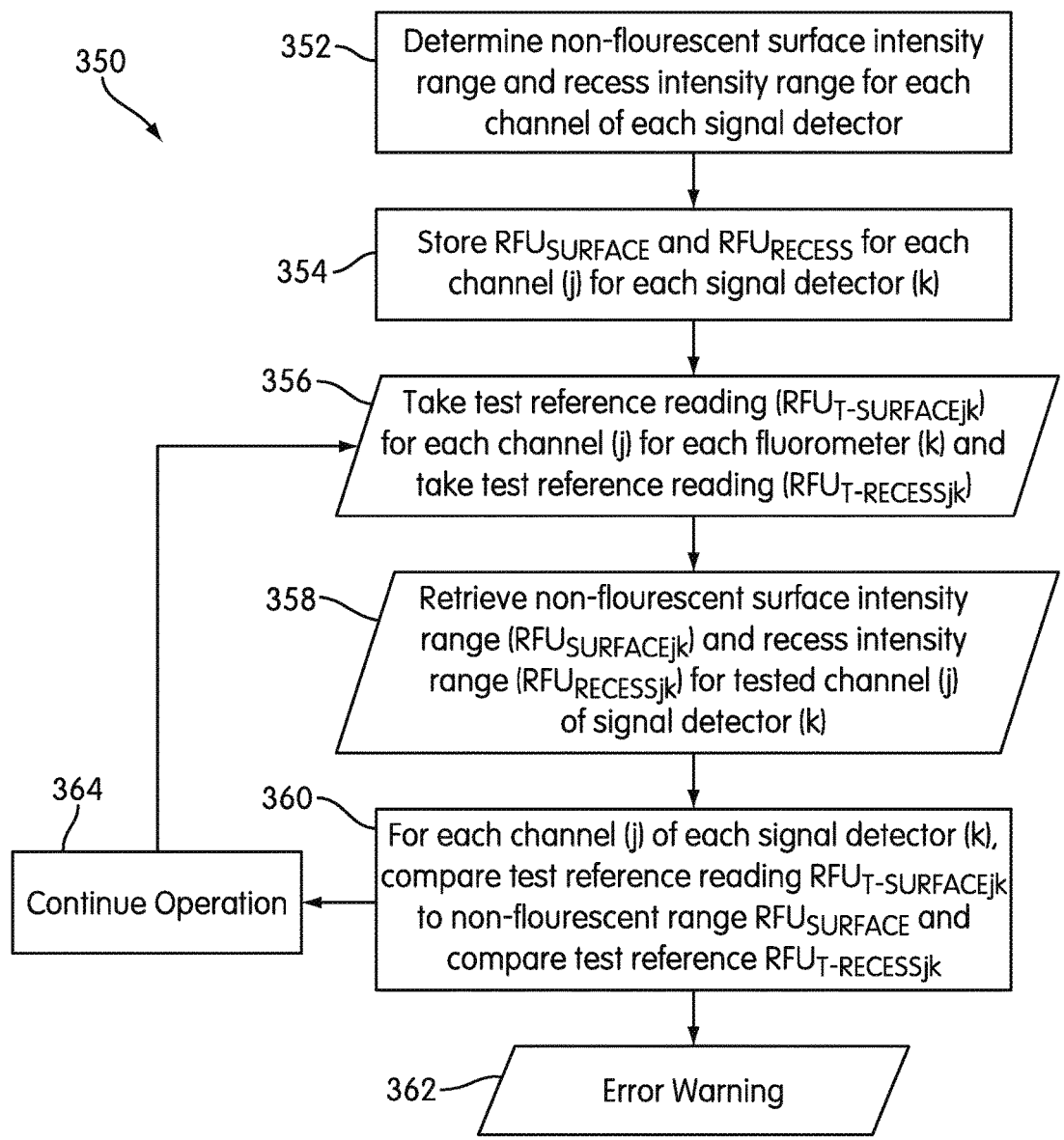
FIG. 18 is a flow chart showing a self-check procedure for a fluorometer or other optical signal detector, according to an embodiment.

An exemplary automated, self-check procedure for a signal detector 400 is represented by flow chart 350 shown in FIG. 18. The procedure is performed with signal detector 400 and receptacle carrier 242, which are controlled by a controller (e.g., a microprocessor) executing software that includes an algorithm embodying procedure 350 encoded or stored on a computer-readable medium.

At Step 352, a non-fluorescent-surface intensity range $RFU_{surface}$ and a recess intensity range $RFU_{recess}$ are determined for each sensor 423 (or detection channel) of each signal detector 400. The non-fluorescent-surface intensity range $RFU_{surface}$ includes the intensities, for example, in Relative Fluorescent Units ("RFU") or other units in some embodiments, that are expected to be detected by each sensor 423 of each signal detector 400 by light reflected and scattered by respective non-fluorescent surface portions 250. In some embodiments, the expected values in the non-fluorescent-surface intensity ranges $RFU_{surface}$ are non-zero. For example, the non-fluorescent-surface intensity range $RFU_{surface}$ can be 5 to 600 RFU. The recess intensity range $RFU_{recess}$ includes the intensity measurement values, for example, in Relative Fluorescent Units ("RFU") or in other units in some embodiments, that are expected to be detected by sensor 423 of signal detector 400 when a recess is in the detection zone of signal detector 400. In some embodiments, the values in the recess intensity range $RFU_{recess}$ are zero or significantly small due to noise. In some embodiments, recess intensity range $RFU_{recess}$ is 0 to 300 RFU. Step 352 can occur before or after signal detector 400 is installed in incubator 200.

In some embodiments, the non-fluorescent-surface intensity range $RFU_{surface}$ for each sensor 423 (or detection channel) of each signal detector 400 is the same. In other embodiments, the non-fluorescent-surface intensity range $RFU_{surface}$ for each sensor 423 (or detection channel) of each signal detector 400 varies based on the particular signal detector.

In some embodiments, the recess intensity range $RFU_{recess}$ for each sensor 423 (or detection channel) of each signal detector 400 is the same. In other embodiments, the recess intensity range $RFU_{recess}$ for each sensor 423 (or detection channel) of each signal detector 400 varies based on the particular signal detector.

At Step 354, the non-fluorescent-surface intensity range and the recess intensity range for each sensor 423 (or detection channel) of each signal detector 400, determined at Step 352, is stored in suitable memory that is accessible by a controller, for example, by a microprocessor. In some embodiments, the memory is part of the assay instrument.

At Step 356, after an interval of usage of each signal detector 400, an intensity measurement is acquired for each channel (j) for each signal detector (k) by moving the associated non-fluorescent surface portions 250 into optical communication (i.e., within the detection zone DZ for each channel (j) for each signal detector (k)) with the channel and measuring an optical intensity from light reflected by or scattered by the associated non-fluorescent surface portions 250. The test reference intensity of the $j^{th}$ channel for the $k^{th}$ signal detector when the non-fluorescent surface portion 250 is in optical communication with the channel is $RFU_{T\text{-}SURFACEjk}$. And at Step 356, an intensity measurement is acquired for each channel (j) for each signal detector (k) by moving an associated recess into optical communication (i.e., within the detection zone DZ for each channel (j) for each signal detector (k)) with the channel and measuring an optical intensity detected by the sensor for each channel (j) for each signal detector (k). The test reference intensity of the $j^{th}$ channel for the $k^{th}$ signal detector when the associate recess is in optical communication with the channel is $RFU_{T\text{-}RECESSjk}$.

At Step 358, the non-fluorescent-surface intensity range $RFU_{SURFACE}$ and the recess intensity range $RFU_{RECESS}$ for the $j^{th}$ channel and the $k^{th}$ fluorometer ($RFU_{SURFACEjk}$ and $RFU_{RECESSjk}$) are retrieved from memory.

And at Step 360, an operational performance status of signal detector (k) can be determined based on at least one of test reference intensity $RFU_{T\text{-}SURFACEjk}$ and test reference intensity $RFU_{T\text{-}RECESSjk}$. The operational performance status is an indication of whether the fluorometer is operating properly. Exemplary operational performance statuses include a proper operational status (e.g., the fluorometer is operating properly and correcting detecting light focused on its sensor), a failure status (e.g., the fluorometer is not operating properly and is not detecting light focused on its sensor), and a deteriorating performance status (e.g., the fluorometer is not operating properly and is only partially detecting light focused on its sensor). For example, test reference intensity $RFU_{T\text{-}SURFACEjk}$, when the non-fluorescent surface portion 250 is in optical communication with the channel, is compared to the non-fluorescent-surface intensity range $RFU_{SURFACE}$, and test reference intensity $RFU_{T\text{-}RECESSjk}$, when the recess is in optical communication with the channel, is compared to the recess intensity range $RFU_{RECESS}$. In one embodiment, Step 360 is performed by an algorithm that determines whether test reference intensity $RFU_{T\text{-}SURFACEjk}$ is within the predetermined non-fluorescent-surface intensity range $RFU_{SURFACE}$, and determines whether test reference intensity $RFU_{T\text{-}RECESSjk}$ is within the predetermined recess intensity range $RFU_{RECESS}$.

If test reference intensity $RFU_{T\text{-}SURFACEjk}$ is outside the predetermined non-fluorescent-surface intensity range $RFU_{SURFACE}$, test reference intensity $RFU_{T\text{-}RECESSjk}$ is outside the predetermined recess intensity range $RFU_{RECESS}$, or both, the operational performance status of signal detector (k) is determined either a failure status or a deteriorated performance status, and possible malfunction of signal detector (k) is indicated, and at Step 362, an error warning or other indication of the possible malfunction is provided. In some embodiments, when a warning indication is provided at Step 362, operation of the signal detector (k) may be interrupted or terminated.

If test reference intensity $RFU_{T\text{-}SURFACEjk}$ is within the predetermined non-fluorescent-surface intensity range $RFU_{SURFACE}$ and test reference intensity $RFU_{T\text{-}RECESSjk}$ is within the predetermined recess intensity range $RFU_{RECESS}$, the signal detector (k) is deemed to be functioning properly, and, at Step 366, operation continues and, as long as the fluorometer continues operation (until a stop condition is reached), periodic self-checks are performed by repeating Steps 356, 358, and 360.

In one embodiment, periodic test reference readings can be taken and compared to the initial reference readings at least once every 50 minutes, though the interval can vary significantly in accordance with the user preferences and type of assay being performed. A stop condition may be indicated by completion of the test or assay, a need to stop operation of the instrument to replenish reagents, MRDs, or other disposables, or if, during a fluorometer self-check, the deviation between the test and initial, or baseline, reference readings exceeds the threshold.

Steps 358, 360, 362, and 364 are performed by a controller (e.g., a microprocessor) executing software that includes an algorithm embodying Steps 358, 360, 362, and 364 encoded or stored on a computer-readable medium.

In some embodiments, steps 352-360 can occur before signal detector 400 is installed in incubator 200 or any other device that utilizes a signal detector 400. For example, steps 352-360 can be performed during or shortly after signal detector 400 is being manufactured to verify that signal detector 400 is operating properly (e.g., a failure status or a deteriorated performance status is not indicated at step 360)

before being installed in incubator 200 or any other device that utilizes signal detector 400. In some embodiments in which steps 352-360 occur before signal detector 400 is installed in incubator 200 or any other device that utilizes a signal detector 400, steps 364 and 362 can be omitted from process 350.

Figure 27:
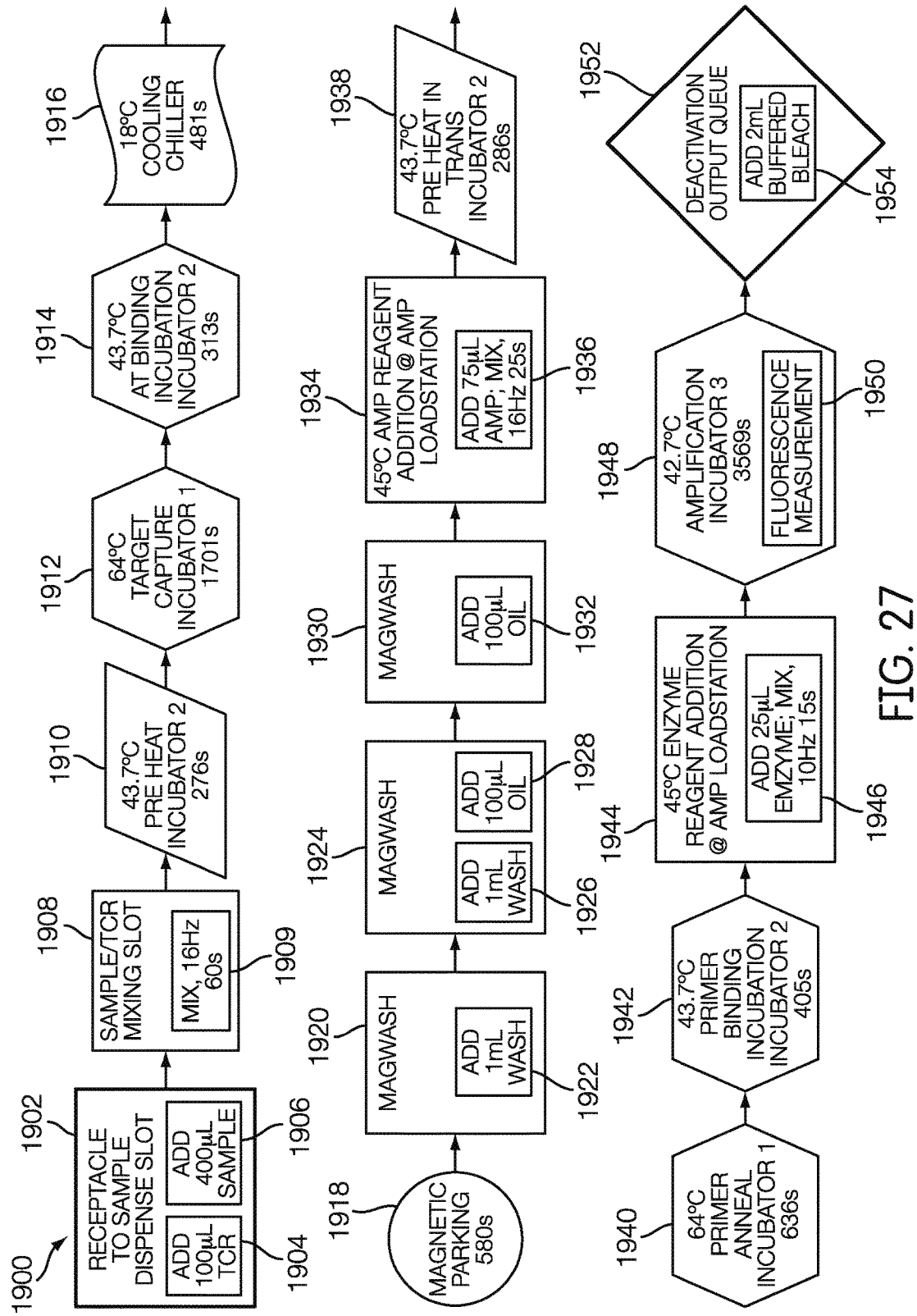
FIG. 27 is a flow chart showing the protocols of an exemplary real-time amplification assay, according to an embodiment.

The process steps of an exemplary real-time amplification assay procedure 1900 are illustrated in the flow chart shown in FIG. 27. The procedure 1900 is performed by an assay instrument of which one or more incubators, such as incubator 200, is a component and which is controlled by a controller (e.g., a microprocessor) executing software that includes an algorithm embodying procedure 1900 encoded or stored on a computer-readable medium. The process shown in FIG. 27 is similar to an analogous process described in detail in Macioszek et al., "Methods for Performing Multi-Formatted assays," U.S. Pat. No. 7,897,337. The steps described represent exemplary TAA procedures only. The steps described below may be varied or omitted, or other steps may be added or substituted in accordance with the desired real-time amplification assay procedures. Reagent formulations for performing a host of amplification procedures are well known in the art and could be used in or readily adapted for use in the present disclosure. See, e.g., Kacian et al., U.S. Pat. No. 5,399,491; Becker et al., U.S. Pat. No. 7,374,885; Linnen et al., "Compositions and Methods for Detecting West Nile Virus," U.S. Pat. No. 7,115,374; Weisburg et al., "Compositions, Methods and Kits for Determining the Presence of *Trichomonas Vaginalis* in a Test Sample," U.S. Pat. No. 7,381,811; and Kacian, "Methods for Determining the Presence of SARS Coronavirus in a Sample," U.S. Patent Application Publication No. 2010-0279276 A1.

The process steps of the exemplary real-time TAA amplification assay procedure 1900 begin with step 1902, in which a receptacle, such as an MRD 160, is moved to a pipetting position in a sample transfer station (not shown). In step 1904, a sample pipette assembly (not shown) dispenses a target capture reagent ("TCR"), e.g., 100 µL of TCR, including magnetically-responsive particles into the receptacle, e.g., into each receptacle 162 of MRD 160. In some embodiments, the TCR includes a capture probe, a detergent-containing lytic agent, e.g., lithium lauryl sulfate, for lysing cells and inhibiting the activity of RNAses present in the sample material, and about 40 µg Sera-Mag™ MG-CM Carboxylate Modified (Seradyn, Inc., Indianapolis, Ind.; Cat. No. 24152105-050250), 1 micron, super-paramagnetic particles having a covalently bound poly(dT)14. In some embodiments, the capture probe includes a 5' target binding region and a 3' region having a poly(dA)30 tail for binding to the poly(dT)14 bound to the magnetic particle. The target binding region of the capture probe is designed to bind to a region of the target nucleic acid distinct from the regions targeted by the primers and the detection probe.

In step 1906, the sample, e.g., 40 µL of the sample, is dispensed into the receptacle. In step 1908, the receptacle, e.g., MRD 160, is moved to a mixer (not shown), and in step 1909, the sample and TCR are mixed, for example, at 16 Hz for 60 seconds. Note that the times and amounts given in FIG. 27 and the description thereof are exemplary desired times and amounts, and the actual times and amounts may, in practice, vary from the given desired times and amounts.

In one embodiment, the assay instrument includes three incubators maintained at three different temperatures: a first incubator maintained at a temperature, for example, 64° C., for target capture and primer annealing; a second incubator maintained at a temperature, for example, 43.7° C., for pre-heating receptacles, AT binding, and primer binding; and a third incubator maintained at a temperature, for example, 42.7° C., for amplification. The first, second, and third incubators may be configured the same as incubator 200 described above, although the first and second incubators may omit signal detectors 400.

In step 1910, the receptacle is moved to the second incubator to pre-heat the receptacle and its contents, for example, at a temperature of 43.7° C. for 276 seconds. In other embodiments, the receptacle may be placed in a temperature ramping station (i.e., a temperature-controlled enclosure (not shown) configured to receive and hold one or more receptacles) for the pre-heating step. In step 1912, the receptacle is moved to the first incubator (i.e., target capture ("TC") incubator) where it resides, for example, at 64° C. for 1701 seconds, for hybridization of the capture probe to target nucleic acids extracted from the sample. (At this temperature, there will be no appreciable hybridization of the capture probe to the immobilized poly(dT)14 oligonucleotide.) In step 1914, the receptacle is moved from the TC incubator to the second incubator for AT binding where the receptacle is held, for example, for 313 seconds at 43.7° C., to allow for immobilized oligonucleotides associated with the magnetic particles to bind to the capture probes. In step 1916, the receptacle is moved to a cooling chiller (i.e., a temperature-controlled enclosure configured to receive and hold one or more receptacles (not shown)) where the receptacle is held, for example, at 18° C. for 481 seconds.

In step 1918, the receptacle is moved to a magnetic parking station (not shown), configured to hold one or more receptacles in proximity to one or more magnets so that the contents of each receptacle 162 are exposed to a magnetic field to draw the magnetically-responsive particles of the target capture reagent to a portion of the receptacle adjacent to the magnet and out of suspension. A suitable magnetic parking station is described in Davis et al., U.S. Patent Application Publication No. 2010/0294047, "Method and System for Performing a Magnetic Separation Procedure."

In step 1920, the receptacle is moved to a magnetic separation station (not shown) for the magnetic separation wash procedure, such as is described in Lair et al., U.S. Patent Application Publication No. 2007-0243600 A1. Within the magnetic separation station, magnets, which are selectively placed in close proximity to the reaction vessel, are used to draw and hold the magnetically-responsive particles to a portion of the vessel. Once the magnetically-responsive particles, and any target nucleic acid bound thereto, are thus immobilized, the hybridized nucleic acid can be separated from non-hybridized nucleic acid by aspirating fluid from the reaction vessel. After the initial aspiration of the fluid contents from the vessel, wash solution, for example, 1 mL of wash solution, is added to the receptacle in step 1922. Step 1924 comprises a second magnetic wash, which includes, after the fluid contents of the receptacle are aspirated, adding wash solution, for example, 1 mL, to the receptacle in step 1926 and adding 100 µL oil (e.g., silicone oil), or other surface treating agent, to the receptacle in step 1928. In step 1930, a final magnetic wash procedure is performed (in other embodiments, more or fewer magnetic wash procedures can be performed) followed by a final dispense of oil (e.g., silicone oil), for example, 100 µL of oil, or other surface treatment agent, in step 1932.

An advantage of adding a surface treating agent, such as silicone oil, to the sample solution in step 1928 is that it reduces the amount of material that adheres to the inner surfaces of the reaction receptacles 162 during the rinsing and aspiration steps of a magnetic separation wash procedure, thereby facilitating a more effective magnetic separation wash procedure. Although the MRDs 160 are can be made of a hydrophobic material, such as polypropylene, small droplets of material, such as wash solution, may still form on the inner surfaces of the MRD receptacles 162 during the aspiration steps of a magnetic separation wash procedure. If not adequately removed from receptacles 162 during the magnetic separation wash procedure, this residual material, which may contain nucleic acid amplification inhibitors, could affect assay results. In alternative approaches, the surface treating reagent could be added to receptacles 162 and removed prior to adding TCR and sample or the surface treating agent could be added to the reaction tubes after TCR and sample have been aspirated from the reaction tubes, possibly with the wash solution, and then removed prior to adding amplification and enzyme reagents to the reaction tubes. The objective is to provide inner surfaces of receptacles 162 with a coating of the surface treating agent. Inhibitors of amplification reactions are known in the art and depend on the sample source and amplification procedure to being used. Possible amplification inhibitors include the following: hemoglobin from blood samples; hemoglobin, nitrates, crystals and/or beta-human chorionic gonadotropin from urine samples; nucleases; proteases; anionic detergents such as sodium dodecyl sulfate (SDS) and lithium lauryl sulfate (LLS); and EDTA, which is an anticoagulant and fixative of some specimens that binds divalent cations like magnesium, which, as noted above, is a cofactor used in nucleic acid-based amplification reactions. See, e.g., Mahony et al., J. Clin. Microbiol., 36(11):3122-2126 (1998); Al-Soud, J. Clin. Microbiol., 39(2):485-493 (2001); and Kacian et al., "Method for Suppressing Inhibition of Enzyme-Mediated Reactions By Ionic Detergents Using High Concentration of Non-Ionic Detergent," U.S. Pat. No. 5,846,701. Silicone oil is added to each reaction vessel 162 of MRD 160 in step 1932 to prevent evaporation and splashing of the fluid contents during subsequent manipulations.

In step 1934, amplification reagent, which is stored in a chilled environment, is added to each receptacle while the receptacle is held, for example, at 45° C., at an amplification load station (not shown). In step 1936, an amplification reagent, for example, 75 µL, are dispensed into the receptacle disposed within the load station, and the receptacle is then mixed for 25 seconds at 16 Hz by a mixer incorporated into the load station. For the exemplary TAA reactions, the amplification reagents contain an antisense promoter-primer having a 3' target binding region and a 5' promoter sequence recognized by an RNA polymerase, a sense primer that binds to an extension product formed with the promoter-primer, nucleoside triphosphates (i.e., dATP, dCTP, dGTP, dTTP, ATP, CTP, GTP and UTP), and cofactors sufficient to perform a TAA reaction. For the real-time TAA amplification assay, the amplification reagent also contains strand displacement, molecular torch probes having interacting label pairs (e.g., interacting fluorescent and quencher moieties joined to the 5' and 3' ends thereof by conventional means) and a target specific region capable of detectably hybridizing to amplification products as the amplification is occurring and, in some embodiments, not to any non-target nucleic acids which may be present in the receptacles. See Kacian et al., U.S. Pat. No. 5,399,491; Becker et al., "Single-Primer Nucleic Acid Amplification," U.S. Pat. No. 7,374,885 (disclosing an alternative TAA-based amplification assay in which an antisense primer and a sense promoter oligonucleotide blocked at its 3' end are employed to minimize side-product formation); and Becker et al., U.S. Pat. No. 6,361,945.

In step 1938, the receptacle is moved to the second incubator and preheated, for example, at 43.7° C. for 286 sec. In step 1940, the receptacle is moved to the first incubator and incubated, for example, at 64° C. for 636 seconds, for primer annealing. In step 1942, the receptacle is moved to the second incubator and incubated, for example, for 405 seconds at 43.7° C., for binding of the promoter-primer to a target nucleic acid. In some embodiments, the promoter-primer can have a promoter sequence recognized by a T7 RNA polymerase.

In step 1944, the receptacle is moved to the load station for enzyme reagent addition, for example, at 45° C. In step 1946, an enzyme, for example, 25 is added, and the MRD is mixed, for example, at 10 Hz for 15 seconds. In step 1948, the receptacle is moved to the third incubator (amplification incubator), where the receptacle contents are incubated, for example, at 42.7° C. for 3569 seconds, for amplification. During amplification, real-time fluorescence measurements are taken in step 1950. In one embodiment, step 1950 comprises taking multiple, real-time fluorescence measurements during rotation of receptacle carrier 242 whereby each receptacle 162 of each MRD 160 is interrogated by each signal detector 400 once per revolution of receptacle carrier 242. During step 1950, each channel of each signal detector 400 is periodically self-checked, e.g., every revolution of receptacle carrier 242 or at least once every five revolutions of the receptacle carrier 242 as described above, using steps 356 to 366 of the automated self-check procedure 350 shown in FIG. 18. In some embodiments, the enzyme reagent contains a reverse transcriptase and a T7 RNA polymerase for performing TAA.

After the nucleic acid-based assay is complete, and to avoid possible contamination of subsequent amplification reactions, the reaction mixture can be treated with a deactivating reagent which destroys nucleic acids and related amplification products in the reaction vessel. In such an example, following amplification and real-time measurements, in step 1952, the receptacle is moved to a deactivation queue, or module (not shown), and in step 1954, a bleach-based agent, for example, 2 mL of a bleach-based agent, is provided to each receptacle to deactivate nucleic acid (i.e., alter the nucleic acid such that it is non-amplifiable) present in the receptacle. Such deactivating agents can include oxidants, reductants, and reactive chemicals, among other suitable deactivating agents, which modify the primary chemical structure of a nucleic acid. These reagents operate by rendering nucleic acids inert towards an amplification reaction, whether the nucleic acid is RNA or DNA. Examples of such chemical agents include solutions of sodium hypochlorite (bleach), solutions of potassium permanganate, formic acid, hydrazine, dimethyl sulfate and similar compounds. More details of a deactivation protocol can be found in, e.g., Dattagupta et al., U.S. Pat. No. 5,612,200, and Nelson et al., U.S. Patent Application Publication No. US 2005-0202491 A1.

Incubator 200 includes a plurality of signal detectors 400 configured to measure in real time the concentration of unquenched fluorescent dye molecules located in a receptacle 162 of MRD 160. And the assay is designed such that the fluorescent signal increases as the concentration of the target is increased by amplification. Signal detectors 400, therefore, may be used to monitor the amplification process by monitoring the emergence of the fluorescent signal.

Figure 29:
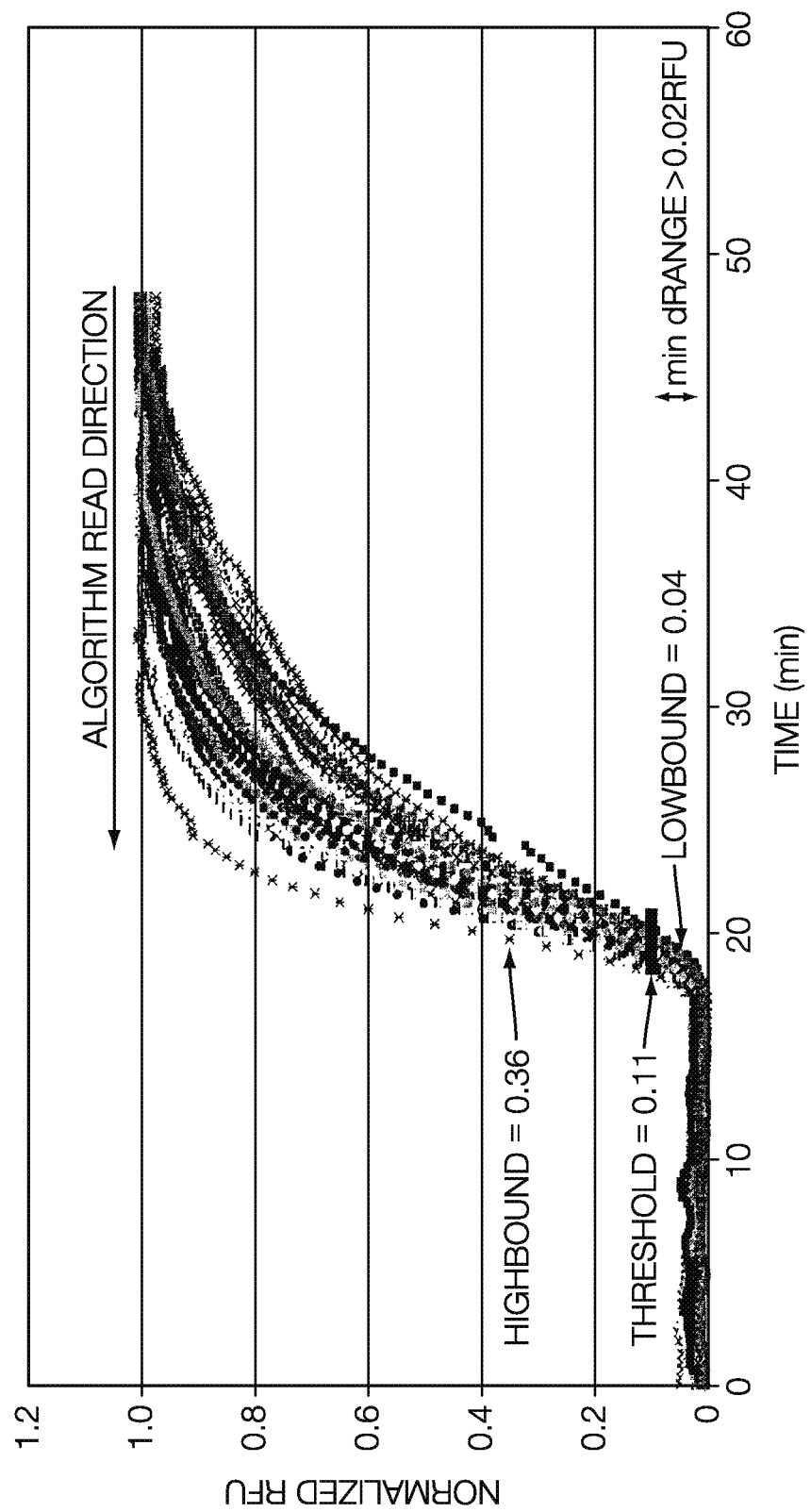
FIG. 29 is a time plot of real-time fluorometer data, according to an embodiment.

Once the data has been collected by measuring fluorometric emissions from each receptacle 162 at prescribed intervals for a prescribed period of time, and while periodically self-checking the fluorometer as described above to confirm that the fluorometer is functioning properly, the data is processed to determine the concentration of a particular analyte (e.g., a target nucleic acid) in the sample contained in receptacle 162 of MRD 160. The measured data, that is, the measured signal, will be referred to in terms of Relative Fluorescent Units ("RFU"), which is the signal generated by the detection PCB 422 of signal detector 400 based on the amount of emission fluorescence focused onto sensor 423. Each data point, measured at a given time interval, is RFU(t). Plots of RFU(t) for a variety of data sets, known as "growth curves" are shown in FIG. 29. In general, each RFU(t) plot is generally sigmoidal in shape, characterized by an initial, flat portion (known as the "static level" or "baseline phase") at or near a minimum level, followed by an abrupt and relatively steeply sloped portion (known as the "growth phase"), and ending with a generally flat portion at or near a maximum level (known as the "plateau phase").

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, for example, a fluorescence measurement such as RFU (y-axis). Some, but not all, growth curves have a sigmoid-shape. The "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero. The "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease. The "plateau phase" refers to the final phase of the curve. In the plateau phase, the rate of measurable product formation is substantially lower than the rate of amplicon production in the log-linear growth phase, and may even approach zero.

Figure 28:
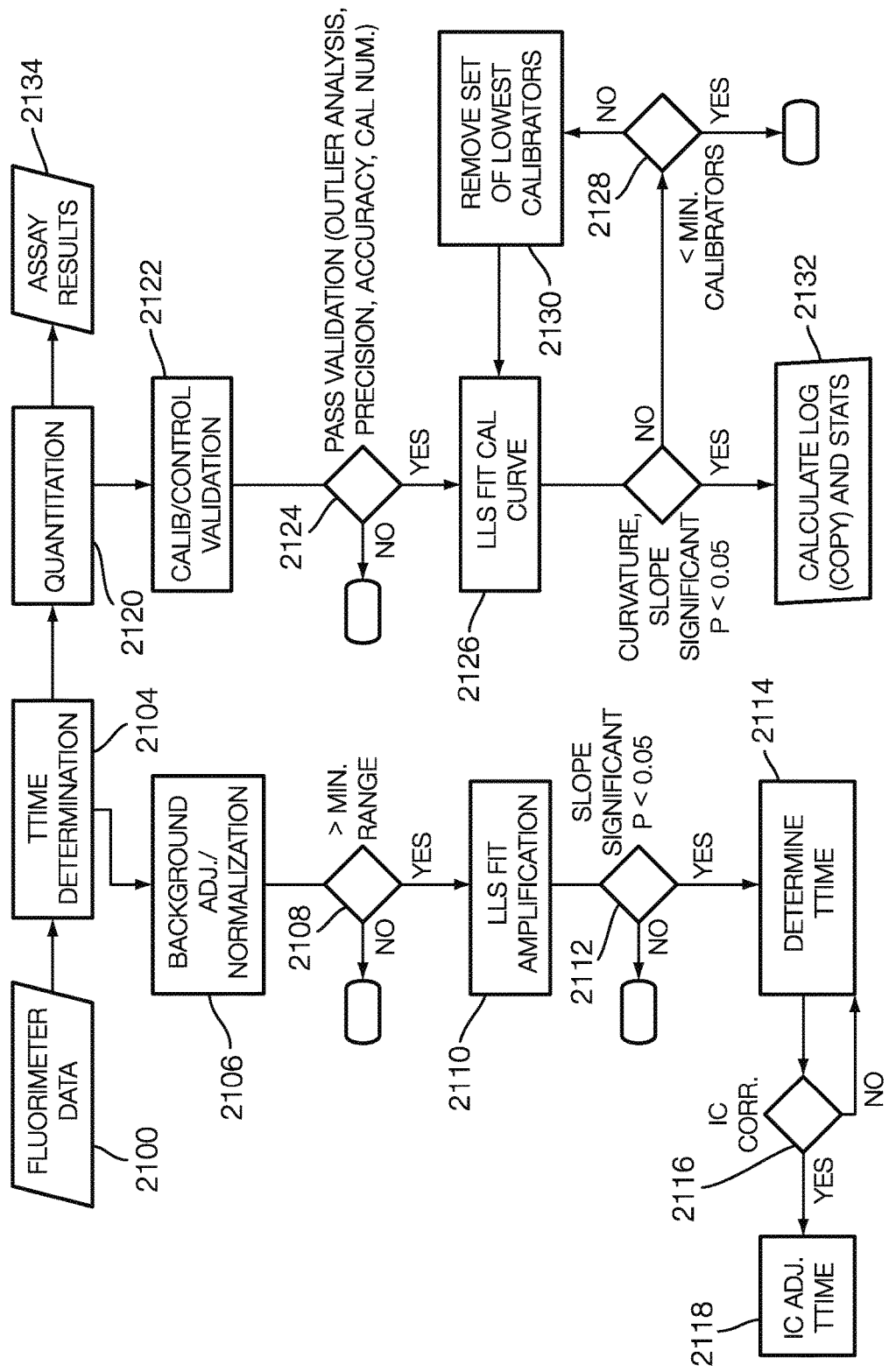
FIG. 28 is a flow chart showing an analyte quantification process, according to an embodiment.

An exemplary process for calculating an analyte concentration is shown a flow chart in FIG. 28. The RFU(t) data from signal detector 400 is input as represented at step 2100. The RFU(t) data goes to threshold time determination, which begins at step 2104. Threshold time, or T-time, (also known as time of emergence) refers to the time at which the data RFU(t), normalized as discussed below, reaches a predefined threshold value. Using calibration curves, as will be described in more detail below, the T-time determined for a particular sample can be correlated with an analyte concentration, thereby indicating the analyte concentration for the sample. Generally, the higher the concentration of the analyte of interest, the sooner the T-time is reached.

The first step of the T-time determination procedure is background adjustment and normalization of the data, as represented at step 2106. Background adjustment is performed to subtract that portion of the signal data RFU(t) that is due to background "noise" from, for example, stray electromagnetic signals. That is, the background noise includes that part of the RFU(t) signal due to sources other than the analyte of interest. Background adjustment is performed by subtracting a background value "BG" from the data RFU(t) to obtain adjusted data RFU*(t). That is, RFU*(t)=RFU(t)−BG.

The background value BG can be determined in a number of ways.

In some embodiments of determining the background noise, the first step is to determine the time intervals between data points. The time interval is determined by multiplying cycle time (i.e., the time between consecutive data measurements) by the data point (i.e., $0^{th}$ data point, $1^{st}$ data point, $2^{nd}$ data point, ..., $n^{th}$ data point) and divide by 60 seconds. For example, assuming a cycle time of 30 seconds, the time interval for the $15^{th}$ data point is (15×30 sec.)/60 sec.=7.5.

The next step is to find the midpoint of the signal data by adding the minimum signal data point and the maximum signal data point and dividing by two. That is, the midpoint equals $(RFU_{max}+RFU_{min})/2$.

Next, starting at the time corresponding to the midpoint value and working backwards, the slope for each pair of data points is calculated: $(RFU(t)-RFU(t-1))/\Delta t(t \rightarrow t-1)$.

Next, determine where the slope of RFU(t) flattens out by finding the first slope value that is less than the static slope value (i.e., the value before the RFU(t) curve begins its upward slope). A representative static slope value, also known as the "delta value," includes 0.0001. Once this slope is found, the next cycle in which the slope that is not negative or is, for example, above the negative delta value (i.e., −0.0001) is determined; this value is $H_{index}$. Next, the mean of the entire range of RFU(t) values starting at the first data point and go to the RFU value that corresponds to the $H_{index}$ value is determined. The mean of this data may be computed using the Excel TRIMMEAN function on this range of data using a static back trim value of 0.15 (that is, the lowest 7.5% of RFU values in the specified range and the highest 7.5% RFU values in the specified range are excluded). This mean value is the background value BG.

Alternatively, the background value BG can be determined in accordance with the procedure described above using a delta value other than 0.0001.

A further alternative method for determining the background value BG eliminates the delta value criterion and instead determines a TRIMMEAN mean of the RFU data from cycle 1 to a prescribed end point, such as the first cycle before 5.5 minutes. For this alternative, the static back trim value may be adjusted to, for example, 0.40 (that is, the lowest 20% of RFU values in the specified range and the highest 20% RFU values in the specified range are excluded from the background calculation).

A further alternative method for determining the background value BG is to perform a curve fit on all or a portion of the RFU data to derive an estimate of the baseline value, which is the background to be subtracted. Any curve fit technique suitable for fitting a curve to the RFU data can be used.

An exemplary curve fit technique uses a portion of the equation derived by Weusten et al. for fitting typically sigmoidal curves associated with nucleic acid amplification. See Weusten et al., Nucleic Acids Research, 30(6e26):1-7 (2002). For background subtraction, it is only necessary to ascertain the baseline level. Thus, it is also only necessary to fit a curve to the first portion of the RFU data encompassing the baseline, usually toward the beginning of the curve.

The curve fitting may be performed on the RFU(t) data from cycle 1 to the cycle just before 75% of the maximum RFU. The following polynomial equation, which, as mentioned above, is a portion of the equation derived by Weusten et al., is used to generate a best fit model of the RFU data:

$$RFU(t) = Y0 + a1 a2 [e^{a2(t-a3)}/(1+e^{a2(t-a3)})] \ln(1+e^{a2(t-a3)})$$

Initial estimates for the variables Y0, a1, a2, and a3, as discussed below, are input to the curve-fit equation and an iterative solution fitting the equation to the RFU data is performed, for example, using the SOLVER function of Microsoft EXCEL, to yield the final equation and the final values for Y0, a1, a2, and a3.

Y0=is the baseline; an initial value can be RFU(1).

a1=relates to the steep portion (growth phase) of the RFU(t) data; 0.05 can be a suitable initial estimate for a1.

a2=relates to the steep portion (growth phase) of the RFU(t) data; 1.0 can be a suitable initial estimate for a2.

a3=relates to the transition between the baseline and the slope feature; the time, or cycle, at which RFU(t) reaches a value just before 25% of $RFU_{max}$ is a suitable initial estimate for a3.

When the final values of Y0, a1, a2, and a3 have been derived, Y0 is treated as the back ground, and is subtracted from the RFU(t) data for which the curve fit was performed.

Curve fit equations other than that described above can be used. For example, the commercially available TABLE-CURVE software package (SYSTAT Software Inc.; Richmond, Calif.) can be used to identify and select equations that describe exemplary real-time nucleic acid amplification curves. One such exemplary resulting equation, used for mathematical modeling, is given by the following equation:

$$RFU(t) = Y0 + b(1 - \exp(-(t - d^* \ln(1 - 2^{-(-1/e)}) - c)/d))^{-e}$$

Still another exemplary resulting equation is given by following equation:

$$RFU(t) = Y0 + b/(1 + \exp(-(t - d^* \ln(2^{-(1/e)} - 1) - c)/d))^{-e}$$

In each case, as described above, the equation can be solved, for example, using the SOLVER function of Microsoft EXCEL, to yield the final equation and the final values for Y0 and the other parameters, and the solutions yields a Y0 that is the background to be subtracted from the RFU(t) data.

To normalize the data at step 2106, each data point, adjusted for the background, is divided by the maximum data point, also adjusted for the background. That is:

$$\text{Normalized } RFU = RFU_n(t) = \frac{RFU^*(t)}{RFU^*_{max}} = \frac{(RFU(t) - BG)}{(RFU_{max} - BG)}$$

Thus, the $RFU_n(t)$ will be from −1 to 1.

In step 2108, the range of data is calculated by subtracting $RFU_{n(min)}$ from $RFU_{n(max)}$. If the calculated range does not meet or exceed a specified, minimum range (e.g., 0.05), the data is considered suspect and of questionable reliability, and, thus, the T-time will not be calculated. The minimum range is determined empirically and may vary from one fluorescence measuring instrument to the next. Ideally, the specified minimum range is selected to ensure that the variation of data values from minimum to maximum exceeds the noise of the system.

In step 2110, a curve fit procedure is applied to the normalized, background-adjusted data. Although any of the well-known curve fit methodologies may be employed, in an embodiment, a linear least squares ("LLS") curve fit is employed. The curve fit is performed for only a portion of the data between a predetermined low bound and high bound. The ultimate goal, after finding the curve that fits the data, is to find the time corresponding to the point at which the curve intersects a predefined threshold value. In an embodiment, the threshold for normalized data is 0.11. The high and low bounds are determined empirically by fitting curves to a variety of control data sets and observing the time at which the various curves cross the chosen threshold. The high and low bounds define the upper and lower ends, respectively, of the range of data over which the curves exhibit the least variability in the times at which the curves cross the given threshold value. In an embodiment, the low bound is 0.04 and the high bound is 0.36—See FIG. 29. The curve is fit for data extending from the first data point below the low bound through the first data point past the high bound.

At step 2110, determine whether the slope of the fit is statistically significant. For example, if the p value of the first order coefficient is less than 0.05, the fit is considered significant, and processing continues. If not, processing stops. Alternatively, the validity of the data can be determined by the R2 value.

The slope m and intercept b of the linear curve y=mx+b are determined for the fitted curve. With that information, T-time can be determined at step 2104 as follows:

$$T\text{-}time = \frac{\text{Threshold} - b}{m}$$

Figure 30:
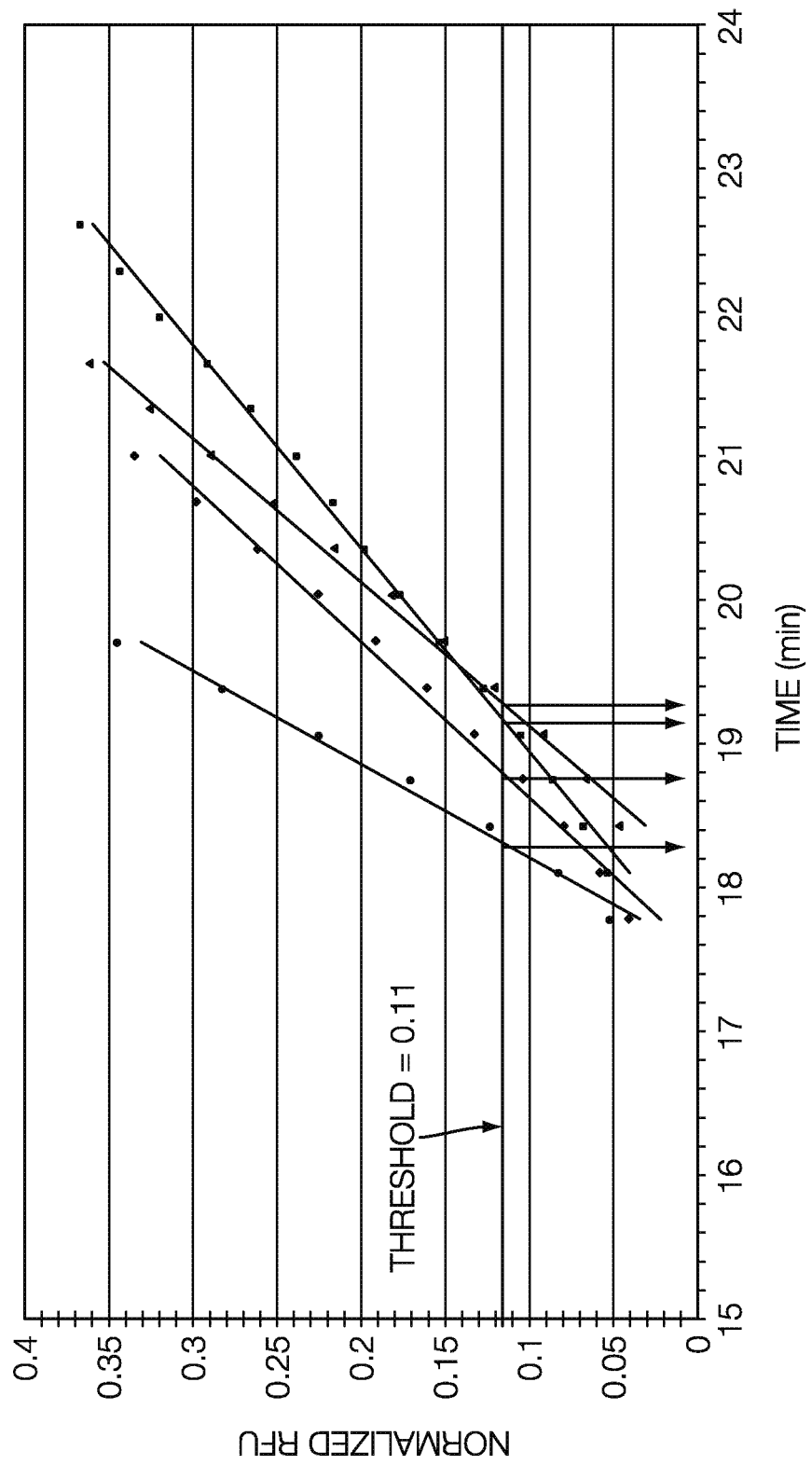
FIG. 30 is a plot showing a method for fitting a curve to real-time fluorometer data and using the fit to determine a threshold time, according to an embodiment.

The technique of using the fitted curve to determine T-times is illustrated graphically in FIG. 30.

At step 2116, it is determined whether or not internal control/calibrator adjustments are desired. Typically, a test procedure would include at least one reaction vessel with a known concentration of a nucleic acid (other than a nucleic acid of interest) as a control, or, alternatively, a control nucleic acid sequence can be added to each sample. The known concentration can be simply used as control to confirm that a reaction did take place in the reaction vessel. That is, if the known concentration is amplified as expected, successful reaction is confirmed and a negative result with respect to the target analyte is concluded to be due to absence of target in the sample. On the other hand, failure to amplify the known concentration as expected indicates a failure of the reaction and any result with respect to the target is ignored.

The known concentration can be used to calibrate the concentration of the target. The T-times corresponding to a series of standards containing internal control and target sequences are determined for a statistically valid number of data sets. Using this data, a calibration plot is constructed from which the test sample's concentration is interpolated as described below.

One method of constructing the calibration plot places the known concentrations of target analyte on the x-axis versus the difference between target and control T-times on the y-axis. Subsequently, the test sample's concentration is interpolated from the calibration curve fit. Another method of constructing the calibration plot places the known concentration of target analyte on the x-axis versus the fraction [target T-time/internal control T-time] on the y-axis. Subsequently, the test sample's concentration is interpolated from the calibration curve fit. An example of this is disclosed in Haaland, et al., "Methods, Apparatus and Computer Program Products for Determining Quantities of Nucleic Acid Sequences in Samples Using Standard Curves and Amplification Ratio Estimates," U.S. Pat. No. 6,066,458. A further alternative method of constructing the calibration plot utilizes a parametric calibration method, such as the method described in Carrick et al., "Parametric Calibration Method," U.S. Pat. No. 7,831,417.

Occasionally, data sets exhibit a dip just after the initial static baseline (i.e., the initial, flat part of the RFU(t) curve, see FIG. 29) and just before the data begins its upward slope. To identify and correct such data, and prior to determining the T-time for that data, the following algorithm is employed. Starting at $H_{index}$, check each RFU(t) value to determine if it is less than the background value, BG. If yes, subtract RFU(t) from BG (the result should be a positive number). This will be the CorValue. Add the CorValue to the background subtracted value, this in turn will bring RFU(t) up to the baseline. Perform this analysis working forward on each RFU(t) value until the latest CorValue is less than the preceding CorValue. Add the greatest CorValue to each of the remaining background subtracted RFU(t) values. Now, the corrected data set can be normalized and the T-time determined as described above.

If a curve fit method is used to derive the background level, it may not be necessary to perform the dip correction described above. In some embodiments, outlier detection on the data set may be performed to identify and, if necessary, discard data points that exhibit abnormal values as compared to the remaining data points. Any of the well-known outlier detection methodologies can be used.

The quantitation procedure 2120 is the second part of the analyte concentration determination. T-times are determined for known concentrations of analytes for known conditions. Using this data, relationships between analyte concentrations (typically expressed as log copy) and T-times can be derived. After a T-time is determined for a particular sample, the derived relationship (Log copy=f(T-time)) can be used to determine the analyte concentration for the sample.

More specifically, at steps 2122 and 2124, calibration/control data sets for a control analyte of known concentrations are validated by, for example, outlier analysis and/or any other known data validation methodologies. If the data is found to be valid, calibration continues, otherwise, calibration stops.

T-times for the control data sets are determined, and T-time vs. Log copy is plotted for all samples of a particular condition (e.g., samples processed with reagents from a particular batch lot). In step 2126, a curve fit, such as a linear least squares fit, is performed on a portion of the T-time vs. Log copy plot to find the slope m and intercept b of the line that best fits the data. If the number of available T-time vs. Log copy data points (known as "calibrators") is not less than a predefined minimum number of calibrators (as determined at step 2128), lowest calibrators, if any, are removed at step 2130, as follows:

After finding the best fit line for the calibrator data points, $2^{nd}$ and $3^{rd}$ order curve fits are tested as well. If these fits are significantly better than the 1st order, linear fit, the calibrator data point that is furthest from the linear curve fit is discarded, and $1^{st}$, $2^{nd}$, and $3^{rd}$ fits are found and compared again with the remaining calibrators. This process is repeated—assuming that the number of calibrators is not less than the minimum acceptable number of calibrators—until the 2nd and 3rd order fits are not significantly better than the $1^{st}$ order, linear fit.

When the linear T-time vs. Log copy equation has been derived, the concentration (as Log copy) of the analyte of interest for a sample is determined, at step 2132, by plugging the T-time for that sample into the equation. Thus, the assay results are obtained 2134.

All documents referred to herein are hereby incorporated by reference herein. No document, however, is admitted to be prior art to the claimed subject matter.

Aspects of this disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the disclosure requires features or combinations of features other than those expressly recited in the claims. Accordingly, the present disclosure is deemed to include all modifications and variations encompassed within the spirit and scope of the following appended claims.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, and without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

While the invention has been described in connection with the above described embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. § 112(¶6), are not intended to be interpreted under 35 U.S.C. § 112(¶6) as being limited to the structure, material, or acts described in the present specification and their equivalents.

What is claimed:

1. An assay instrument comprising:
  a first fluorometer comprising a first detection channel having a first light source and a first sensor, the first detection channel being configured to emit and focus light generated by the first light source at a first detection zone, and to receive and focus light on the first sensor;
  a carrier comprising a first non-fluorescent surface portion, defining a recess, and configured to support a first receptacle, wherein the carrier and the first fluorometer are movable relative to each other among at least (i) a first position at which a portion of the first receptacle is in the first detection zone, (ii) a second position at which the first non-fluorescent surface portion of the carrier is in the first detection zone, and (iii) a third position at which the recess is in the first detection zone; and
  a controller operatively coupled to the first fluorometer and configured to:
  determine a characteristic of a sample contained within the first receptacle based on a first measured intensity of light focused on the first sensor while the carrier is at the first position, and
  determine an operational performance status of the first fluorometer based on at least one of (i) a second measured intensity of light focused on the first sensor while the carrier is at the second position and (ii) a third measured intensity of light focused on the first sensor while the carrier is at the third position.

2. The assay instrument of claim 1, wherein the controller is configured to determine the operational performance status by determining whether the second measured intensity is within a first predetermined non-fluorescent-surface intensity range.

3. The assay instrument of claim 2, wherein the first predetermined non-fluorescent-surface intensity range is greater than zero.

4. The assay instrument of claim 2, wherein the first predetermined non-fluorescent-surface intensity range is between 5-5800 Relative Fluorescent Units (RFU).

5. The assay instrument of claim 1, wherein the controller is configured to determine the operational performance status of the fluorometer by determining whether the third measured intensity is within a first predetermined recess intensity range.

6. The assay instrument of claim 5, wherein the first predetermined recess intensity range includes zero.

7. The assay instrument of claim 5, wherein the first predetermined recess intensity range is between 0-2260 Relative Fluorescent Units (RFU).

8. The assay instrument of claim 1, wherein the controller is configured to determine the operational performance status of the fluorometer based on both the second measured intensity and the third measured intensity.

9. The assay instrument of claim 1, wherein the operational performance status is a failure status or a deteriorated performance status.

10. The assay instrument of claim 1, wherein the characteristic of the sample contained within the first receptacle is whether a particular analyte is present in the sample contained within the first receptacle.

11. The assay instrument of claim 1, wherein the characteristic of the sample contained within the first receptacle is a quantity of a particular analyte in the sample contained within the first receptacle.

12. The assay instrument of claim 1, wherein:
  the first fluorometer further comprises a second detection channel having a second light source and a second sensor, the second detection channel being configured to emit and focus light generated by the second light source at a second detection zone, and to receive and focus light on the second sensor;
  the carrier further comprising a second non-fluorescent surface portion, and further configured to support a second receptacle, wherein the carrier and the first fluorometer are movable relative to each other among at least (i) the first position at which a portion of the second receptacle is in the second detection zone, (ii) the second position, (iii) the third position, and (iv) a fourth position at which the second non-fluorescent surface portion of the carrier is in the second detection zone; and
  the controller is further configured to:
    determine a characteristic of a sample contained within the second receptacle based on a fourth measured intensity of light focused on the second sensor while the carrier is at the first position, and
    determine the operational performance status of the first fluorometer further based on at least one of (i) a fifth measured intensity of light focused on the second sensor while the carrier is at the fourth position and (ii) a sixth measured intensity of light focused on the second sensor while the carrier is at the third position.

13. The assay instrument of claim 12, wherein the controller is configured to determine the operational performance status of the first fluorometer based on the fifth measured intensity by determining whether the fifth measured intensity is within a second predetermined non-fluorescent-surface intensity range.

14. The assay instrument of claim 12, wherein the first non-fluorescent surface portion and the second non-fluorescent surface portion are linearly aligned and are coplanar.

15. The assay instrument of claim 12, wherein each of the first non-fluorescent surface portion and the second non-fluorescent surface portion comprises an aluminum surface.

16. The assay instrument of claim 12, wherein the controller is configured to determine the operational performance status of the first fluorometer by determining whether the sixth measured intensity is within a second predetermined recess intensity range.

17. The assay instrument of claim 12, wherein the controller is configured to determine the operational performance status of the first fluorometer based on both the fifth measured intensity and the sixth measured intensity.

18. The assay instrument of claim 1, further comprising:
a second fluorometer comprising a first detection channel having a first light source and a first sensor, the first detection channel of the second fluorometer being configured to emit and focus light generated by the first light source of the second fluorometer at a first detection zone of the second fluorometer, and to receive and focus light on the first sensor of the second fluorometer;
wherein the carrier further comprises a second non-fluorescent surface portion, further defines a second recess, and is further configured to support a second receptacle;
wherein the carrier and the second fluorometer are movable relative to each other among at least (i) the first position at which a portion of the second receptacle is in the first detection zone of the second fluorometer, (ii) the second position at which the second non-fluorescent surface portion of the carrier is in the first detection zone of the second fluorometer, and (iii) the third position at which the second recess is in the first detection zone of the second fluorometer; and
wherein the controller is further configured to:
determine a characteristic of a sample contained within the second receptacle based on a seventh measured intensity of light focused on the first sensor of the second fluorometer while the carrier is at the first position, and
determine an operational performance status of the second fluorometer based on at least one of (i) an eighth measured intensity of light focused on the first sensor of the second fluorometer while the carrier is at the second position and (ii) a ninth measured intensity of light focused on the first sensor of the second fluorometer while the carrier is at the third position.

19. The assay instrument of claim 18, wherein the controller is configured to determine the operational performance status of the second fluorometer by determining whether the eighth measured intensity is within a second predetermined non-fluorescent-surface intensity range.

20. The assay instrument of claim 19, wherein the second predetermined non-fluorescent-surface intensity range is greater than zero.

21. The assay instrument of claim 18, wherein the controller is configured to determine the operational performance status of the second fluorometer by determining whether the ninth measured intensity is within a first predetermined recess intensity range.

22. The assay instrument of claim 21, wherein the first predetermined recess intensity range includes zero.

23. The assay instrument of claim 18, wherein the controller is configured to determine the operational performance status of the second fluorometer based on both the eighth measured intensity and the ninth measured intensity.

24. The assay instrument of claim 18, wherein:
the second fluorometer further comprises a second detection channel having a second light source and a second sensor, the second detection channel of the second fluorometer being configured to emit and focus light generated by the second light source of the second fluorometer at a second detection zone, and to receive and focus light on the second sensor of the second fluorometer;
the carrier further comprising a third non-fluorescent surface portion, is further configured to support a third receptacle;
the carrier and the second fluorometer are movable relative to each other among at least (i) the first position at which a portion of the third receptacle is in the second detection zone of the second fluorometer, (ii) the second position, (iii) the third position, and (iv) the fourth position at which the third non-fluorescent surface portion of the carrier is in the second detection zone of the second fluorometer; and
the controller is further configured to:
determine a characteristic of a sample contained within the third receptacle based on a tenth measured intensity of light focused on the second sensor of the second fluorometer while the carrier is at the first position, and
determine the operational performance status of the second fluorometer further based on at least one of (i) a eleventh measured intensity of light focused on the second sensor of the second fluorometer while the carrier is at the fourth position and (ii) a twelfth measured intensity of light focused on the second sensor of the second fluorometer while the carrier is at the third position.

25. The assay instrument of claim 24, wherein the second non-fluorescent surface portion and the third non-fluorescent surface portion are linearly aligned and are coplanar.

26. The assay instrument of claim 1, wherein a distance between the first fluorometer and the portion of the first receptacle at the first position is greater than a distance between the first fluorometer and the first non-fluorescent surface portion at the second position.

27. The assay instrument of claim 1, wherein a distance between the first fluorometer and the portion of the first receptacle at the first position is less than a distance between the first fluorometer and the first non-fluorescent surface portion at the second position.

28. The assay instrument of claim 1, wherein the carrier is a carousel comprising a first disk and a second disk spaced apart from the first disk, the second disk being between the first disk and the first fluorometer, and wherein the second disk includes the first non-fluorescent surface portion and defines an opening of the first recess.

29. The assay instrument of claim 28, wherein the second disk comprises concentric inner and outer rings connected by a spoke that includes the first non-fluorescent surface portion.

30. The assay instrument of claim 1, wherein the carrier is movable, and wherein the first fluorometer is stationary.

31. The assay instrument of claim 30, wherein the carrier is rotatable.

32. The assay instrument of claim 1, wherein the carrier is movable, and wherein the first fluorometer is movable.

33. The assay instrument of claim 1, wherein the carrier is stationary, and wherein the first fluorometer is movable.

\* \* \* \* \*